United States Patent
Koenig et al.

(10) Patent No.: US 11,421,031 B2
(45) Date of Patent: *Aug. 23, 2022

(54) BISPECIFIC MOLECULES THAT ARE IMMUNOREACTIVE WITH IMMUNE EFFECTOR CELLS THAT EXPRESS AN ACTIVATING RECEPTOR AND AN ANTIGEN EXPRESSED BY A CELL INFECTED BY A VIRUS AND USES THEREOF

(71) Applicants: MacroGenics, Inc., Rockville, MD (US); Duke University, Durham, NC (US)

(72) Inventors: Scott Koenig, Rockville, MD (US); Leslie S. Johnson, Rockville, MD (US); Chia-Ying Kao Lam, Foster City, CA (US); Liqin Liu, Germantown, MD (US); Jeffrey Lee Nordstrom, Olney, MD (US); Barton F. Haynes, Durham, NC (US); Guido Ferrari, Durham, NC (US)

(73) Assignees: MacroGenics, Inc., Rockville, MD (US); Duke University, Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/908,185

(22) Filed: Jun. 22, 2020

(65) Prior Publication Data
US 2021/0095021 A1  Apr. 1, 2021

Related U.S. Application Data

(63) Continuation of application No. 15/879,056, filed on Jan. 24, 2018, now Pat. No. 10,730,947, which is a continuation of application No. 14/775,041, filed as application No. PCT/US2014/025491 on Mar. 13, 2014, now Pat. No. 9,908,938.

(60) Provisional application No. 61/783,195, filed on Mar. 14, 2013.

(51) Int. Cl.
| | |
|---|---|
| C07K 16/28 | (2006.01) |
| C12N 5/0783 | (2010.01) |
| C07K 16/10 | (2006.01) |
| C07K 16/08 | (2006.01) |
| A61K 39/00 | (2006.01) |

(52) U.S. Cl.
CPC .......... *C07K 16/283* (2013.01); *C07K 16/084* (2013.01); *C07K 16/085* (2013.01); *C07K 16/1027* (2013.01); *C07K 16/1063* (2013.01); *C07K 16/2809* (2013.01); *C12N 5/0638* (2013.01); *A61K 2039/505* (2013.01); *C07K 2317/31* (2013.01); *C07K 2317/626* (2013.01); *C07K 2317/73* (2013.01); *C07K 2317/92* (2013.01); *C12N 2510/00* (2013.01); *C12N 2710/16211* (2013.01); *C12N 2710/20011* (2013.01); *C12N 2740/16111* (2013.01); *C12N 2760/18511* (2013.01)

(58) Field of Classification Search
None
See application file for complete search history.

(56) References Cited

U.S. PATENT DOCUMENTS

| | | |
|---|---|---|
| 3,842,067 A | 10/1974 | Sarantakis |
| 3,862,925 A | 1/1975 | Sarantakis |
| 3,972,859 A | 8/1976 | Fujino et al. |
| 4,105,603 A | 8/1978 | Vale et al. |
| 4,752,601 A | 6/1988 | Hahn |
| 4,816,567 A | 3/1989 | Cabilly et al. |
| 5,116,964 A | 5/1992 | Capon et al. |
| 5,169,933 A | 12/1992 | Anderson et al. |
| 5,348,876 A | 9/1994 | Michaelson et al. |
| 5,565,332 A | 10/1996 | Hoogenboom et al. |
| 5,576,184 A | 11/1996 | Better et al. |
| 5,580,717 A | 12/1996 | Dower et al. |
| 5,585,089 A | 12/1996 | Queen et al. |
| 5,624,821 A | 4/1997 | Winter et al. |
| 5,648,260 A | 7/1997 | Winter et al. |

(Continued)

FOREIGN PATENT DOCUMENTS

| | | |
|---|---|---|
| CN | 103703024 | 4/2014 |
| EP | 0327378 | 8/1989 |

(Continued)

OTHER PUBLICATIONS

US 6,331,391 B1, 12/2001, Wittrup et al. (withdrawn)

(Continued)

*Primary Examiner* — Nianxiang Zou
(74) *Attorney, Agent, or Firm* — William C. Schrot; Jeffrey I. Auerbach; AuerbachSchrot LLC

(57) ABSTRACT

The present invention relates to bispecific molecules that are capable of localizing an immune effector cell that expresses an activating receptor to a virally infected cell, so as to thereby facilitate the killing of the virally infected cell. In a preferred embodiment, such localization is accomplished using bispecific molecules that are immunoreactive with an activating receptor of an immune effector cell and to an antigen expressed by a cell infected with a virus wherein the antigen is detectably present on the cell infected with the virus at a level that is greater than the level at which the antigen is detected on the virus by the bispecific molecules, and to the use of such bispecific molecules in the treatment of latent viral infections.

22 Claims, 8 Drawing Sheets
Specification includes a Sequence Listing.

(56) References Cited

U.S. PATENT DOCUMENTS

| | | |
|---|---|---|
| 5,698,449 A | 12/1997 | Baumann et al. |
| 5,723,584 A | 3/1998 | Schatz |
| 5,731,168 A | 3/1998 | Carter et al. |
| 5,733,743 A | 3/1998 | Johnson et al. |
| 5,736,135 A | 4/1998 | Goeddel et al. |
| 5,736,137 A | 4/1998 | Anderson et al. |
| 5,807,706 A | 9/1998 | Carter et al. |
| 5,807,715 A | 9/1998 | Morrison et al. |
| 5,821,333 A | 10/1998 | Carter et al. |
| 5,866,692 A | 2/1999 | Shitara et al. |
| 5,874,239 A | 2/1999 | Schatz |
| 5,932,433 A | 8/1999 | Schatz |
| 5,985,599 A | 11/1999 | Mckenzie et al. |
| 6,025,485 A | 2/2000 | Kamb et al. |
| 6,114,147 A | 9/2000 | Frenken et al. |
| 6,165,745 A | 12/2000 | Ward et al. |
| 6,194,551 B1 | 2/2001 | Idusogie et al. |
| 6,218,149 B1 | 4/2001 | Morrison et al. |
| 6,242,195 B1 | 6/2001 | Idusogie et al. |
| 6,265,150 B1 | 7/2001 | Terstappen et al. |
| 6,277,375 B1 | 8/2001 | Ward |
| 6,300,065 B1 | 10/2001 | Kieke et al. |
| 6,331,415 B1 | 12/2001 | Cabilly et al. |
| 6,423,538 B1 | 7/2002 | Wittrup et al. |
| 6,455,263 B2 | 9/2002 | Payan |
| 6,472,511 B1 | 10/2002 | Leung et al. |
| 6,492,123 B1 | 12/2002 | Holliger et al. |
| 6,528,624 B1 | 3/2003 | Idusogie et al. |
| 6,538,124 B1 | 3/2003 | Idusogie et al. |
| 6,613,884 B1 | 9/2003 | Johansson et al. |
| 6,623,940 B1 | 9/2003 | Ledbetter et al. |
| 6,737,056 B1 | 5/2004 | Presta |
| 6,821,505 B2 | 11/2004 | Ward |
| 7,122,646 B2 | 10/2006 | Holliger et al. |
| 7,315,786 B2 | 1/2008 | Dahiyat et al. |
| 7,317,091 B2 | 1/2008 | Lazar et al. |
| 7,351,803 B2 | 4/2008 | Johnson et al. |
| 7,425,619 B2 | 9/2008 | Koenig et al. |
| 7,429,652 B2 | 9/2008 | Wang et al. |
| 7,507,797 B2 | 3/2009 | Knackmuss et al. |
| 7,521,542 B2 | 4/2009 | Johnson et al. |
| 7,632,497 B2 | 12/2009 | Stavenhagen |
| 7,642,228 B2 | 1/2010 | Carter et al. |
| 7,695,936 B2 | 4/2010 | Carter et al. |
| 7,700,100 B2 | 4/2010 | Johnson et al. |
| 7,960,512 B2 | 6/2011 | Stavenhagen et al. |
| 8,003,774 B2 | 8/2011 | Stavenhagen et al. |
| 8,044,180 B2 | 10/2011 | Koenig et al. |
| 8,133,982 B2 | 3/2012 | Johnson et al. |
| 8,187,593 B2 | 5/2012 | Koenig et al. |
| 8,192,737 B2 | 6/2012 | Stavenhagen et al. |
| 8,193,318 B2 | 6/2012 | Koenig et al. |
| 8,211,866 B2 | 7/2012 | Zeichner et al. |
| 8,216,574 B2 | 7/2012 | Stavenhagen et al. |
| 8,216,579 B2 | 7/2012 | Johnson et al. |
| 8,216,805 B2 | 7/2012 | Carter et al. |
| 8,217,147 B2 | 7/2012 | Stavenhagen et al. |
| 8,313,746 B2 | 11/2012 | Dimitrov et al. |
| 8,586,713 B2 | 11/2013 | Davis et al. |
| 8,642,743 B2 | 2/2014 | Herne |
| 8,999,398 B2 | 4/2015 | Lum et al. |
| 9,284,375 B2 | 3/2016 | Johnson et al. |
| 2002/0028486 A1 | 3/2002 | Morrison et al. |
| 2003/0077282 A1 | 4/2003 | Bigler et al. |
| 2003/0115614 A1 | 6/2003 | Kanda et al. |
| 2003/0158389 A1 | 8/2003 | Idusogie et al. |
| 2004/0002587 A1 | 1/2004 | Watkins et al. |
| 2004/0038339 A1 | 2/2004 | Kuffer et al. |
| 2004/0058400 A1 | 3/2004 | Holliger et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0220388 A1 | 11/2004 | Mertens et al. |
| 2004/0259075 A1 | 12/2004 | Dimitrov et al. |
| 2005/0037000 A1 | 2/2005 | Stavenhagen et al. |
| 2005/0054832 A1 | 3/2005 | Lazar et al. |
| 2005/0100543 A1 | 5/2005 | Hansen et al. |
| 2005/0142539 A1 | 6/2005 | Herman |
| 2005/0257285 A1 | 11/2005 | Gupta et al. |
| 2005/0260213 A1 | 11/2005 | Koenig et al. |
| 2006/0099216 A1 | 5/2006 | Cardy et al. |
| 2006/0193849 A1 | 8/2006 | Krauss et al. |
| 2007/0004909 A1 | 1/2007 | Johnson et al. |
| 2007/0036799 A1 | 2/2007 | Stavenhagen et al. |
| 2007/0135338 A1 | 6/2007 | O'Neil et al. |
| 2007/0140966 A1 | 6/2007 | Chang et al. |
| 2007/0274998 A1 | 11/2007 | Utku |
| 2008/0085277 A1 | 4/2008 | Cho et al. |
| 2008/0187517 A1 | 8/2008 | Herne |
| 2009/0060910 A1 | 3/2009 | Johnson et al. |
| 2009/0162353 A1 | 6/2009 | Johnson et al. |
| 2010/0040601 A1 | 2/2010 | Cantin et al. |
| 2010/0040635 A1 | 2/2010 | Horowitz et al. |
| 2010/0174053 A1* | 7/2010 | Johnson ............... C07K 16/283 530/389.7 |
| 2010/0196362 A1 | 8/2010 | Stavenhagen et al. |
| 2010/0196372 A1 | 8/2010 | Johnson et al. |
| 2010/0322924 A1 | 12/2010 | Johnson et al. |
| 2011/0033389 A1 | 2/2011 | Chen et al. |
| 2011/0076268 A1 | 3/2011 | Williamson et al. |
| 2011/0212076 A1 | 9/2011 | Vyakarnam et al. |
| 2011/0243941 A1 | 10/2011 | Stavenhagen et al. |
| 2011/0305714 A1 | 12/2011 | Stavenhagen et al. |
| 2011/0319871 A1 | 12/2011 | Wood |
| 2012/0009186 A1 | 1/2012 | Koenig et al. |
| 2012/0093834 A1 | 4/2012 | Horowitz et al. |
| 2012/0128669 A1 | 5/2012 | Depla et al. |
| 2012/0141476 A1 | 6/2012 | Johnson et al. |
| 2012/0219551 A1 | 8/2012 | Johnson et al. |
| 2012/0263711 A1 | 10/2012 | Stavenhagen et al. |
| 2012/0269811 A1 | 10/2012 | Johnson et al. |
| 2012/0276094 A1 | 11/2012 | Stavenhagen et al. |
| 2012/0283438 A1 | 11/2012 | Lazarides et al. |
| 2014/0205612 A1 | 4/2014 | Chan-Hui et al. |

FOREIGN PATENT DOCUMENTS

| | | |
|---|---|---|
| EP | 0359096 | 3/1990 |
| EP | 308936 B1 | 7/1994 |
| EP | 1354600 | 10/2003 |
| EP | 1670826 | 2/2012 |
| JP | 2007-531788 | 10/2005 |
| WO | WO 1988/007089 | 9/1988 |
| WO | WO 1989/007142 | 8/1989 |
| WO | WO 1992/016562 | 10/1992 |
| WO | WO 1993/008829 | 5/1993 |
| WO | WO 1993/022332 | 11/1993 |
| WO | WO 1994/018330 | 8/1994 |
| WO | WO 1994/029351 | 12/1994 |
| WO | WO 1995/005468 | 2/1995 |
| WO | WO 1997/028267 | 8/1997 |
| WO | WO 1997/034631 | 9/1997 |
| WO | WO 1997/044362 | 11/1997 |
| WO | WO 1998/005787 | 2/1998 |
| WO | WO 1998/023289 | 6/1998 |
| WO | WO 1998/052975 | 11/1998 |
| WO | WO 1999/043713 | 9/1999 |
| WO | WO 1999/051642 | 10/1999 |
| WO | WO 1999/058572 | 11/1999 |
| WO | WO 2000/009560 | 2/2000 |
| WO | WO 2000/042072 | 7/2000 |
| WO | WO 2001/011059 | 2/2001 |
| WO | WO 2002/002781 | 1/2002 |
| WO | WO 2002/060919 | 8/2002 |
| WO | WO 2002/086070 | 10/2002 |
| WO | WO 2003/035835 | 5/2003 |
| WO | WO 2003/074679 | 9/2003 |
| WO | WO 2003/101485 | 12/2003 |
| WO | WO 2004/001064 | 12/2003 |
| WO | WO 2004/016750 | 2/2004 |
| WO | WO 2004/029207 | 4/2004 |
| WO | WO 2004/065423 | 8/2004 |
| WO | WO 2004/074455 | 9/2004 |
| WO | WO 2004/099249 | 11/2004 |

(56) References Cited

FOREIGN PATENT DOCUMENTS

| | | |
|---|---|---|
| WO | WO 2005/061547 | 7/2005 |
| WO | WO 2005/070963 | 8/2005 |
| WO | WO 2005/097202 | 10/2005 |
| WO | WO 2006/020114 | 2/2006 |
| WO | WO 2006/044410 | 4/2006 |
| WO | WO 2006/113665 | 10/2006 |
| WO | WO 2007/042261 | 4/2007 |
| WO | WO 2008/157379 | 12/2008 |
| WO | WO 2009/058888 | 5/2009 |
| WO | WO 2010/080538 | 7/2010 |
| WO | WO 2011/057124 | 5/2011 |
| WO | WO 2011/085289 | 7/2011 |
| WO | WO 2012/018687 | 2/2012 |
| WO | WO 2012/030904 | 3/2012 |
| WO | WO 2014/159940 | 10/2012 |
| WO | WO 2012/162067 | 11/2012 |
| WO | WO 2012/162068 | 11/2012 |
| WO | WO 2013/163427 | 10/2013 |
| WO | WO 2013/192589 | 12/2013 |
| WO | WO 2014/052620 | 4/2014 |

OTHER PUBLICATIONS

Ferrari et al. An HIV-1 gp120 Envelope Human Monoclonal Antibody That Recognizes a C1 Conformational Epitope Mediates Potent Antibody-Dependent Cellular Cytotoxicity (ADCC) Activity and Defines a Common ADCC. Journal of Virology, Jul. 2011, vol. 85, p. 7029-7036.*

Gao et al. Efficient inhibition of multidrug-resistant human tumors with a recombinant bispecific anti-P-glycoproteinanti-CD3 diabody. Leukemia (2004) 18, 513-520.*

Chamow et al. A Humanized, Bispecific Immunoadhesin-Antibody That Retargets CD3+ Effectors to Kill HIV-1-Infected Cells. The Journal of Immunology, 1994, 153: 4268-4280.*

Liao et al. Immunogenicity of Constrained Monoclonal Antibody A32-Human Immunodeficiency Virus (HIV) Env gp120 Complexes Compared to That of Recombinant HIV Type 1 gp120 Envelope Glycoproteins. J. Virol., May 2004, 78: 5270-5278.*

Alt et al., "Novel Tetravalent and Bispecific IgG-Like Antibody Molecules Combining Single-Chain Diabodies with the Immunoglobin Gamma 1 Fc or CH3 Region," FEBS Letters 454: 90-94, 1999.

Altman et al., "Phenotypic Analysis of Antigen-Specific T Lymphocytes", Science 274:94-96, 1996.

Angal et al., "A single amino acid substitution abolishes the heterogeneity of chimeric mouse-human (IgG4) antibody," Mol Immunol 30 :105-108, 1993.

Anonymous, "Boehringer Ingelheim and MacroGenics Announce Global Alliance to discover, Develop and Commercialize DART(tm)-Based Antibody Therapeutics;" Press Release of MacroGenics, Inc.; Oct. 26, 2010; 3 pages.

Anonymous, "MacroGenics Enters Global Research Collaboration and License Agreement with Pfizer;" Press Release of MacroGenics, Inc.; Oct. 26, 2010; 2 pages.

Apostolovic, B. et al. (2008) "pH-Sensitivity of the E3-K3 Heterodimeric Coiled Coil," Biomacromolecules 9:3173-3180.

Arbiza, J. et al. (1992) "Characterization of Two Antigenic Sites Recognized by Neutralizing Monoclonal Antibodies Directed Against the Fusion Glycoprotein of Human Respiratory Syncytial Virus," J. Gen. Virol. 73(9):2225-2234.

Armour et al., "Differential binding to human FcgammaRIIa and FcgammaRIIb receptors by human IgG wildtype and mutant antibodies," Mol Immunol 40 :585-593, 2003.

Armour et al., "Recombinant human IgG molecules lacking Fcgamma receptor I binding and monocyte triggering activities," Eur J Immunol 29:2613-2624, 1999.

Armour et al., "The contrasting IgG-binding interactions of human and herpes simplex virus Fc receptors," Biochemical Society Transactions 30:495-500, 2002.

Armstrong, S. et al. "Heterogeneity of IgG1 monoclonal anti-Rh(D): an investigation using ADCC and macrophage binding assays," Brit. J. Haematol. 66:257-262 (1987).

Arndt, K.M. et al. (2001) "Helix-stabilized Fv (hsFv) Antibody Fragments: Substituting the Constant Domains of a Fab Fragment for a Heterodimeric Coiled-coil Domain," J. Molec. Biol. 312:221-228.

Arndt, K.M et al. (2002) "Comparison of in Vivo Selection and Rational Design of Heterodimeric Coiled Coils," Structure 10:1235-1248.

Aruffo, A. et al. (1987) "Molecular Cloning of A CD28 cDNA by A High-Efficiency COS Cell Expression System," Proc. Natl. Acad. Sci. (U.S.A.) 84:8573-8577.

Asano, R. et al. (2004) "A Diabody for Cancer Immunotherapy and Its Functional Enhancement by Fusion of Human Fc Region," Abstract 3P-683, J. Biochem. 76(8):992.

Ashkenazi A et al. (1990) "Mapping the CD4 binding site for human immunodeficiency virus by alanine-scanning mutagenesis," Proc. Natl. Acad. Sci. USA 87:7150-7154.

Atwell, S. et al. (1997) "Stable Heterodimers from Remodeling the Domain Interface of a Homodimer Using a Phage Display Library," J. Mol. Biol. 270:26-35.

Babcock, G.J. et al. (1999) "Epstein-Barr Virus-Infected Resting Memory B Cells, Not Proliferating Lymphoblasts, Accumulate in The Peripheral Blood of Immunosuppressed Patients," J. Exp. Med. 190(4):567-576.

Baeuerle, P. et al. (2008) "BiTE: A New Class of Antibodies That Recruit T Cells," Drugs of the Future 33:137-147.

Baggiolini M, Dewald B. "Cellular models for the detection and evaluation of drags that modulate human phagocyte activity," Experientia. Oct. 15;44(10):841-848, 1988.

Bargou, R et al. (2008) "Tumor Regression in Cancer Patients by Very Low Doses of a T Cell-Engaging Antibody," Science 321:974-977.

Beasley, D.W. (2011) "Vaccines and Immunotherapeutics for The Prevention and Treatment of Infections with West Nile Virus," Immunotherapy 3(2):269-285.

Bedzyk et al. (1989) "Comparison of Variable Region Primary Structures Within an Anti-Fluorescein Idiotype Family," J. Biol. Chem, 264(3):1565-1569.

Beeler, J. A. et al. (1989) "Neutralization Epitopes of the F Glycoprotein of Respiratory Syncytial Virus: Effect of Mutation Upon Fusion Function," J. Virol. 63(7):2941-2950.

Beigel, J. et al. (2008) "Current and Future Antiviral Therapy of Severe Seasonal and Avian Influenza," Antiviral Res. 78(1):91-102.

Berg, J. et al. (1991) "Bispecific Antibodies That Mediate Killing of Cells Infected with Human Immunodeficiency Virus of Any Strain," Proc. Natl. Acad. Sci. U.S.A. 88:4723-4727.

Bernard, A. et al. (2005) "T and B Cell Cooperation: A Dance of Life and Death," Transplantation 79: S8-S11.

Berry, J.D. et al. (2011) "Antibodies in Infectious Diseases: Polyclonals, Monoclonals and Niche Biotechnology," Nature Biotechnol, 28(5):489-501.

Bird, R.E. et al. (1988) "Single-Chain Antigen-Binding Proteins," Science 242:423-426.

Boder and Wittrup, "Optimal screening of surface-displayed polypeptide libraries," Biotechnol Prog 14:55-62, 1998.

Boder and Wittrup, "Yeast surface display for directed evolution of protein expression, affinity, and stability," Methods in Enzymology 328:430-444, 2000.

Boder and Wittrup, 1997, "Yeast surface display for screening combinatorial polypeptide libraries", Nature Biotechnology 15:553-557.

Boder et al., "Directed evolution of antibody fragments with monovalent femtomolar antigen-binding affinity," Proc. Natl. Acad. Sci. USA 97:10701-10705, 2000.

Boucher, C. et al. (2010) "Protein Detection by Western Blot Via Coiled—Coil Interactions," Analytical Biochemistiy 399:138-140.

Bredius et al., "Role of neutrophil Fc gamma RIIa (CD32) and Fc gamma RIIIb (CD 16) polymorphic forms in phagocytosis of human IgG1- and IgG3-opsonized bacteria and erythrocytes," Immunology 83:624-630, 1994.

(56) References Cited

OTHER PUBLICATIONS

Brekke et al., "Human IgG isotype-specific amino acid residues affecting complement-mediated cell lysis and phagocytosis.," Eur J Immunol 24:2542-2547, 1994.
Brown EJ., vol. 45 (Microbes as Tools for Cell Biology) in Methods in Cell Biololgy, Russell ed. Academic Press Inc. pp. 147-164, 1994.
Buchacher, A. et al. (1994) "Generation of Human Monoclonal Antibodies Against HIV-1 Proteins; Electrofusion and Epstein-Barr Virus Transformation for Peripheral Blood Lymphocyte Immortalization," AIDS Res. Hum. Retrovimses 10(4):359-369.
Burmeister et al., "Crystal structure of the complex of rat neonatal Fc receptor with Fc," Nature 372:379-383, 1994.
Burton and Woof, "Human antibody effector function," Advances in Immunology 51:1-64, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Cachia, P.J. et al. (2004) "Synthetic Peptide Vaccine Development: Measurement of Polyclonal Antibody Affinity and Cross-Reactivity Using a New Peptide Capture and Release System for Surface Plasmon Resonance Spectroscopy," J. Mol. Recognit. 17:540-557.
Canfield and Morrison, "The binding affinity of human IgG for its high affinity Fc receptor is determined by multiple amino acids in the CH2 domain and is modulated by the hinge region," J Exp Med 173:1483-1491, 1991.
Caron et al., "Engineered humanized dimeric forms of IgG are more effective antibodies," J Exp Med 176 :1191-5, 1992.
Carter P. et al., "Humanization of an anti-p185HER2 antibody for human cancer therapy," Proc. Natl. Acad. Sci. USA 89:4285-4289, 1992.
Cartron et al., "Therapeutic activity of humanized anti-CD20 monoclonal antibody and polymorphism in IgG Fc receptor FcgammaRIIIa gene," Blood 99 :754-758, 2002.
Chamow, S.M., et al. (1994) "A Humanized, Bispecific Immunoadhesin-Antibody That Retargets CD3+ Effectors to Kill HIV-1-Infected Cells[1]," J. Immunol. 153:4268-4280.
Chan, C.E. et al. (2009) "The Use of Antibodies in The Treatment of Infectious Diseases," Singapore Med. J. 50(7):663-673.
Chappel et al., "Identification of a secondary Fc gamma RI binding site within a genetically engineered human IgG antibody," J Biol. Chem 268:25124-25131, 1993.
Chappel et al., "Identification of the Fc gamma receptor class I binding site in human IgG through the use of recombinant IgG1-IgG2 hybrid and point-mutated antibodies," Proc. Natl. Acad. Sci USA 88:9036-9040, 1991.
Chen, Y.P., et al. (2007) "Rapid Detection of Hepatitis B Virus Surface Antigen by an Agglutination Assay Mediated by a Bispecific Diabody against Both Human Erythrocytes and Hepatitis B Virus Surface Antigen," Clin. Vaccine Immunol. 14(6):720-725.
Chu, P. G. et al. (2001) "CD79: A Review," Appl. Immunohistochem. Molec. Morphol. 9(2):97-106.
Ciccimarra et al., "Localization of the IgG effector site for monocyte receptors," Proc. Natl. Acad. Sci. U.S.A. 72 :2081-2083, 1975.
Clynes and Ravetch, "Cytotoxic antibodies trigger inflammation through Fc receptors," Immunity 3:21-26, 1995.
Clynes et al., "Fc receptors are required in passive and active immunity to melanoma," Proc. Natl. Acad. Sci USA 95:652-656, 1998.
Clynes et al., "Inhibitory Fc receptors modulate in vivo cytoxicity against tumor targets," Nature Medicine 6 :443-446, 2000.
Clynes et al., "Modulation of immune complex-induced inflammation in vivo by the coordinate expression of activation and inhibitory Fc receptors," J Exp Med 189:179-185, 1999.
Clynes et al., "Uncoupling of immune complex formation and kidney damage in autoimmune glomerulonephritis," Science 279:1052-1054, 1998.
Co, M. S. et al. (1991) "Humanized Antibodies for Antiviral Therapy," Proc. Natl. Acad. Sci. (U.S.A.) 88:2869-2873.

Co, M.S. et al. (1992) "Chimeric and Humanized Antibodies with Specificity for The CD33 Antigen," J. Immunol. 148:1149-1154.
Conner, R. et al. (1991) "Fc receptors for IgG (FcγRs) on human monocytes and macrophages are not infectivity receptors for human immunodeficiency vims type 1 (HIV-1): Studies using bispecific antibodies to target HIV-1 to various myeloid cell surface molecules, including the FcγR," PNAS 88:9593-9597.
Craig R.B. et al. (2012) "Anti-HIV Double Variable Domain Immunoglobulins Binding Both gp41 and gp120 for Targeted Delivery of Immunoconjugates," PLoS ONE 7(10): e46778. doi: 10.1371/journal.pone.0046778.
Cuesta, A.M. et al. (2010) "Multivalent Antibodies: When Design Surpasses Evolution," Trends in Biotechnol., 28(7):355-362.
Darwish, I.A. (2003) *Immunoassay Methods and their Applications in Pharmaceutical Analysis: Basic Methodology and Recent Advances*, Int J Biomed Sci 2(3):217-235.
De Crescenzo, G.D. et al. (2003) "Real-Time Monitoring of the Interactions of Two-Stranded de novo Designed Coiled-Coils: Effect of Chain Length on the Kinetic and Thermodynamic Constants of Binding," Biochemistry 42:1754-1763.
De Haas, Wien Kin "IgG-Fc receptors and the clinical relevance of their polymorphisms," Wien Klin Wochenscha 113:825-831, 2001.
De Kruif, J. et al. (1996) "Leucine Zipper Dimerized Bivalent and Bispecific scFv Antibodies from a Semi-Synthetic Antibody Phage Display Library," J. Biol. Cherm. 271(13):7630-7634.
Deisenhofer, "Crystallographic refinement and atomic models of a human Fc fragment and its complex with fragment B of protein A Form *Staphylococcus aureus* at 2.9- and 2.8-A resolution," Biochem. 20:2361-2370, 1981.
Deo et al., "Clinical significance of IgG Fc receptors and Fc gamma R-directed immunotherapies," Immunology Today 18:127-135, 1997.
Dong, C. et al. (2003) "Immune Regulation by Novel Costimulatory Molecules," Immunolog. Res. 28(1):39-48.
Duncan and Winter, "Localization of the binding site for the human high-affinity Fc receptor on IgG," Nature 332:563-564, 1988.
Duncan and Winter, "The binding site for C1q on IgG," Nature 332 :738-740, 1988.
Duval, M. et al. (2008) "A Bispecific Antibody Composed of a Nonneutralizing Antibody to the gp41 Immunodominant Region and an Anti-CD89 Antibody Directs Broad Human Immunodeficiency Virus Destruction by Neutrophils," J. Virol. 82:4671-4674.
Edberg et al., "Modulation of Fcgamma and Complement Receptor Function by the Glycosyl-Phosphatidylinositol-AnchoredFormofFcgammaRIII," Journal of Immunology 152: 5826-5835, 1994.
Elkabetz, Y. et al. (2005) "Cysteines in CH1 Underlie Retention of Unassembled Ig Heavy Chains," J. Biol. Chem. 280:14402-14412.
European Search Report (EP 06750508) dated Nov. 2, 2010 (19 pages).
European Search Report (EP 08771050) dated Nov. 2, 2010 (13 pages).
Fang, C.Y. et al. (2004) "Construction and Characterization of Monoclonal Antibodies Specific to Epstein-Barr Virus Latent Membrane Protein 1," J. Immunol. Methods 287(1-2):21-30.
Fernandez-Rodriguez, J. et al. (2012) "Induced Heterodimerization and Purification of Two Target Proteins by A Synthetic Coiled-Coil Tag," Protein Sci. 21:511-519.
Ferrari, G. et al. (2011) "An HIV-1 gp120 Envelope Human Monoclonal Antibody That Recognizes a C1 Conformational Epitope Mediates Potent Antibody-Dependent Cellular Cytotoxicity (ADCC) Activity and Defines a Common ADCC Epitope in Human HIV-1 Serum," J. Virol. 85(14):7029-7036.
First Office Action, Chinese Patent Application No. 201580063039.0 (dated Mar. 12, 2020) (12 pages).
FitzGerald, et al., "Improved tumour targeting by disulphide stabilized diabodies expressed in Pichia pastoris," Protein Engineering 10(10): 1221-1225, 1997.
Flesch and Neppert, "Functions of the Fc receptors for immunoglobulin G," J Clin Lab Anal 14:141-156, 2000.
Fronde, J.W. et al. (2011) "Antibodies for Biodefense," MAbs 3(6):517-527.
Fruehling, S. et al. (1996) "Identification of Latent Membrane Protein 2A (LMP2A) Domains Essential for The LMP2A Dominant-

(56) References Cited

OTHER PUBLICATIONS

Negative Effect On B-Lymphocyte Surface Immunoglobulin Signal Transduction," J Virol. 70:6216-6226.
Fruehling, S. et al. (1998) "Tyrosine 112 Of Latent Membrane Protein 2A Is Essential for Protein Tyrosine Kinase Loading and Regulation of Epstein-Barr Virus Latency," J. Virol. 72:7796-7806.
Galun, E. et al. (2002) "Clinical Evaluation (Phase I) Of A Combination of Two Human Monoclonal Antibodies to HBV: Safety and Antiviral Properties," Hepatology 35:673-679.
Ganesan, A. (2006) "Solid-Phase Synthesis in The Twenty-First Century," Mini Rev. Med. Chem. 6(1):3-10.
Gao, Y. et al. (2004) "Efficient Inhibition of Multidrug-Resistant Human Tumors with a Recombinant Bispecific Anti-P-Glycoprotein X Anti-CD3 Diabody," Leukemia 18(3):513-520.
Geevarghese, B. et al. (Epub Feb. 3, 2012) "Antibodies for Prevention and Treatment of Respiratory Syncytial Virus Infections in Children," Antivir, Then 17(1 Pt B):201-211.
Gergeley et al., "Fc receptors on lymphocytes and K cells," Biochemical Society Transactions 12:739-743, 1984.
Gergely and Sarmay, "The two binding-site models of human IgG Binding Fc gamma receptors," FASEB J 4:3275-3283, 1990.
Ghosh, T.S. et al. (2009) "End-To-End and End-To-Middle Interhelical Interactions: New Classes of Interacting Helix Pairs in Protein Structures," Acta Cryst. D65:1032-1041.
Gorman, S. D. et al. (1991) "Reshaping A Therapeutic CD4 Antibody," Proc. Natl. Acad. Sci. (U.S.A.) 88:4181-4185.
Greenwood and Clark, "Effector functions of matched sets of recombinant human IgG subclass antibodies". (final version edited Feb. 11, 1993).
Greenwood et al., "Engineering multiple-domain forms of the therapeutic antibody CAMPATH-1H: effects on complement lysis," Therapeutic Immunology 1:247-255, 1994.
Greenwood et al., "Structural motifs involved in human IgG antibody effector functions," Eur J Immunol 23:1098-1104, 1993.
Grigoryan, G. et al. (2008) "Structural Specificity in Coiled-Coil Interactions," Curr. Opin. Struc. Biol. 18:477-483.
Gruber, M. et al. (1994) "Efficient Tumor Cell Lysis Mediated by A Bispecific Single Chain Antibody Expressed in *Escherichia coli*," J. Immunol. 152(11):5368-5374.
Guan, Y. et al. (2012) "Diverse specificity and effector function among human antibodies to HIV-1 envelope glycoprotein epitopes exposed by CD4 binding," PNAS 110:E69-E78.
Guo, J. et al. (2003) "[New Type Recombinant Antibody Fragment Scfv Multimer and Cancer Targeting]," Sheng Wu Yi Xue Gong Cheng Xue Za Zhi 20(2):361-365 (Abstract Only; Article in Chinese).
Guo, N. et al. (2005) "The Development of New Formats of Engineered Bispecific Antibodies," in Trends in Immunology Research, Veskler, Ed. Nova Science Publishers. Chapter 3:33-47.
Hadley et al., "The functional activity of Fc gamma RII and Fc gamma RIII on subsets of human lymphocytes," Immunology 76:446-451, 1992.
Hansel, T.T. et al. (2010) "The Safety and Side Effects of Monoclonal Antibodies," Nat. Rev. Drug Discov. 9(4):325-338.
Harris, A. et al. (2011) "Trimeric HIV-1 Glycoprotein Gp140 Immunogens and Native HIV-1 Envelope Glycoproteins Display the Same Closed and Open Quaternary Molecular Architectures," Proc. Natl. Acad. Sci. (U.S.A.) 108(28):11440-11445.
Hatta et al., "Association of Fc gamma receptor IIIB, but not of Fc gamma receptor IIA and IIIA polymorphisms with systemic lupus erythematosus in Japanese," Genes and Immunity 1:53-60, 1999.
Hayes, Fc Engineering to Enhance Monoclonal Antibody Effector Functions. (Presentation) Xecor, CA, 2003.
Heijtink, R.A. et al. (2001) "Administration of A Human Monoclonal Antibody (TUVIRUMAB) To Chronic Hepatitis B Patients Pre-Treated with Lamivudine: Monitoring of Serum TUVIRUMAB in Immune Complexes," J. Med. Virol. 64:427-434.
Herzenberg et al., "The history and future of the fluorescence activated cell sorter and flow cytometry: a view from Stanford," Clinical Chem. 2002:48:1819-1827, 2002.
Heyman, "Regulation of antibody responses via antibodies, complement, and Fc receptors," Annu Rev Immunol 18:709-737, 2000.
Hogarth et al., "Characterization of FcR Ig-binding sites and epitope mapping," Immunomethods 4 :17-24, 1994.
Holler et al., "In vitro evolution of a T cell receptor with high affinity for peptide-MHC," Proc. Natl. Acad. Sci. U.S.A. 97 :5387-92, 2000.
Holliger, et al., "Engineered antibody fragments and the rise of single domains," Nature Biotechnology 23(9): 1126-1135, Sep. 2005.
Houghten, R.A. (1985) "General Method for The Rapid Solid-Phase Synthesis of Large Numbers of Peptides: Specificity of Antigen-Antibody Interaction at The Level of Individual Amino Acids," Proc. Natl. Acad. Sci. (U.S.A.) 82(15):5131-5135.
Howell AL, et al. (1994) "Role of Fc gamma receptors in cancer and infectious disease," J Leukoc Biol 55:816-26.
Huang, J.X. et al. (Epub Jun. 4, 2012) "Development of Anti-Infectives Using Phage Display: Biological Agents Against Bacteria, Viruses, And Parasites," Antimicrob. Agents Chemother. 56(9):4569-4582.
Huber, M. et al. (2008) "Antibodies for HIV Treatment and Prevention: Window of Opportunity?" Curr. Top. Microbiol. Immunol. 317:39-66.
Hudson, P.J. et al. (1999) "High avidity scFv multimers; diabodies and triabodies," J. Immunol. Methods 231(1-2):177-189.
Hulett et al., "Chimeric Fc receptors identify functional domains of the murine high affinity receptor for IgG," J Immunol 147 :1863-1868, 1991.
Hulett et al., "Identification of the IgG binding site of the human low affinity receptor for IgG Fc gamma RII. Enhancement and ablation of binding by site-directed mutagenesis," J. Biol. Chem. 269:15287-15293, 1994.
Hulett et al., "Multiple regions of human Fc gamma RII (CD32) contribute to the binding of IgG," J. Biol. Chem. 270:21188-21194, 1995.
Ian Gust, A.O. (Epub Feb. 21, 2012) "Role of Passive Immunotherapies in Managing Infectious Outbreaks," Biologicals 40(3):196-199.
Idusogie et al., "Engineered antibodies with increased activity to recruit complement," J Immunol 166 :2571-2575, 2001.
Idusogie et al., "Mapping of the C1q binding site on rituxan, a chimeric antibody with a human IgG1 Fc," J Immunol 164: 4178-4184, 2000.
International Search Report and Written Opinion PCT/US2014/025491 (2014) (20 pages).
Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148 :3062-3071, 1992.
Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.
Jassal et al., "Remodeling glycans on IgG by genetic re-engineering," Biochem Soc Trans 26: S113, 1998.
Jefferis and Lund, "Interaction sites on human IgG-Fc for FegammaR: current models," Immunology Letters 82 :57-65, 2002.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gamma R)," Mol Immunol 27 :1237-1240, 1990.
Jefferis et al., "Recognition sites on human IgG for Fc gamma receptors: the role of glycosylation," Immunol Lett 44 :111-7, 1995.
Jendeberg et al., "Engineering of Fc (1) and Fc (3) from human immunoglobulin G to analyse subclass specificity for staphylococcal protein A," J Immunological Methods 201 :25-34, 1997.
Johnson et al., (2010) "Effector Cell Recruitment with Novel Fv-based Dual-affinity Re-targeting Protein Leads to Potent Tumor Cytolysis and in Vivo B-cell Depletion," J. Mol. Biol (399) pp. 436-449.

(56) References Cited

OTHER PUBLICATIONS

Kadar et al., "Modulatory effect of synthetic human IgG Fc peptides on the in vitro immune response of murine spleen cells," Int J Immunpharmacol 13 :1147-55, 1991.

Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.

Kato et al., "Structural basis of the interaction between IgG and Fcγ receptors," J Mol Biol 295:213-224, 2000.

Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.

Kettleborough, C. A. et al. (1991) "Humanization of A Mouse Monoclonal Antibody by CDR-Grafting: The Importance of Framework Residues On Loop Conformation," Protein Engineering 4:773-3783.

Khawli, L.A. et al. (2008) "Cytokine, Chemokine, and Co-Stimulatory Fusion Proteins for the Immunotherapy of Solid Tumors," Exper, Pharmacol. 181:291-328.

Kieke et al., "Selection of functional T cell receptor mutants from a yeast surface-display library," Proc. Natl. Acad. Sci. U.S.A. 96 :5651-56, 1999.

Kiick, K.L. et al. (2001) "Identification of an Expanded Set of Translationally Active Methionine Analogues in *Escherichia coli*," FEBS Lett. 502(1-2):25-30.

Kim et al., "Analysis of FcγRIII and IgG Fc polymorphism reveals functional and evolutionary implications of protein-protein interaction," J Mol Evol 53:1-9, 2001.

Klein et al., "Expression of biological effector functions by immunoglobulin G molecules lacking the hinge region," Proc. Natl. Acad. Sci. U.S.A. 78 :524-528, 1981.

Koene et al., "Fc gammaRIIIa-158V-F polymorphism influences the binding of IgG by natural killer cell Fc gammaRIIIa, independently of the Fc gammaRIIIa-48L-R-H phenotype," Blood 90 :1109-1114, 1997.

Koenig, S. (2014) "Harnessing Effector and Regulatory Pathways for Immunotherapy," presented at the Strategies for an HIV Cure Meeting, Rockville MD.

Kohler, G. et al. (1975) "Continuous Cultures of Fused Cells Secreting Antibody of Predefined Specificity," Nature 256:495-497.

Kontermann, R.E. (2005) "Recombinant Bispecific Antibodies for Cancer Therapy," Acta. Pharmacol. Sin, (2005) 26(1): 1-9.

Kontermann, R.E. (2012) "Dual Targeting Strategies with Bispecific Antibodies," mAbs, Landes Bioscience 4(2):182-197.

Korman, A.J. et al. (2007) "Checkpoint Blockade in Cancer Immunotherapy," Adv. Immunol. 90:297-339.

Kortt, A.A. et al. (2001) "Dimeric and Trimeric Antibodies: High Avidity Scfvs for Cancer Targeting," Biomol. Eng. 18(3):95-108.

Kranz et al., "Mechanisms of ligand binding by monoclonal anti-fluorescyl antibodies," J. Biol. Chem. 257:6987-6995, 1982.

Kumpel, B.M. Brit. "Human monoclonal anti-D antibodies," J. Haematol. 71:415-420 (1989).

Lagrange, M. et al. (2005) "Binding of Human Papillomavirus 16 E6 to P53 and E6AP Is Impaired by Monoclonal Antibodies Directed Against the Second Zinc-Binding Domain of E6," J. Gen. Virol. 86(Pt4):1001-1007.

Le Gall, F. et al. (Epub May 4, 2004) "Effect of Linker Sequences Between the Antibody Variable Domains On the Formation, Stability and Biological Activity of a Bispecific Tandem Diabody," Protein Eng des Sel. 17(4):357-366.

Le, P.U. et al. (2009) "*Escherichia coli* Expression and Refolding of E-K-Coil-Tagged EGF Generates Fullybioactive EGF for Diverse Applications," Protein Expression and Purification 64:108-117.

Lehmann et al., "Phagocytosis: measurement by flow cytometry," J Immunol Methods. 243(1-2):229-42, 2000.

Lehrnbecher et al., "Variant genotypes of the low-affinity Fcgamma receptors in two control populations and a review of low-affinity Fcgamma receptor polymorphisms in control and disease populations," Blood 94:4220-4232, 1999.

Leland, D.S. and Cinocchio, C.C. (2007) *Role of Cell Culture for Virus Detection in the Age of Technology*, Clin Microbiol Rev 20(1):49-78.

Li et al., "Reconstitution of human Fc gamma RIII cell type specificity in transgenic mice," J Exp Med 183 :1259-1263, 1996.

Li, L. et al. (2010) "Immunotherapy for Prion Diseases: Opportunities and Obstacles," Immunotherapy 2(2):269-282.

Liao, H-X, et al. (2004) "Immunogenicity of Constrained Monoclonal Antibody A32-Human Immunodeficiency Virus (HIV) Env gp120 Complexes Compared to That of Recombinant HIV Type 1 gp120 Envelope Glycoproteins," J. Virology 78(10):5270-5278.

Lindley, P.S. et al. (2009) "The Clinical Utility of Inhibiting CD28-Mediated Costimulation," Immunol. Rev. 229:307-321.

Litowski, J.R. et al. (2002) "Designing Heterodimeric Two-Stranded a-Helical Coiled-Coils: The Effects of Hydrophobicity and a-Helical Propensity On Protein Folding, Stability, And Specificity," J. Biol. Chem. 277:37272-37279.

Liu et al., "Production of a mouse-human chimeric monoclonal antibody to CD20 with potent Fc-dependent biologic activity," J. Immunol, 139:3521-3526, 1987.

LoBuglio, A.F. et al. (1989) "Mouse/Human Chimeric Monoclonal Antibody in Man: Kinetics and Immune Response," Proc. Natl. Acad. Sci. (U.S.A.) 86:4220-4224.

Lonberg, N. et al. (1995) "Human Antibodies from Transgenic Mice," Int. Rev. Immunol 13:65-93.

Lu, D. et al., (2003) "Di-Diabody: a novel tetravalent bispecific antibody molecule by design," J. Immunol. Meth. 279:219-232.

Lu, D. et al. (2004) "The effect of variable domain orientation and arrangement on the antigen-binding activity of a recombinant human bispecific Diabody," BBRC 318: 507-513.

Lu, et al., (2005) "A Fully Human Recombinant IgG-like Bispecific Antibody to Both the Epidermal Growth Factor Receptor and the Insulin-like Growth Factor Receptor for Enhanced Antitumor Activity," The Journal of Biological Chemistiy, vol. 280(20) pp. 19665-19672.

Lum, L.G., et al. (2012) "Targeting Cytomegalovirus-Infected Cells Using T Cells Armed with Anti-CD3 Anti-CMV Bispecific Antibody," Biol. Blood Marrow Transplant 18:1012-1022.

Lund et al., "Expression and characterization of tmncated forms of humanized L243 IgG1. Architectural features can influence synthesis of its oligosaccharide chains and affect superoxide production triggered through human Fcgamma receptor I," Eur J Biochem 267 :7246-57, 2000.

Lund et al., "Human Fc gamma RI and Fc gamma RII interact with distinct but overlapping sites on human IgG," J Immunol 147 :2657-62, 1991.

Lund et al., "Multiple binding sites on the CH2 domain of IgG for mouse Fc gamma R11," Molecular Immunology 29:53-59, 1992.

Lund et al., "Multiple interactions of IgG with its core oligosaccharide can modulate recognition by complement and human Fc gamma receptor I and influence the synthesis of its oligosaccharide chains," J Immunol 157 :4963-4969, 1996.

Lund et al., "Oligosaccharide-protein interactions in IgG can modulate recognition by Fc gamma receptors," FASEB J 9 :115-119, 1995.

Luo et al. (1995) "VL-Linker-VH Orientation-Dependent Expression of Single Chain Fv Containing an Engineered Disulfide-Stabilized Bond in The Framework Regions," J. Biochem. 4(118):825-831.

Maeda, H. et al. (1991) "Construction of Reshaped Human Antibodies with HIV-Neutralizing Activity," Human Antibodies Hybridoma 2:124-134.

Maenaka et al., "The human low affinity Fcgamma receptors IIa, IIb, and III bind IgG with fast kinetics and distinct thermodynamic properties," J Biol Chem 48 :44898-904, 2001.

Mahato, R.I. et al. (1997) "Cationic Lipid-Based Gene Delivery Systems: Pharmaceutical Perspectives," Pharm. Res. 14:853-859.

Mangham, D.C. et al. (1999) "A Novel Immunohistochemical Detection System Using Mirror Image Complementary Antibodies (MICA)," Histopathology 35(2):129-133.

Mariuzza et al., (1987) "The Structural Basis of Antigen-Antibody Recognition," Annual Review of Biophysics and Biophysical Chemistry 16:139-159.

(56) References Cited

OTHER PUBLICATIONS

Marvin et al., "Recombinant approaches to IgG-like bispecific antibodies," Acta Pharmacologica Sinica, 26(6): 649-658, Jun. 2005.

Masiero, S. (2005) "T-cell engineering by a chimeric T-cell receptor with antibody-type specificity for the HIV-1 gp120," Gene Therapy 12, 299-310.

Merrifield, B. (1986) "Solid Phase Synthesis," Science 232(4748):341-347.

Mertens, N. et al., "New Recombinant Bi- and Trispecific Antibody Derivatives," In: Novel Frontiers in the Production of Compounds for Biomedical Use, vol. 1; van Broekhoven, A. et al. (Eds.); Kluwer Academic Publishers, Dordrecht, The Netherlands.

Michaelsen et al., "One disulfide bond in front of the second heavy chain constant region is necessary and sufficient for effector functions of human IgG3 without a genetic hinge," Immunology 91 :9243-9247, 1994.

Moore, P.A. et al., (2011) "Application of Dual Affinity Retargeting Molecules to Achieve Optimal Redirected T-Cell Killing of B-Cell Lymphoma," Blood 117:4542-4551.

Morgan et al., "The N-terminal end of the CH2 domain of chimeric human IgG1 anti-HLA-DR is necessaiy for C1q, Fc gamma RI and Fc gamma RIII binding," Immunology 86 :319-324, 1995.

Morrison et al., "Structural determinants of IgG structure," Immunologist 2 :119-124, 1994.

Mouquet, H. (2012) "Complex-type N-glycan recognition by potent broadly neutralizing HIV antibodies," PNAS 109: E3268-E3277.

Munn et al., "Phagocytosis of tumor cells by human monocytes cultured in recombinant macrophage colony-stimulating factor," J Exp Med. 172(1):231-7, 1990.

Munro, S. et al. (1984) "Use of Peptide Tagging to Detect Proteins Expressed from Cloned Genes: Deletion Mapping Functional Domains of *Drosophila* hsp 70," EMBO J. 3(13):3087-3093.

Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.

Nakamura, T. et al. (1992) "Heterogeneity of Immunoglobulin-Associated Molecules On Human B Cells Identified by Monoclonal Antibodies," Proc. Natl. Acad. Sci. (USA) 89:8522-8526).

Neuberger et al., "Recombinant antibodies possessing novel effector functions," Nature 312 :604-608, 1984.

Norderhaug et al., "Chimeric mouse human IgG3 antibodies with an IgG4-like hinge region induce complement-mediated lysis more efficiently than IgG3 with normal hinge," Eur J Immunol 21:2379-84, 1991.

Nose and Leanderson, "Substitution of asparagine324 with aspartic acid in the Fc portion of mouse antibodies reduces their capacity for C1q binding," Eur J Immunol 19 :2179-81, 1989.

Nossal, G.J. (2011) "Vaccines of The Future," Vaccine 29 Suppl 4: D111-115.

Okazaki et al., "Fucose depletion from human IgG1 oligosaccharide enhances binding enthalpy and association rate between IgG1 and FcgammaRIIIa," J Mol Biol 336 :1239-1249, 2004.

Olafsen et al., "Covalent disulfide-linked anti-CEA Diabody allows site-specific conjugation and radiolabeling for tumor targeting applications," Protein Engineering, Design & Selection, 17(1): 21-27, 2004.

Oleksiewicz, M.B. et al. (Epub Jun. 13, 2012) "Anti-Bacterial Monoclonal Antibodies: Back to The Future?" Arch. Biochem. Biophys. 526(2):124-131.

Orfao and Ruiz-Arguelles, "General concepts about cell sorting techniques," Clinical Biochem. 29:5-9, 1996.

Pack, P. et al. (1992) "Miniantibodies: Use of Amphipathic Helices to Produce Functional, Flexibly Linked Dimeric Fv Fragments with High Avidity in *Escherichia coli*," 31(6):1579-1584.

Partridge et al., "The use of anti-IgG monoclonal antibodies in mapping the monocyte receptor site on IgG," Mol Immunol. 23(12):1365-72, 1986.

Peeters, K. et al. (2001) "Production of Antibodies and Antibody Fragments in Plants," Vaccine 19:2756.

Perussia "Human Natural Killer Cell Protocols" in Methods Molecular Biology, vol. 121 (Campbell et al. eds.) Humana Press Inc., Totowa, NJ. 179-92, 2000.

Phaeton, R. et al. (2010) "Radioimmunotherapy with an Antibody to The HPV16 E6 Oncoprotein Is Effective in an Experimental Cervical Tumor Expressing Low Levels of E6," Cancer Biol. Ther. 10(10):1041-1047.

Pollock, D.P. et al. (1999) "Transgenic Milk as A Method for The Production of Recombinant Antibodies," J. Immunol Methods 231:147-157.

Radaev and Sun, "Recognition of immunoglobulins by Fcgamma receptors," Molecular Immunology 38 :1073-1083, 2001.

Rankin et al. "CD32B, The Human Inhibitory Fc-γ Receptor IIB, As A Target for Monoclonal Antibody Therapy of B-Cell Lymphoma," (2006) Blood 108(7):2384-2391.

Ravetch (1994) "Fc Receptors: Rubor Redux," Cell 78:553-560.

Ravetch and Bolland, "IgG Fc receptors," Annu Rev Immunol 19:275-90, 2001.

Ravetch and Clynes, "Divergent roles for Fc receptors and complement in vivo," Annu Rev Immunol 16:421-432, 1998.

Ravetch and Kinet, "Fc receptors," Annu Rev Immunol 9:457-492, 1991.

Ravetech and Lanier, "Immune inhibitory receptors," Science 290:84-89, 2000.

Redpath et al., "The influence of the hinge region length in binding of human IgG to human Fcgamma receptors," Hum Immunol 59 :720-727, 1998.

Reff et al., "Depletion of B cells in vivo by a chimeric mouse human monoclonal antibody to CD20," Blood 83:435-445, 1994.

Ridgway, J.B. et al. (1996) "'Knobs-Into-Holes' Engineering of Antibody CH3 Domains for Heavy Chain Heterodimerization," Protein Engr, 9:617-621.

Riechmann et al., "Reshaping human antibodies for therapy," Nature. 332(6162):323-7, 1988.

Rosenberg, H.F. et al. (2012) "Inflammatory Responses to Respiratory Syncytial Virus (RSV) Infection and The Development of Immunomodulatory Pharmacotherapeutics," Curr. Med. Chem. 19(10):1424-1431.

Rothlisberger, D. et al. (2005) "Domain Interactions in the Fab Fragment: A Comparative Evaluation of the Single-chain Fv and Fab Format Engineered with Variable Domains of Different Stability," J. Molec. Biol. 347:773-789.

Sarmay et al., "Ligand inhibition studies on the role of Fc receptors in antibody-dependent cell-mediated cytotoxicity," Mol Immunol 21 :43-51, 1984.

Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.

Sarmay et al., "The effect of synthetic peptides corresponding to Fc sequences in human IgG1 on various steps in the B cell activation pathway," Eur J Immunol 18 :289-294, 1988.

Santes-Fridman et al., "Fc gamma receptors: a magic link with the outside world," ASHI Quarterley, 4th Quarter:148-151, 2003.

Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).

Schatz et al., "Use of peptide libraries to map the substrate specificity of a peptide-modifying enzyme: a 13 residue consensus peptide specifies biotinylation in *Escherichia coli*," Bio-Technology 11:1138-1143, 2000.

Sensei et al., "Amino acid differences in the N-terminus of C(H)2 influence the relative abilities of IgG2 and IgG3 to activate complement," Molecular Immunology 34:1019-1029, 1997.

Shadman, K.A. et al. (2011) "A Review of Palivizumab and Emerging Therapies for Respiratory Syncytial Virus," Expert Opin. Biol. Then 11(11):1455-1467.

Shen, R. (2010) "GP41-Specific Antibody Blocks Cell-Free HIV Type 1 Transcytosis Through Human Rectal Mucosa and Model Colonic Epithelium," J. Immunol. 184(7):3648-3655.

(56) References Cited

OTHER PUBLICATIONS

Shields et al., "High resolution mapping of the binding site on human IgG1 for Fc gamma RI, Fc gamma RII, Fc gamma RIII, and FcRn and design of IgG1 variants with improved binding to the Fc Gamma R," J Biol Chem 276 :6591-6604, 2001.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Directed evolution of a stable scaffold for T-cell receptor engineering," Nature Biotechnology 18:754-759, 2000.
Shusta et al., "Increasing the secretory capacity of *Saccharomyces cerevisiae* for production of single-chain antibody fragments," Nature Biotechnology 16:773-777, 1998.
Shusta et al., "Yeast polypeptide fusion surface display levels predict thermal stability and soluble secretion efficiency," J Mol Biol 292:949-956, 1999.
Singer, M. and Berg, P., "Genes and genomes," Moscow, Mir, 1998, vol. 1, pp. 63-64 (Russian and English translation).
Sloan DD, et al. (2015) "Targeting HIV Reservoir in Infected CD4 T Cells by Dual-Affinity Re-targeting Molecules (DARTs) that Bind HIV Envelope and Recruit Cytotoxic T Cells" PLoS Pathog 11(11): e1005233, doi:10.1371/journal.ppat.1005233.
Smith and Morrison, "Recombinant polymeric IgG: an approach to engineering more potent antibodies," Bio-Technology 12:683-688, 1994.
Sondermann and Oosthuizen, "The structure of Fc Receptor-Ig complexes: considerations on stoichiometiy and potential inhibitors," Immunology Letters, 82:51-56, 2002.
Sondermann et al., "Crystal structure of the soluble form of the human fcgamma-receptor IIb: a new member of the immunoglobulin superfamily at 1.7 A resolution," EMBO J 18:1095-1103, 1999.
Sondermann et al., "Molecular basis for immune complex recognition: a comparison of Fc-receptor structures," J. Mol. Biol. 309:737-749, 2001.
Sondermann et al., "The 3.2-A crystal structure of the human IgG1 Fc Fragment-Fc gammaRIII complex," Nature 406:267-273, 2000.
Staerz, U.D. et al. (1985) "Hybrid hybridoma producing a bispecific monoclonal antibody that can focus effector T-cell activity," PNAS 83:1453-1457.
Stavenhagen, J.B. et al. (2007) "Fc Optimization of Therapeutic Antibodies Enhances Their Ability to Kill Tumor Cells in Vitro and Controls Tumor Expansion in Vivo Via Low-Affinity Activating Fcgamma Receptors," Cancer Res. 57(18):8882-8890.
Steinkruger, J.D. et al. (2012) "The d'—d—d' Vertical Triad is Less Discriminating Than the a'—a—a' Vertical Triad in the Antiparallel Coiled-coil Dimer Motif," J. Amer. Chem. Soc. 134(5):2626-2633.
Stephan, J.P. et al. (1999) "Distribution and Function of the Adhesion Molecule BEN During Rat Development," Dev. Biol, 212:264-277.
Stephan, J.P. et al. (1999) "Selective Cloning of Cell Surface Proteins Involved in Organ Development: Epithelial Glycoprotein Is Involved in Normal Epithelial Differentiation," Endocrinology 140:5841-5854.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Stork, R. et al. (2007) "A Novel Tri-Functional Antibody Fusion Protein with Improved Pharmacokinetic Properties Generated by Fusing a Bispecific Single-Chain Diabody with an Albumin-Binding Domain from Streptococcal Protein G," Protein Engineering, Design & Selection 20(11):569-576.
Straussman, R. et al. (2007) "Kinking the Coiled Coil—Negatively Charged Residues at the Coiled-coil Interface," J. Molec. Biol. 366:1232-1242.

Strohmeier et al., "Role of the Fc Gamma R Subclasses Fc gamma RII and Fc gamma RIII in the activation of human neutrophils by low and high valency immune complexes," J Leukocyte Biol 58:415-422, 1995.
Sung, J. (2015) "Dual-Affinity Re-Targeting proteins direct T cell-mediated cytolysis of latently HIV-infected cells," J Clin Invest. 125:4077-4090. doi: 10.1172/JCI82314.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al., "Augmented humoral and anaphylactic responses in Fc gamma RII-deficient mice," Nature 379:346-349, 1996.
Takai et al., "FcR gamma chain deletion results in pleiotrophic effector cell defects," Cell 76 :519-529, 1994.
Takai, "Roles of Fc receptors in autoimmunity," Nature Reviews 2:580-592, 2002.
Takemura, S. et al. (2000) "Construction of a Diabody (Small Recombinant Bispecific Antibody) Using a Refolding System," Protein Eng. 13(8):583-588.
Tamm et al., "The IgG binding site of human FcγRIIIB receptor involves CC' and FG loops of the membrane-proximal domain," J Biol Chem 271:3659-3666, 1996.
Tang, Y. et al. (2001) "Biosynthesis of A Highly Stable Coiled-Coil Protein Containing Hexafluoroleucine in an Engineered Bacterial Host," J. A. Chem. Soc. 123(44): 11089-11090.
Tao et al., "Structural features of human immunoglobulin G that determine isotype-specific differences in complement activation," J Exp Med 178:661-667, 1993.
Tao et al., "The differential ability of human IgG1 and IgG4 to activate complement is determined by the COOH-terminal sequence of the CH2 domain," J Exp Med 173:1025-1028, 1991.
Tempest, P.R. et al. (1991) "Reshaping A Human Monoclonal Antibody to Inhibit Human Respiratory Syncytial Virus Infection in vivo," Bio/Technology 9:266-271.
Ter Meulen, J. (2007) "Monoclonal Antibodies for Prophylaxis and Therapy of Infectious Diseases," Expert Opin. Emerg. Drugs. 12(4):525-540.
Ter Meulen, J. (2011) "Monoclonal Antibodies in Infectious Diseases: Clinical Pipeline in 2011," Infect. Dis. Clin. North Am. 25(4):789-802.
Todorovska, A. et al. (2001) "Design and Application of Diabodies, Triabodies and Tetrabodies for Cancer Targeting," J. Immunol. Methods 248(1-2):47-66.
Trindandapani et al. (2002) "Regulated Expression and Inhibitory Function of FcgammaRIIB in Human Monocytic Cells," J. Biol. Chem. 277(7):5082-5089.
Tripet, B. et al. (2002) "Kinetic Analysis of the Interactions between Troponin C and the C-terminal Troponin I Regulatory Region and Validation of a New Peptide Delivery-Capture System used for Surface Plasmon Resonance," J. Molec. Biol. 323:345-362.
Trkola, A et al. (2005) "Delay of HIV-1 Rebound After Cessation of Antiretroviral Therapy Through Passive Transfer of Human Neutralizing Antibodies," Nat. Med. 11:615-622.
Unkeless, J.C. et al. (1995) "Function of Human Fc Gamma RIIA and Fc Gamma RIIIB," Semin. Immunol. 7(1):37-44.
Van Hest et al. (2001) "Protein-Based Materials, Toward A New Level of Structural Control," Chem. Comm. 19:1897-1904.
Van Sorge et al., "FcgammaR polymorphisms: Implications for function, disease susceptibility and immunotherapy," Tissue Antigens 61:189-202, 2003.
VanAntwerp and Wittrup, "Fine affinity discrimination by yeast surface display and flow cytometry," Biotechnol Prog 16:31-37, 2000.
Vasiliver-Shamis, G. et al. (2008) "Human Immunodeficiency Virus Type 1 Envelope gp120 Induces a Stop Signal and Virological Synapse Formation in Noninfected CD4+ T Cells," J. Virology 82(19):9445-9457.
Verhoeyen, M. et al. (1988) "Reshaping Human Antibodies: Grafting an Antilysozyme Activity," Science 239:1534-1536.
Ver et al. (Epub Mar. 26, 2007) "Monoclonal antibodies capable of discriminating the human inhibitory Fcgamma-receptor IIB (CD32B)

(56) References Cited

OTHER PUBLICATIONS from the activating Fcgamma-receptor IIa (CD32A): biochemical, biological and functional characterization," Immunology 121(3):392-404.
Veri, et al. (Jul. 2010) "Therapeutic Control of B Cell Activation via Recruitment of Fcy Receptor IIb (CD32B) Inhibitory Function with a Novel Bispecific Antibody Scaffold," Arthritis & Rheumatism, vol. 62(7): 1933-1943.
Vidarte, "Serine 132 is the C3 covalent attachment point on the CH1 domain of human IgG1," J Biol Chem 276:38217-38233, 2001.
Viglietta, V. et al. (2007) "Modulating Co-Stimulation," Neurotherapeutics 4:666-675.
Wang, D. et al. (2011) "Palivizumab for Immunoprophylaxis of Respiratory Syncytial Vims (RSV) Bronchiolitis in High-Risk Infants and Young Children: A Systematic Review and Additional Economic Modelling of Subgroup Analyses," Health Technol, Assess. 15(5): iii-iv, 1-124.
Wang, L. et al. (2001) "Expanding The Genetic Code of *Escherichia coli*," Science, 292:498-500.
Wang, L. et al. (2002) "Expanding The Genetic Code," Chem. Comm. 1: 1-11.
Ward and Ghetie, "The effector functions of immunoglobulins: implications for therapy," Therapeutic Immunology 2:77-94, 1995.
Weng and Levy, "Two immunoglobulin G Fragment C receptor polymorphisms independently predict response to rituximab inpatients with follicular lymphoma," J Clin Oncol 21:3940-3947, 2003.
Whaley, K.J. et al. (2011) "Emerging Antibody Products and Nicotiana Manufacturing," Hum. Vaccin, 7(3):349-356.
Wiener, E. et al. "Differences between the activities of human monoclonal IgG1 and IgG3 anti-D antibodies of the Rh blood group system in their abilities to mediate effector functions of monocytes," Immunol. 65:159-163 (1988).
Wing et al., "Mechanism of first-dose cytokine-release syndrome by CAMPATH 1-H: Involvement of CD16 (FcγRIII) and CD11a-CD18 (LFA-1) on NK cells," J Clin Invest 98:2819-2826, 1996.
Wingren et al., "Comparison of surface properties of human IgA, IgE, IgG and IgM antibodies with identical and different specificities," Scand J Immunol 44:430-436, 1996.
Winter, G. et al. (1994) "Making Antibodies by Phage Display Technology," Annu. Rev. Immunol. 12:433-455.
Wittrup, "Protein engineering by cell-surface display," Curr, Opin. Biotechnol. 12:395-399, 2001.
Witrup, "The single cell as a microplate well," Nat Biotechnol 18:1039-1040, 2000.
Wlazlo, A.P. et al. (2001) "Generation and Characterization of Monoclonal Antibodies Against the E6 and E7 Oncoproteins of HPV," Hybridoma 20(4):257-263.
Woof et al., "Localisation of the monocyte-binding region on human immunoglobulin G," Mol Immunol 23:319-330, 1986.
Woolfson, D.N. (2005) "The Design of Coiled-Coil Structures and Assemblies," Adv. Prot. Chem. 70:79-112.
Wu et al., "a novel polymorphism of FcγRIIIa (CD16) alters receptor function and predisposes to autoimmune disease," J Clin Invst 100:1059-1070, 1997.
Wu et al., "Multimerization of a chimeric anti-CD20 single-chain Fv-Fc fusion protein is mediated through variable domain exchange," Protein Engineering 14(2): 1025-1033 (2001).
Wu, A.M et al. (1999) "Designer Genes: Recombinant Antibody Fragments for Biological Imaging," Q. J. Nucl. Med. 44(3):268-283.
Xie, Z. et al. (2005) "A New Format of Bispecific Antibody: Highly Efficient Heterodimerization, Expression and Tumor Cell Lysis," J. Immunol. Methods 296:95-101.
Xiong, D. et al. (2002) "Efficient Inhibition of Human B-Cell Lymphoma Xenografts with an Anti-CD20 x Anti-CD3 Bispecific Diabody," Cancer Lett. (2002) 177(1):29-39.
Xu et al., "Residue at position 331 in the IgG1 and IgG4 CH2 domains contributes to their differential ability to bind and activate complement," J Biol Chem 269:3469-3474, 1994.
Yamada, T. (2011) "Therapeutic Monoclonal Antibodies," Keio J. Med. 60(2):37-46.
Yeung and Wittrup, "Quantitative screening of yeast surface-displayed polypeptide libraries by magnetic bead capture," Biotechnol Prog 18:212-220, 2002.
Yin, S., et al. (2001) "Elimination of Latently HIV-1-Infected Cells by Lymphoblasts Armed with Bifunctional Antibody," Microbiol. Immunol. 45:101-108.
Zeidler et al., "The Fc-region of a new class of intact bispecific antibody mediates activation of accessory cells and NK cells and induces direct phagocytosis of tumour cells," British J Cancer 83:261-266, 2000.
Zeng, Y. et al. (2008) "A Ligand-Pseudoreceptor System Based On de novo Designed Peptides for The Generation of Adenoviral Vectors with Altered Tropism," J, Gene Med. 10:355-367.
Zhu, J. et al. (2013) "Mining the antibodyome for HIV-1-neutralizing antibodies with next-generation sequencing and phylogenetic pairing of heavy/light chains," PNAS 110:6470-6475, doi: 10.1073/pnas. 1219320110.
Zhu, Z. et al. (1997) "Remodeling Domain Interfaces to Enhance Heterodimer Formation," Protein Sci. 6:781-788.
Zuckier et al., "Chimeric human-mouse IgG antibodies with shuffled constant region exons demonstrate that multiple domains contribute to in vivo half-life," Cancer Res 58:3905-3908, 1998.
Shalaby et al. (1992) "*Development of Humanized Bispecific Antibodies Reactive with Cytotoxic Lymphocytes and Tumor Cells Overexpressing the HER2 Protooncogene,*" J. Exp. Med. 175:217-225.

* cited by examiner

SEQUENCE LISTING

<160> NUMBER OF SEQ ID NOS: 53

<210> SEQ ID NO 1
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: OKT3 (Murine Anti-CD3 Antibody) Light Chain
      Variable Region

<400> SEQUENCE: 1

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 2
<211> LENGTH: 192
<212> TYPE: PRT
<213> ORGANISM: Mus musculus
<220> FEATURE:
<221> NAME/KEY: MISC_FEATURE
<223> OTHER INFORMATION: OKT3 (Nurine Anti-CD3 Antibody) Heavy Chain
      Variable Region

<400> SEQUENCE: 2

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
        130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu

```
              165                 170                 175
Gln Ser Asp Leu Tyr Thr Leu Ser Ser Val Thr Val Thr Ser Ser
        180                 185                 190

<210> SEQ ID NO 3
<211> LENGTH: 106
<212> TYPE: PRT
<213> ORGANISM: Artificial Sequence
<220> FEATURE:
<223> OTHER INFORMATION: M291 (Humanized Anti-CD3 Antibody) Light Chain
      Variable Region

<400> SEQUENCE: 3

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Thr Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Asp Thr Tyr Tyr Cys Gln Gln Trp Ser Ser Asn Pro Pro Thr
                85                  90                  95

Phe Gly Ser Gly Thr Lys Leu Glu Ile Lys
            100                 105

<210> SEQ ID NO 4
<211> LENGTH: 120
<212> TYPE: PRT
<213> ORGANISM: Artificial Sequence
<220> FEATURE:
<223> OTHER INFORMATION: M291 (Humanized Anti-CD3 Antibody) Heavy Chain
      Variable Region

<400> SEQUENCE: 4

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Ile Ser Tyr
            20                  25                  30

Thr Met His Trp Val Lys Gln Arg Pro Gly Gln Gly Leu Glu Trp Ile
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ser Ser Ser Ala Tyr
65                  70                  75                  80

Met Gln Leu Ser Ser Leu Thr Ser Glu Asp Ser Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ala
        115                 120

<210> SEQ ID NO 5
<211> LENGTH: 130
<212> TYPE: PRT
<213> ORGANISM: Rattus norvegicus
<220> FEATURE:
<221> NAME/KEY: MISC_FEATURE
```

```
<222> LOCATION: (1)..(130)
<223> OTHER INFORMATION: YTH12.5 (Rat Anti-CD3 Antibody) Light Chain
      Variable Region

<400> SEQUENCE: 5

Met Gly Trp Ser Cys Ile Ile Leu Phe Leu Val Ala Thr Ala Thr Gly
1               5                   10                  15

Val His Ser Asp Ile Gln Leu Thr Gln Pro Asn Ser Val Ser Thr Ser
                20                  25                  30

Leu Gly Ser Thr Val Lys Leu Ser Cys Thr Leu Ser Ser Gly Asn Ile
            35                  40                  45

Glu Asn Asn Tyr Val His Trp Tyr Gln Leu Tyr Glu Gly Arg Ser Pro
50                  55                  60

Thr Thr Met Ile Tyr Asp Asp Asp Lys Arg Pro Asp Gly Val Pro Asp
65                  70                  75                  80

Arg Phe Ser Gly Ser Ile Asp Arg Ser Ser Asn Ser Ala Phe Leu Thr
                85                  90                  95

Ile His Asn Val Ala Ile Glu Asp Glu Ala Ile Tyr Phe Cys His Ser
            100                 105                 110

Tyr Val Ser Ser Phe Asn Val Phe Gly Gly Gly Thr Lys Leu Thr Val
        115                 120                 125

Leu Arg
    130

<210> SEQ ID NO 6
<211> LENGTH: 138
<212> TYPE: PRT
<213> ORGANISM: Mus musculus
<220> FEATURE:
<221> NAME/KEY: MISC_FEATURE
<222> LOCATION: (1)..(138)
<223> OTHER INFORMATION: XR31(Muriine Anti-CD3 Antibody) Heavy Chain
      Variable Region

<400> SEQUENCE: 6

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Phe Pro Met Ala Trp Val Arg Gln Ala Pro Gly Lys Gly Leu
50                  55                  60

Glu Trp Val Ser Thr Ile Ser Thr Ser Gly Gly Arg Thr Tyr Tyr Arg
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Phe Arg Gln Tyr Ser Gly Gly Phe Asp Tyr Trp
        115                 120                 125

Gly Gln Gly Thr Leu Val Thr Val Ser Ser
    130                 135

<210> SEQ ID NO 7
<211> LENGTH: 107
<212> TYPE: PRT
<213> ORGANISM: Mus musculus
<220> FEATURE:
```

```
<221> NAME/KEY: MISC_FEATURE
<222> LOCATION: (1)..(107)
<223> OTHER INFORMATION: Murine Anti-CD3 Antibody 1 Light Chain Variable
      Region

<400> SEQUENCE: 7
```

Gln Val Val Leu Thr Gln Ser Pro Ala Ile Met Ser Ala Phe Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Arg Asn Pro Pro Thr
                85                  90                  95

Phe Gly Gly Gly Thr Lys Leu Gln Ile Thr Arg
            100                 105

```
<210> SEQ ID NO 8
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: Murine Anti-CD3 Antibody 1 Heavy Chain Variable
      Region

<400> SEQUENCE: 8
```

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ser
        115                 120

```
<210> SEQ ID NO 9
<211> LENGTH: 110
<212> TYPE: PRT
<213> ORGANISM: Mus musculus
<220> FEATURE:
<221> NAME/KEY: misc_feature
<222> LOCATION: (1)..(110)
<223> OTHER INFORMATION: Murine Anti-CD3 Antibody 2 Light Chain Variable
      Region

<400> SEQUENCE: 9
```

Gln Ala Val Val Thr Gln Glu Ser Ala Leu Thr Thr Ser Pro Gly Glu

```
                1               5                   10                  15
            Thr Val Thr Leu Thr Cys Arg Ser Ser Thr Gly Ala Val Thr Thr Ser
                            20                  25                  30

Asn Tyr Ala Asn Trp Val Gln Glu Lys Pro Asp His Leu Phe Thr Gly
                        35                  40                  45

Leu Ile Gly Gly Thr Asn Lys Arg Ala Pro Gly Val Pro Ala Arg Phe
                50                  55                  60

Ser Gly Ser Leu Ile Gly Asp Lys Ala Ala Leu Thr Ile Thr Gly Ala
             65                 70                  75                  80

Gln Thr Glu Asp Glu Ala Ile Tyr Phe Cys Ala Leu Trp Tyr Ser Asn
                            85                  90                  95

Leu Trp Val Phe Gly Gly Gly Thr Lys Leu Thr Val Leu Gly
                        100                 105                 110

<210> SEQ ID NO 10
<211> LENGTH: 125
<212> TYPE: PRT
<213> ORGANISM: Mus musculus
<220> FEATURE:
<221> NAME/KEY: misc_feature
<222> LOCATION: (1)..(125)
<223> OTHER INFORMATION: Murine Anti-CD3 Antibody 2 Heavy Chain Variable
      Region

<400> SEQUENCE: 10

Glu Val Gln Leu Val Glu Ser Gly Gly Gly Leu Val Gln Pro Lys Gly
             1               5                   10                  15

Ser Leu Lys Leu Ser Cys Ala Ala Ser Gly Phe Thr Phe Asn Thr Tyr
                            20                  25                  30

Ala Met Asn Trp Val Arg Gln Ala Pro Gly Lys Gly Leu Glu Trp Val
                        35                  40                  45

Ala Arg Ile Arg Ser Lys Tyr Asn Asn Tyr Ala Thr Tyr Tyr Ala Asp
                50                  55                  60

Ser Val Lys Asp Arg Phe Thr Ile Ser Arg Asp Asp Ser Gln Ser Ile
             65                 70                  75                  80

Leu Tyr Leu Gln Met Asn Asn Leu Lys Thr Glu Asp Thr Ala Met Tyr
                            85                  90                  95

Tyr Cys Val Arg His Gly Asn Phe Gly Asn Ser Tyr Val Ser Trp Phe
                        100                 105                 110

Ala Tyr Trp Gly Gln Gly Thr Leu Val Thr Val Ser Ala
                        115                 120             125

<210> SEQ ID NO 11
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: BMA031 Anti-TCR Antibody Light Chain Variable
      Region

<400> SEQUENCE: 11

Gln Ile Val Leu Thr Gln Ser Pro Ala Ile Met Ser Ala Ser Pro Gly
             1               5                   10                  15

Glu Lys Val Thr Met Thr Cys Ser Ala Thr Ser Ser Val Ser Tyr Met
                            20                  25                  30

His Trp Tyr Gln Gln Lys Ser Gly Thr Ser Pro Lys Arg Trp Ile Tyr
                        35                  40                  45
```

```
Asp Thr Ser Lys Leu Ala Ser Gly Val Pro Ala Arg Phe Ser Gly Ser
        50                  55                  60
Gly Ser Gly Thr Ser Tyr Ser Leu Thr Ile Ser Ser Met Glu Ala Glu
 65                  70                  75                  80
Asp Ala Ala Thr Tyr Tyr Cys Gln Gln Trp Ser Ser Asn Pro Leu Thr
                85                  90                  95
Phe Gly Ala Gly Thr Lys Leu Glu Leu Lys
            100                 105
```

<210> SEQ ID NO 12
<211> LENGTH: 120
<212> TYPE: PRT
<213> ORGANISM: Mus musculus
<220> FEATURE:
<221> NAME/KEY: misc_feature
<222> LOCATION: (1)..(120)
<223> OTHER INFORMATION: BMA031 Anti-TCR Antibody Heavy Chain Variable
      Region

<400> SEQUENCE: 12

```
Glu Val Gln Leu Gln Gln Ser Gly Pro Glu Leu Val Lys Pro Gly Ala
 1               5                  10                  15
Ser Val Lys Met Ser Cys Lys Ala Ser Gly Tyr Lys Phe Thr Ser Tyr
            20                  25                  30
Val Met His Trp Val Lys Gln Lys Pro Gly Gln Gly Leu Glu Trp Ile
        35                  40                  45
Gly Tyr Ile Asn Pro Tyr Asn Asp Val Thr Lys Tyr Asn Glu Lys Phe
    50                  55                  60
Lys Gly Lys Ala Thr Leu Thr Ser Asp Lys Ser Ser Thr Ala Tyr
 65                  70                  75                  80
Met Glu Leu Ser Ser Leu Thr Ser Glu Asp Ser Ala Val His Tyr Cys
                85                  90                  95
Ala Arg Gly Ser Tyr Tyr Asp Tyr Asp Gly Phe Val Tyr Trp Gly Gln
            100                 105                 110
Gly Thr Leu Val Thr Val Ser Ala
        115                 120
```

<210> SEQ ID NO 13
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: TRX2 Anti-CD8 Antibody Light Chain Variable
      Region

<400> SEQUENCE: 13

```
Asp Ile Gln Met Thr Gln Ser Pro Ser Ser Leu Ser Ala Ser Val Gly
 1               5                  10                  15
Asp Arg Val Thr Ile Thr Cys Lys Gly Ser Gln Asp Ile Asn Asn Tyr
            20                  25                  30
Leu Ala Trp Tyr Gln Gln Lys Pro Gly Lys Ala Pro Lys Leu Leu Ile
        35                  40                  45
Tyr Asn Thr Asp Ile Leu His Thr Gly Val Pro Ser Arg Phe Ser Gly
    50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Tyr Gln Tyr Asn Asn Gly Tyr Thr
                85                  90                  95
```

```
Phe Gly Gln Gly Thr Lys Val Glu Ile Lys
        100                 105

<210> SEQ ID NO 14
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: TRX2 Anti-CD8 Antibody Heavy Chain Variable
      Region

<400> SEQUENCE: 14

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Phe
                20                  25                  30

Gly Met Asn Trp Val Arg Gln Ala Pro Gly Lys Gly Leu Glu Trp Val
            35                  40                  45

Ala Leu Ile Tyr Tyr Asp Gly Ser Asn Lys Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ser
        115                 120

<210> SEQ ID NO 15
<211> LENGTH: 112
<212> TYPE: PRT
<213> ORGANISM: Mus musculus
<220> FEATURE:
<221> NAME/KEY: misc_feature
<222> LOCATION: (1)..(112)
<223> OTHER INFORMATION: TRX1 Anti-CD4 Antibody Light Chain Variable
      Domain

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Val Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Leu
                85                  90                  95

Gln Asp Pro Pro Thr Phe Gly Gly Gly Thr Lys Val Glu Ile Lys Arg
            100                 105                 110

<210> SEQ ID NO 16
<211> LENGTH: 118
<212> TYPE: PRT
```

<213> ORGANISM: Mus musculus
<220> FEATURE:
<221> NAME/KEY: MISC_FEATURE
<222> LOCATION: (1)..(118)
<223> OTHER INFORMATION: TRX1 Anti-CD4 Antibody Heavy Chain Variable
      Domain

<400> SEQUENCE: 16

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ala Tyr
                20                  25                  30

Val Ile Ser Trp Val Arg Gln Ala Pro Gly Gln Gly Leu Glu Trp Met
            35                  40                  45

Gly Glu Ile Tyr Pro Gly Ser Gly Ser Tyr Asn Glu Lys Phe
        50                  55                  60

Lys Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Asp Gly Ser Arg Phe Val Tyr Trp Gly Gln Gly Thr
            100                 105                 110

Leu Val Thr Val Ser Ser
        115

<210> SEQ ID NO 17
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Lo-CD2a Anti-CD2a Antibody Light Chain Variable
      Region

<400> SEQUENCE: 17

Asp Val Val Leu Thr Gln Thr Pro Pro Thr Leu Leu Ala Thr Ile Gly
1               5                   10                  15

Gln Ser Val Ser Ile Ser Cys Arg Ser Ser Gln Ser Leu Leu His Ser
                20                  25                  30

Ser Gly Asn Thr Tyr Leu Asn Trp Leu Leu Gln Arg Thr Gly Gln Ser
            35                  40                  45

Pro Gln Pro Leu Ile Tyr Leu Val Ser Lys Leu Glu Ser Gly Val Pro
        50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Met Gln Phe
                85                  90                  95

Thr His Tyr Pro Tyr Thr Phe Gly Ala Gly Thr Lys Leu Glu Leu Lys
            100                 105                 110

<210> SEQ ID NO 18
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Lo-CD2a Anti-CD2a Antibody Heavy Chain Variable
      Region

<400> SEQUENCE: 18

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Ile Phe Thr Glu Tyr
            20                  25                  30

Tyr Met Tyr Trp Val Lys Gln Arg Pro Lys Gln Gly Leu Glu Leu Val
        35                  40                  45

Gly Arg Ile Asp Pro Glu Asp Gly Ser Ile Asp Tyr Val Glu Lys Phe
    50                  55                  60

Lys Lys Lys Ala Thr Leu Thr Ala Asp Thr Ser Ser Asn Thr Ala Tyr
65              70                  75                  80

Met Gln Leu Ser Ser Leu Thr Ser Glu Asp Thr Ala Thr Tyr Phe Cys
                85                  90                  95

Ala Arg Gly Lys Phe Asn Tyr Arg Phe Ala Tyr Trp Gly Gln Gly Thr
            100                 105                 110

Leu Val Thr Val Ser Ser
            115

<210> SEQ ID NO 19
<211> LENGTH: 111
<212> TYPE: PRT
<213> ORGANISM: Mus musculus
<220> FEATURE:
<221> NAME/KEY: misc_feature
<222> LOCATION: (1)..(111)
<223> OTHER INFORMATION: 3G8 Anti-CD16 Antibody Light Chain Variable
      Region

<400> SEQUENCE: 19

Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65              70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 20
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: 3G8 Anti-CD16 Antibody Heavy Chain Variable
      Region

<400> SEQUENCE: 20

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu

```
                35                  40                  45
Trp Leu Ala His Ile Trp Trp Asp Asp Lys Arg Tyr Asn Pro Ala
         50                  55                  60
Leu Lys Ser Arg Leu Thr Ile Ser Lys Asp Thr Ser Ser Asn Gln Val
 65                  70                  75                  80
Phe Leu Lys Ile Ala Ser Val Asp Thr Ala Asp Thr Ala Thr Tyr Tyr
                 85                  90                  95
Cys Ala Gln Ile Asn Pro Ala Trp Phe Ala Tyr Trp Gly Gln Gly Thr
            100                 105                 110
Leu Val Thr Val Ser Ala
        115
```

<210> SEQ ID NO 21
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: A9 Anti-CD16 Antibody Light Chain Variable
      Region

<400> SEQUENCE: 21

```
Asp Ile Gln Ala Val Val Thr Gln Glu Ser Ala Leu Thr Thr Ser Pro
 1               5                  10                  15
Gly Glu Thr Val Thr Leu Thr Cys Arg Ser Asn Thr Gly Thr Val Thr
                 20                  25                  30
Thr Ser Asn Tyr Ala Asn Trp Val Gln Glu Lys Pro Asp His Leu Phe
             35                  40                  45
Thr Gly Leu Ile Gly His Thr Asn Asn Arg Ala Pro Gly Val Pro Ala
         50                  55                  60
Arg Phe Ser Gly Ser Leu Ile Gly Asp Lys Ala Ala Leu Thr Ile Thr
 65                  70                  75                  80
Gly Ala Gln Thr Glu Asp Glu Ala Ile Tyr Phe Cys Ala Leu Trp Tyr
                 85                  90                  95
Asn Asn His Trp Val Phe Gly Gly Gly Thr Lys Leu Thr Val Leu
            100                 105                 110
```

<210> SEQ ID NO 22
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: A9 Anti-CD16 Antibody Heavy Chain Variable
      Region

<400> SEQUENCE: 22

```
Gln Val Gln Leu Gln Gln Ser Gly Ala Glu Leu Val Arg Pro Gly Thr
 1               5                  10                  15
Ser Val Lys Ile Ser Cys Lys Ala Ser Gly Tyr Thr Phe Thr Asn Tyr
                 20                  25                  30
Trp Leu Gly Trp Val Lys Gln Arg Pro Gly His Gly Leu Glu Trp Ile
             35                  40                  45
Gly Asp Ile Tyr Pro Gly Gly Gly Tyr Thr Asn Tyr Asn Glu Lys Phe
         50                  55                  60
Lys Gly Lys Ala Thr Val Thr Ala Asp Thr Ser Ser Arg Thr Ala Tyr
 65                  70                  75                  80
```

-continued

```
Val Gln Val Arg Ser Leu Thr Ser Glu Asp Ser Ala Val Tyr Phe Cys
            85                  90                  95

Ala Arg Ser Ala Ser Trp Tyr Phe Asp Val Trp Gly Ala Arg Thr Thr
        100                 105                 110

Val Thr Val Ser Ser
        115
```

<210> SEQ ID NO 23
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: KYK 1.0 Anti-NKG2D Antibody Light Chain
      Variable Region

<400> SEQUENCE: 23

```
Gln Pro Val Leu Thr Gln Pro Ser Ser Val Ser Val Ala Pro Gly Glu
1               5                   10                  15

Thr Ala Arg Ile Pro Cys Gly Gly Asp Asp Ile Glu Thr Lys Ser Val
            20                  25                  30

His Trp Tyr Gln Gln Lys Pro Gly Gln Ala Pro Val Leu Val Ile Tyr
        35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asn Asn Asp Glu
                85                  90                  95

Trp Val Phe Gly Gly Gly Thr Gln Leu Thr Val Leu
        100                 105
```

<210> SEQ ID NO 24
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: KYK 1.0 Anti-NKG2D Antibody Heavy Chain
      Variable Region

<400> SEQUENCE: 24

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Lys Tyr
65                  70                  75                  80

Leu Gln Met Asn Ser Leu Arg Ala Glu Asp Thr Ala Val Tyr Tyr Cys
                85                  90                  95

Ala Lys Asp Arg Phe Gly Tyr Tyr Leu Asp Tyr Trp Gly Gln Gly Thr
        100                 105                 110

Leu Val Thr Val Ser Ser
        115
```

<210> SEQ ID NO 25
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: KYK 2.0 Anti-NKG2D Antibody Light Chain
      Variable Region

<400> SEQUENCE: 25

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
        50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 26
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: KYK 2.0 Anti-NKG2D Antibody Heavy Chain
      Variable Region

<400> SEQUENCE: 26

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120

<210> SEQ ID NO 27
<211> LENGTH: 8
<212> TYPE: PRT
<213> ORGANISM: Artificial Sequence
<220> FEATURE:
<223> OTHER INFORMATION: Peptide Linker

<400> SEQUENCE: 27

Gly Gly Gly Ser Gly Gly Gly Gly
1               5

<210> SEQ ID NO 28
<211> LENGTH: 24
<212> TYPE: DNA
<213> ORGANISM: Artificial Sequence
<220> FEATURE:
<223> OTHER INFORMATION: Polynucleotide Encoding Peptide Linker GGGSGGGG

<400> SEQUENCE: 28
ggaggcggat ccggaggcgg aggc                                              24

<210> SEQ ID NO 29
<211> LENGTH: 4
<212> TYPE: PRT
<213> ORGANISM: Artificial Sequence
<220> FEATURE:
<223> OTHER INFORMATION: Cysteine-Containing Peptide

<400> SEQUENCE: 29

Leu Gly Gly Cys
1

<210> SEQ ID NO 30
<211> LENGTH: 13
<212> TYPE: PRT
<213> ORGANISM: Artificial Sequence
<220> FEATURE:
<223> OTHER INFORMATION: Cysteine-Containing Hinge Domain

<400> SEQUENCE: 30

Glu Pro Lys Ser Cys Asp Lys Thr His Thr Cys Pro Pro
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Cysteine-Containing Hinge Domain

<400> SEQUENCE: 31

Glu Ser Lys Tyr Gly Pro Pro Cys Pro Ser
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Cysteine-Containing Peptide

<400> SEQUENCE: 32

Val Glu Pro Lys Ser Cys
1               5

<210> SEQ ID NO 33
<211> LENGTH: 18
<212> TYPE: DNA
<213> ORGANISM: Artificial Sequence
<220> FEATURE:
<223> OTHER INFORMATION: Polynucleotide Encoding Cysteine-Containing
      Peptide VEPKSC

```
<400> SEQUENCE: 33
gttgagccca aatcttgt                                              18

<210> SEQ ID NO 34
<211> LENGTH: 10
<212> TYPE: PRT
<213> ORGANISM: Artificial Sequence
<220> FEATURE:
<223> OTHER INFORMATION: Cysteine-Containing Peptide

<400> SEQUENCE: 34

Leu Gly Gly Cys Phe Asn Arg Gly Glu Cys
1               5                   10

<210> SEQ ID NO 35
<211> LENGTH: 30
<212> TYPE: DNA
<213> ORGANISM: Artificial Sequence
<220> FEATURE:
<223> OTHER INFORMATION: Polynucleotide Encoding Cysteine-Containing
      Peptide LGGCFNRGEC

<400> SEQUENCE: 35
ctgggaggct gcttcaacag gggagagtgt                                 30

<210> SEQ ID NO 36
<211> LENGTH: 6
<212> TYPE: PRT
<213> ORGANISM: Artificial Sequence
<220> FEATURE:
<223> OTHER INFORMATION: Cysteine-Containing Peptide

<400> SEQUENCE: 36

Phe Asn Arg Gly Glu Cys
1               5

<210> SEQ ID NO 37
<211> LENGTH: 18
<212> TYPE: DNA
<213> ORGANISM: Artificial Sequence
<220> FEATURE:
<223> OTHER INFORMATION: Polynucleotide Encoding Cysteine-Containing
      Peptide FNRGEC

<400> SEQUENCE: 37
ttcaacaggg gagagtgt                                              18

<210> SEQ ID NO 38
<211> LENGTH: 6
<212> TYPE: PRT
<213> ORGANISM: Artificial Sequence
<220> FEATURE:
<223> OTHER INFORMATION: Cysteine-Containing Peptide

<400> SEQUENCE: 38

Gly Gly Cys Gly Gly Gly
1               5

<210> SEQ ID NO 39
<211> LENGTH: 28
<212> TYPE: PRT
<213> ORGANISM: Artificial Sequence
<220> FEATURE:
<223> OTHER INFORMATION: E Coil

<400> SEQUENCE: 39
```

-continued

```
Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 40
<211> LENGTH: 28
<212> TYPE: PRT
<213> ORGANISM: Artificial Sequence
<220> FEATURE:
<223> OTHER INFORMATION: K Coil

<400> SEQUENCE: 40

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 41
<211> LENGTH: 5
<212> TYPE: PRT
<213> ORGANISM: Artificial Sequence
<220> FEATURE:
<223> OTHER INFORMATION: Peptide Linker

<400> SEQUENCE: 41

Gly Gly Gly Asn Ser
1               5

<210> SEQ ID NO 42
<211> LENGTH: 273
<212> TYPE: PRT
<213> ORGANISM: Artificial Sequence
<220> FEATURE:
<223> OTHER INFORMATION: First Polypeptide Chain of Anti-HIV env
      Antibody 7B2 x Anti-CD16 Antibody h3G8 Bispecific Diabody

<400> SEQUENCE: 42

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gln Val Thr Leu Arg Glu Ser
        115                 120                 125

Gly Pro Ala Leu Val Lys Pro Thr Gln Thr Leu Thr Leu Thr Cys Thr
    130                 135                 140

Phe Ser Gly Phe Ser Leu Ser Thr Ser Gly Met Gly Val Gly Trp Ile
145                 150                 155                 160

Arg Gln Pro Pro Gly Lys Ala Leu Glu Trp Leu Ala His Ile Trp Trp
                165                 170                 175
```

Asp Asp Asp Lys Arg Tyr Asn Pro Ala Leu Lys Ser Arg Leu Thr Ile
            180                 185                 190

Ser Lys Asp Thr Ser Lys Asn Gln Val Val Leu Thr Met Thr Asn Met
        195                 200                 205

Asp Pro Val Asp Thr Ala Thr Tyr Tyr Cys Ala Gln Ile Asn Pro Ala
    210                 215                 220

Trp Phe Ala Tyr Trp Gly Gln Gly Thr Leu Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys

<210> SEQ ID NO 43
<211> LENGTH: 279
<212> TYPE: PRT
<213> ORGANISM: Artificial Sequence
<220> FEATURE:
<223> OTHER INFORMATION: Second Polypeptide Chain of Anti-HIV env
      Antibody 7B2 x Anti-CD16 Antibody h3G8 Bispecific Diabody

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Val Gln Ser Gly Gly
        115                 120                 125

Gly Val Phe Lys Pro Gly Gly Ser Leu Arg Leu Ser Cys Glu Ala Ser
    130                 135                 140

Gly Phe Thr Phe Thr Glu Tyr Tyr Met Thr Trp Val Arg Gln Ala Pro
145                 150                 155                 160

Gly Lys Gly Leu Glu Trp Leu Ala Tyr Ile Ser Lys Asn Gly Glu Tyr
                165                 170                 175

Ser Lys Tyr Ser Pro Ser Ser Asn Gly Arg Phe Thr Ile Ser Arg Asp
            180                 185                 190

Asn Ala Lys Asn Ser Val Phe Leu Gln Leu Asp Arg Leu Ser Ala Asp
        195                 200                 205

Asp Thr Ala Val Tyr Tyr Cys Ala Arg Ala Asp Gly Leu Thr Tyr Phe
    210                 215                 220

Ser Glu Leu Leu Gln Tyr Ile Phe Asp Leu Trp Gly Gln Gly Ala Arg
225                 230                 235                 240

Val Thr Val Ser Ser Gly Gly Cys Gly Gly Gly Lys Val Ala Ala Leu
                245                 250                 255

Lys Glu Lys Val Ala Ala Leu Lys Glu Val Ala Ala Leu Lys Glu
            260                 265                 270

Lys Val Ala Ala Leu Lys Glu
        275

<210> SEQ ID NO 44
<211> LENGTH: 276
<212> TYPE: PRT
<213> ORGANISM: Artificial Sequence
<220> FEATURE:
<223> OTHER INFORMATION: First Polypeptide Chain of Anti-Fluorescein
      Antibody 4-4-20 x Anti-CD16 Antibody h3G8 Bispecific Diabody

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Glu Val Lys Leu Asp Glu Thr Gly Gly
        115                 120                 125

Gly Leu Val Gln Pro Gly Arg Pro Met Lys Leu Ser Cys Val Ala Ser
    130                 135                 140

Gly Phe Thr Phe Ser Asp Tyr Trp Met Asn Trp Val Arg Gln Ser Pro
145                 150                 155                 160

Glu Lys Gly Leu Glu Trp Val Ala Gln Ile Arg Asn Lys Pro Tyr Asn
                165                 170                 175

Tyr Glu Thr Tyr Tyr Ser Asp Ser Val Lys Gly Arg Phe Thr Ile Ser
            180                 185                 190

Arg Asp Asp Ser Lys Ser Ser Val Tyr Leu Gln Met Asn Asn Leu Arg
        195                 200                 205

Val Glu Asp Met Gly Ile Tyr Tyr Cys Thr Gly Ser Tyr Tyr Gly Met
    210                 215                 220

Asp Tyr Trp Gly Gln Gly Thr Ser Val Thr Val Ser Ser Gly Gly Cys
225                 230                 235                 240

Gly Gly Gly Glu Val Ala Ala Leu Glu Lys Glu Val Ala Ala Leu Glu
                245                 250                 255

Lys Glu Val Ala Ala Leu Glu Lys Glu Val Ala Ala Leu Glu Lys Gly
            260                 265                 270

Gly Gly Asn Ser
        275

<210> SEQ ID NO 45
<211> LENGTH: 294
<212> TYPE: PRT
<213> ORGANISM: Artificial Sequence
<220> FEATURE:
<223> OTHER INFORMATION: Second Polypeptide Chain of Anti-Fluorescein
      Antibody 4-4-20 x Anti-CD16 Antibody h3G8 Bispecific Diabody

<400> SEQUENCE: 45

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gln Val Thr Leu Arg Glu Ser Gly
        115                 120                 125

Pro Ala Leu Val Lys Pro Thr Gln Thr Leu Thr Leu Thr Cys Thr Phe
    130                 135                 140

Ser Gly Phe Ser Leu Ser Thr Ser Gly Met Gly Val Gly Trp Ile Arg
145                 150                 155                 160

Gln Pro Pro Gly Lys Ala Leu Glu Trp Leu Ala His Ile Trp Trp Asp
                165                 170                 175

Asp Asp Lys Arg Tyr Asn Pro Ala Leu Lys Ser Arg Leu Thr Ile Ser
            180                 185                 190

Lys Asp Thr Ser Lys Asn Gln Val Val Leu Thr Met Thr Asn Met Asp
        195                 200                 205

Pro Val Asp Thr Ala Thr Tyr Tyr Cys Ala Gln Ile Asn Pro Ala Trp
    210                 215                 220

Phe Ala Tyr Trp Gly Gln Gly Thr Leu Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270

Gly Gly Gly Asn Ser Gly Gly Asp Tyr Lys Asp Asp Asp Lys
        275                 280                 285

Gly Gly Gly Ser Asn Ser
    290

<210> SEQ ID NO 46
<211> LENGTH: 277
<212> TYPE: PRT
<213> ORGANISM: Artificial Sequence
<220> FEATURE:
<223> OTHER INFORMATION: First Polypeptide Chain of Anti-HIV gp120
      Antibody A32 x Anti-CD3 Antibody 2 Bispecific Diabody

<400> SEQUENCE: 46

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
            50                  55                  60

Ser Gly Ser Lys Ser Gly Asn Thr Ala Ser Leu Thr Val Ser Gly Leu
 65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
    210                 215                 220

Ser Tyr Val Ser Trp Phe Ala Tyr Trp Gly Gln Gly Thr Leu Val Thr
225                 230                 235                 240

Val Ser Ser Gly Gly Cys Gly Gly Glu Val Ala Ala Leu Glu Lys
                245                 250                 255

Glu Val Ala Ala Leu Glu Lys Glu Val Ala Ala Leu Glu Lys Glu Val
        260                 265                 270

Ala Ala Leu Glu Lys
        275

<210> SEQ ID NO 47
<211> LENGTH: 275
<212> TYPE: PRT
<213> ORGANISM: Artificial Sequence
<220> FEATURE:
<223> OTHER INFORMATION: Second Polypeptide Chain of Anti-HIV gp120
      Antibody A32 x Anti-CD3 Antibody 2 Bispecific Diabody

<400> SEQUENCE: 47

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Gln Glu Ser Gly Pro Gly

```
            115                 120                 125
Leu Val Lys Pro Ser Gln Thr Leu Ser Leu Ser Cys Thr Val Ser Gly
        130                 135                 140

Gly Ser Ser Ser Ser Gly Ala His Tyr Trp Ser Trp Ile Arg Gln Tyr
145                 150                 155                 160

Pro Gly Lys Gly Leu Glu Trp Ile Gly Tyr Ile His Tyr Ser Gly Asn
                165                 170                 175

Thr Tyr Tyr Asn Pro Ser Leu Lys Ser Arg Ile Thr Ile Ser Gln His
            180                 185                 190

Thr Ser Glu Asn Gln Phe Ser Leu Lys Leu Asn Ser Val Thr Val Ala
        195                 200                 205

Asp Thr Ala Val Tyr Tyr Cys Ala Arg Gly Thr Arg Leu Arg Thr Leu
    210                 215                 220

Arg Asn Ala Phe Asp Ile Trp Gly Gln Gly Thr Leu Val Thr Val Ser
225                 230                 235                 240

Ser Gly Gly Cys Gly Gly Gly Lys Val Ala Ala Leu Lys Glu Lys Val
                245                 250                 255

Ala Ala Leu Lys Glu Lys Val Ala Ala Leu Lys Glu Lys Val Ala Ala
            260                 265                 270

Leu Lys Glu
        275

<210> SEQ ID NO 48
<211> LENGTH: 280
<212> TYPE: PRT
<213> ORGANISM: Artificial Sequence
<220> FEATURE:
<223> OTHER INFORMATION: First Polypeptide Chain of Anti-HIV env
      Antibody 7B2 x Anti-CD3 Antibody 2 Bispecific Diabody

<400> SEQUENCE: 48

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser His Pro Pro Thr Phe Gly His Gly Thr Arg Val Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Gly Arg Phe Thr
            180                 185                 190
```

Ile Ser Arg Asp Asp Ser Lys Asn Ser Leu Tyr Leu Gln Met Asn Ser
            195                 200                 205

Leu Lys Thr Glu Asp Thr Ala Val Tyr Tyr Cys Val Arg His Gly Asn
        210                 215                 220

Phe Gly Asn Ser Tyr Val Ser Trp Phe Ala Tyr Trp Gly Gln Gly Thr
225                 230                 235                 240

Leu Val Thr Val Ser Ser Gly Cys Gly Gly Glu Val Ala Ala
                245                 250                 255

Leu Glu Lys Glu Val Ala Ala Leu Lys Glu Val Ala Ala Leu Glu
            260                 265                 270

Lys Glu Val Ala Ala Leu Glu Lys
            275                 280

<210> SEQ ID NO 49
<211> LENGTH: 278
<212> TYPE: PRT
<213> ORGANISM: Artificial Sequence
<220> FEATURE:
<223> OTHER INFORMATION: Second Polypeptide Chain of Anti-HIV env
      Antibody 7B2 x Anti-CD3 Antibody 2 Bispecific Diabody

<400> SEQUENCE: 49

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Gly Gly
        115                 120                 125

Val Phe Lys Pro Gly Gly Ser Leu Arg Leu Ser Cys Glu Ala Ser Gly
    130                 135                 140

Phe Thr Phe Thr Glu Tyr Tyr Met Thr Trp Val Arg Gln Ala Pro Gly
145                 150                 155                 160

Lys Gly Leu Glu Trp Leu Ala Tyr Ile Ser Lys Asn Gly Glu Tyr Ser
                165                 170                 175

Lys Tyr Ser Pro Ser Ser Asn Gly Arg Phe Thr Ile Ser Arg Asp Asn
            180                 185                 190

Ala Lys Asn Ser Val Phe Leu Gln Leu Asp Arg Leu Ser Ala Asp Asp
        195                 200                 205

Thr Ala Val Tyr Tyr Cys Ala Arg Ala Asp Gly Leu Thr Tyr Phe Ser
    210                 215                 220

Glu Leu Leu Gln Tyr Ile Phe Asp Leu Trp Gly Gln Gly Ala Arg Val
225                 230                 235                 240

Thr Val Ser Ser Gly Gly Cys Gly Gly Gly Lys Val Ala Ala Leu Lys
                245                 250                 255

Glu Lys Val Ala Ala Leu Lys Glu Lys Val Ala Ala Leu Lys Glu Lys
            260                 265                 270

```
Val Ala Ala Leu Lys Glu
        275

<210> SEQ ID NO 50
<211> LENGTH: 272
<212> TYPE: PRT
<213> ORGANISM: Artificial Sequence
<220> FEATURE:
<223> OTHER INFORMATION: First Polypeptide Chain of Anti-RSV F Protein
      Antibody Palvizumab x Anti-CD3 Antibody 2 Bispecific Diabody

<400> SEQUENCE: 50

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Thr Leu Arg Glu Ser Gly Pro Ala
        115                 120                 125

Leu Val Lys Pro Thr Gln Thr Leu Thr Leu Thr Cys Thr Phe Ser Gly
    130                 135                 140

Phe Ser Leu Ser Thr Ser Gly Met Ser Val Gly Trp Ile Arg Gln Pro
145                 150                 155                 160

Pro Gly Lys Ala Leu Glu Trp Leu Ala Asp Ile Trp Trp Asp Asp Lys
                165                 170                 175

Lys Asp Tyr Asn Pro Ser Leu Lys Ser Arg Leu Thr Ile Ser Lys Asp
            180                 185                 190

Thr Ser Lys Asn Gln Val Val Leu Lys Val Thr Asn Met Asp Pro Ala
        195                 200                 205

Asp Thr Ala Thr Tyr Tyr Cys Ala Arg Ser Met Ile Thr Asn Trp Tyr
    210                 215                 220

Phe Asp Val Trp Gly Ala Gly Thr Thr Val Thr Val Ser Ser Gly Gly
225                 230                 235                 240

Cys Gly Gly Gly Glu Val Ala Ala Leu Glu Lys Glu Val Ala Ala Leu
                245                 250                 255

Glu Lys Glu Val Ala Ala Leu Glu Lys Glu Val Ala Ala Leu Glu Lys
            260                 265                 270

<210> SEQ ID NO 51
<211> LENGTH: 273
<212> TYPE: PRT
<213> ORGANISM: Artificial Sequence
<220> FEATURE:
<223> OTHER INFORMATION: Second Polypeptide Chain of Anti-RSV F Protein
      Antibody Palvizumab x Anti-CD3 Antibody 2 Bispecific Diabody

<400> SEQUENCE: 51

Asp Ile Gln Met Thr Gln Ser Pro Ser Thr Leu Ser Ala Ser Val Gly
1               5                   10                  15
```

-continued

```
Asp Arg Val Thr Ile Thr Cys Arg Ala Ser Gln Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
210                 215                 220

Trp Phe Ala Tyr Trp Gly Gln Gly Thr Leu Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270

Glu
```

<210> SEQ ID NO 52
<211> LENGTH: 273
<212> TYPE: PRT
<213> ORGANISM: Artificial Sequence
<220> FEATURE:
<223> OTHER INFORMATION: First Polypeptide Chain of Anti-Fluorescein
      Antibody 4-4-20 x Anti-HIV env Antibody 7B2 Bispecific Diabody

<400> SEQUENCE: 52

```
Asp Ile Val Met Thr Gln Ser Pro Asp Ser Leu Ala Val Ser Pro Gly
 1               5                  10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
 50                  55                  60

Pro Asp Arg Phe Ser Gly Ser Gly Ser Gly Thr Asp Phe Thr Leu Thr
 65                  70                  75                  80

Ile Asn Asn Leu Gln Ala Glu Asp Val Ala Ile Tyr Tyr Cys His Gln
                85                  90                  95
```

Tyr Ser Ser His Pro Pro Thr Phe Gly His Gly Thr Arg Val Glu Ile
                100                 105                 110

Lys Gly Gly Gly Ser Gly Gly Gly Gly Glu Val Lys Leu Asp Glu Thr
            115                 120                 125

Gly Gly Gly Leu Val Gln Pro Gly Arg Pro Met Lys Leu Ser Cys Val
        130                 135                 140

Ala Ser Gly Phe Thr Phe Ser Asp Tyr Trp Met Asn Trp Val Arg Gln
145                 150                 155                 160

Ser Pro Glu Lys Gly Leu Glu Trp Val Ala Gln Ile Arg Asn Lys Pro
                165                 170                 175

Tyr Asn Tyr Glu Thr Tyr Tyr Ser Asp Ser Val Lys Gly Arg Phe Thr
            180                 185                 190

Ile Ser Arg Asp Asp Ser Lys Ser Ser Val Tyr Leu Gln Met Asn Asn
        195                 200                 205

Leu Arg Val Glu Asp Met Gly Ile Tyr Tyr Cys Thr Gly Ser Tyr Tyr
210                 215                 220

Gly Met Asp Tyr Trp Gly Gln Gly Thr Ser Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys

<210> SEQ ID NO 53
<211> LENGTH: 280
<212> TYPE: PRT
<213> ORGANISM: Artificial Sequence
<220> FEATURE:
<223> OTHER INFORMATION: Second Polypeptide Chain of Anti-Fluorescein
      Antibody 4-4-20 x Anti-HIV env Antibody 7B2 Bispecific Diabody

<400> SEQUENCE: 53

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Gln Val Gln Leu Val Gln Ser Gly
        115                 120                 125

Gly Gly Val Phe Lys Pro Gly Gly Ser Leu Arg Leu Ser Cys Glu Ala
    130                 135                 140

Ser Gly Phe Thr Phe Thr Glu Tyr Tyr Met Thr Trp Val Arg Gln Ala
145                 150                 155                 160

Pro Gly Lys Gly Leu Glu Trp Leu Ala Tyr Ile Ser Lys Asn Gly Glu
                165                 170                 175

```
Tyr Ser Lys Tyr Ser Pro Ser Ser Asn Gly Arg Phe Thr Ile Ser Arg
            180             185                 190

Asp Asn Ala Lys Asn Ser Val Phe Leu Gln Leu Asp Arg Leu Ser Ala
            195             200             205

Asp Asp Thr Ala Val Tyr Tyr Cys Ala Arg Ala Asp Gly Leu Thr Tyr
    210             215             220

Phe Ser Glu Leu Leu Gln Tyr Ile Phe Asp Leu Trp Gly Gln Gly Ala
225             230             235                 240

Arg Val Thr Val Ser Ser Gly Gly Cys Gly Gly Lys Val Ala Ala
                245             250             255

Leu Lys Glu Lys Val Ala Ala Leu Lys Glu Lys Val Ala Ala Leu Lys
            260             265             270

Glu Lys Val Ala Ala Leu Lys Glu
            275             280
```

BISPECIFIC MOLECULES THAT ARE IMMUNOREACTIVE WITH IMMUNE EFFECTOR CELLS THAT EXPRESS AN ACTIVATING RECEPTOR AND AN ANTIGEN EXPRESSED BY A CELL INFECTED BY A VIRUS AND USES THEREOF

CROSS-REFERENCE TO RELATED APPLICATIONS

The present application is a continuation of U.S. patent application Ser. No. 15/879,056 (filed Jan. 24, 2018), which application is a continuation of U.S. patent application Ser. No. 14/775,041 (filed Sep. 11, 2015, issued as U.S. Pat. No. 9,908,938), which is a national stage application of International Application No. PCT/US2014/025491 (filed Mar. 13, 2014), which claims priority to U.S. Patent Application Ser. No. 61/783,195 (filed Mar. 14, 2013), which applications are incorporated herein by reference in their entireties and to which priority is claimed.

REFERENCE TO SEQUENCE LISTING

This application includes one or more Sequence Listings pursuant to 37 C.F.R. 1.821 et seq., which are disclosed in computer-readable media (filed name: Seq_Listing_ST25.txt, created Jun. 16, 2020, and having a size of 65,530 bytes), and which computer-readable media is herein incorporated by reference in its entirety.

BACKGROUND OF THE INVENTION

Field of the Invention

The present invention relates to bispecific molecules that are capable of localizing an immune effector cell that expresses an activating receptor to a virally infected cell, so as to thereby facilitate the killing of the virally infected cell. In a preferred embodiment, such localization is accomplished using bispecific molecules that are immunoreactive both to an activating receptor of an immune effector cell and to an epitope of an antigen expressed by a cell infected with a virus. The present invention additionally concerns the use of such bispecific molecules in the treatment of latent viral infections, persistent viral infections and inactive viral infections, and the use of such bispecific molecules in methods to kill cells containing a viral genome or cell expressing a viral protein. The invention particularly concerns bispecific molecules that bind to (1) an epitope of an activating receptor of an immune effector cell and (2) an epitope of an antigen expressed by a cell infected with a virus wherein the antigen is detectably present on the cell infected by the virus at a level that is greater than the level at which the antigen is detected on the virus by the bispecific molecules and to such bispecific molecules that are capable of mediating, and more preferably enhancing, the activation and targeting of the immune effector cells to the cell infected by the virus such that the activated immune effector cells kill the cell infected by the virus.

Description of Related Art

I. Viral Infectious Disease

The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases,*" Singapore Med. J. 50(7):663-666). Nearly 200 antibody-based drugs have been approved for use or are under development.

Such drugs hold particular promise for the treatment of infectious diseases, and most significantly, for the treatment of viral infectious diseases. Many pathogens have demonstrated a marked ability to gain resistance to conventional antimicrobial drugs (e.g., methicillin-resistant *Staphylococcus aureus*, extreme drug-resistant *Mycobacterium tuberculosis* and antimicrobial resistant *Plasmodium falciparum*). Other pathogens, such as HIV, influenza virus, etc. are presently not satisfactorily treatable using traditional drugs (see, Beigel, J. et al. (2008) "*Current And Future Antiviral Therapy Of Severe Seasonal And Avian Influenza,*" Antiviral Res. 78(1):91-102). Moreover, such drugs exhibit significant side effects. In contrast to traditional drugs, antibodies have two properties that make them highly attractive as therapeutic agents. First, since antibodies are endogenous proteins native to the body, they exhibit low toxicity. Second, they exhibit high specificity, which enables the directed targeting of infected cells.

However, present immunotherapy has certain drawbacks (Chan, C. E. et al. (2009) "*The Use Of Antibodies In The Treatment Of Infectious Diseases,*" Singapore Med. J. 50(7): 663-666). The clearance of a viral infection is usually associated with T cell-mediated adaptive immunity. $CD8^+$ T cells act by killing virally-infected cells, thus preventing viral replication and reducing the viral load. In addition, antibodies can promote the killing of infected cells expressing viral proteins on their surface through the activation of natural killer (NK) cells that mediate ADCC, in addition to their viral neutralization properties. Although antibodies have been shown to be able to neutralize many viral pathogens in vitro, the extent to which antibody-mediated immunity can achieve viral clearance in vivo is unclear. Thus, neutralizing therapeutic antibodies are typically administered not to mediate clearance, but rather to suppress viral replication and viremia and give the host immune system time to develop an effective response for viral clearance. In this regard, studies have shown that the capacity of antibodies to reduce viral load correlated with the persistence of the administered antibody in serum, and that viral antigen levels eventually recovered once antibody levels in the serum had declined following the cessation of therapy (Galun, E. et al. (2002) "*Clinical Evaluation (Phase I) Of A Combination Of Two Human Monoclonal Antibodies To HBV: Safety And Antiviral Properties,*" Hepatology 35:673-679; Heijtink, R. A. et al. (2001) "*Administration Of A Human Monoclonal Antibody (TUVIRUMAB) To Chronic Hepatitis B Patients Pre-Treated With Lamivudine: Monitoring Of Serum TUVIRUMAB In Immune Complexes,*" J. Med. Virol. 64:427-434). Additionally, studies with HIV have shown that the regular administration of therapeutic antibodies may lead to the development of escape mutants (Chan, C. E. et al. (2009) "*The Use Of Antibodies In The Treatment Of Infectious Diseases,*" Singapore Med. J. 50(7): 663-666). In one study, a combination of three broadly neutralizing HIV antibodies administered over a period of 12 weeks succeeded in delaying viral rebound after the cessation of antiviral treatment, relative to controls. However, viral levels eventually recovered despite the continued administration of all three antibodies, with increased resistance to one of the three administered antibodies (Trkola, A. et al. (2005) "*Delay Of HIV-1 Rebound After Cessation Of Antiretroviral Therapy Through Passive Transfer Of Human Neutralizing Antibodies,*" Nat. Med. 11:615-622).

II. Immune System Activation

CD4+ T-lymphocytes are the essential organizers of most mammalian immune and autoimmune responses (Dong, C. et al. (2003) "*Immune Regulation by Novel Costimulatory Molecules*," Immunolog. Res. 28(1):39-48). The activation of CD4+ helper T-cells has been found to be mediated through co-stimulatory interactions between Antigen Presenting Cells and naive CD4+ T-lymphocytes. Two interactions are required (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). In the first interaction, an Antigen Presenting Cell must display the relevant target antigen bound to the cell's major histocompatibility complex so that it can bind to the T-cell Receptor ("TCR") of a naive CD4+ T-lymphocyte. In the second interaction, a ligand of the Antigen Presenting Cell must bind to a CD28 receptor of the CD4+ T-lymphocyte (Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). CD4+ helper T-cells experiencing both stimulatory signals are then capable of responding to cytokines (such as Interleukin-2 and Interleukin-12) to develop into Th1 cells. Such cells produce interferon-gamma (IFN-γ) and tumor necrosis factor-alpha (TNF-α), which mediate inflammatory responses to target cells expressing the target antigen. B-cell activation and proliferation also occurs, resulting in antibody production specific for the target antigen (Bernard, A. et al. (2005) "*T and B Cell Cooperation: A Dance of Life and Death*," Transplantation 79:S8-S11). In the absence of both co-stimulatory signals during TCR engagement, T cells enter a functionally unresponsive state, referred to as clonal anergy (Khawli, L. A. et al. (2008) "*Cytokine, Chemokine, and Co-Stimulatory Fusion Proteins for the Immunotherapy of Solid Tumors*," Exper. Pharmacol. 181:291-328). In pathologic states, Th1 cells are the key players of various organ-specific autoimmune diseases, such as type I diabetes, rheumatoid arthritis, and multiple sclerosis (Dong, C. et al. (2003) "*Immune Regulation by Novel Costimulatory Molecules*," Immunolog. Res. 28(1):39-48).

III. Therapeutic Antibodies

In addition to their known uses in diagnostics, antibodies have been shown to be useful as therapeutic agents. For example, immunotherapy, or the use of antibodies for therapeutic purposes, has been used in recent years to treat infectious disease. Passive immunotherapy involves the use of monoclonal antibodies to treat infection (see for example, Ian Gust, A. O. (Epub 2012 Feb. 21) "*Role Of Passive Immunotherapies In Managing Infectious Outbreaks*," Biologicals 40(3):196-199; Wang, D. et al. (2011) "*Palivizumab For Immunoprophylaxis Of Respiratory Syncytial Virus (RSV) Bronchiolitis In High-Risk Infants And Young Children: A Systematic Review And Additional Economic Modelling Of Subgroup Analyses*," Health Technol. Assess. 15(5):iii-iv, 1-124; Rosenberg, H. F. et al. (2012) "*Inflammatory Responses To Respiratory Syncytial Virus (RSV) Infection And The Development Of Immunomodulatory Pharmacotherapeutics*," Curr. Med. Chem. 19(10):1424-1431). These antibodies can have inherent therapeutic biological activity both by direct binding to the infectious agents (e.g., viruses, bacteria, fungi, etc.) and by their ability to bind to host cells that have been infected with such agents and which have expressed agent-specific antigens on their cell surfaces. These agents can be administered alone or in conjunction with other anti-infective agents (e.g., antibiotics, anti-inflammatory agents, anti-pyretic agents, etc.). Palivizumab, approved for treatment of respiratory syncytial virus (RSV) bronchiolitis, and tefibazumab (in clinical trials for the treatment of *S. aureus* infections) are examples of such therapeutics. Alternatively, antibodies can be used to make antibody conjugates in which the antibody is linked to a toxic agent and directs that agent to the tumor by specifically binding to the tumor. Gemtuzumab ozogamicin is an example of an approved antibody conjugate used for the treatment of leukemia in human patients.

Monoclonal antibodies that bind to virally-infected cells and have potential uses for diagnosis and therapy have been disclosed (see, for example, U.S. Pat. Nos. 8,313,746; 7,507,797; US 2012/0283438; US 2012/0128669; US 2012/0093834; US 2011/0319871; US 2011/0212076; US 2011/0076268; US 2011/0033389; US 2010/0040635; US 2010/0040601; US 2009/0162353; EP 1670826; WO 2011/085289; Oleksiewicz, M. B. et al. (Epub 2012 Jun. 13) "*Anti-Bacterial Monoclonal Antibodies: Back To The Future?*" Arch. Biochem. Biophys. 526(2):124-131; Huang, J. X. et al. (Epub 2012 Jun. 4) "*Development Of Anti-Infectives Using Phage Display: Biological Agents Against Bacteria, Viruses, And Parasites*," Antimicrob. Agents Chemother. 56(9):4569-4582; Ian Gust, A. O. (Epub 2012 Feb. 21) "*Role Of Passive Immunotherapies In Managing Infectious Outbreaks*," Biologicals 40(3): 196-199; Geevarghese, B. et al. (Epub 2012 Feb. 3) "*Antibodies For Prevention And Treatment Of Respiratory Syncytial Virus Infections In Children*," Antivir. Ther. 17(1 Pt B):201-211; Rosenberg, H. F. et al. (2012) "*Inflammatory Responses To Respiratory Syncytial Virus (RSV) Infection And The Development Of Immunomodulatory Pharmacotherapeutics*," Curr. Med. Chem. 19(10):1424-1431; Nossal, G. J. (2011) "*Vaccines Of The Future*," Vaccine 29 Suppl 4:D111-115; Froude, J. W. et al. (2011) "*Antibodies For Biodefense*," MAbs 3(6):517-527; Ter Meulen, J. (2011) "*Monoclonal Antibodies In Infectious Diseases: Clinical Pipeline In 2011*," Infect. Dis. Clin. North Am. 25(4):789-802; Yamada, T. (2011) "*Therapeutic Monoclonal Antibodies*," Keio J. Med. 60(2):37-46; Berry, J. D. et al. (2011) "*Antibodies In Infectious Diseases: Polyclonals, Monoclonals And Niche Biotechnology*," Nature Biotechnol. 28(5):489-501; Whaley, K. J. et al. (2011) "*Emerging Antibody Products And Nicotiana Manufacturing*," Hum. Vaccin. 7(3):349-356; Beasley, D. W. (2011) "*Vaccines And Immunotherapeutics For The Prevention And Treatment Of Infections With West Nile Virus*," Immunotherapy 3(2):269-285; Wang, D. et al. (2011) "*Palivizumab For Immunoprophylaxis Of Respiratory Syncytial Virus (RSV) Bronchiolitis In High-Risk Infants And Young Children: A Systematic Review And Additional Economic Modelling Of Subgroup Analyses*," Health Technol. Assess. 15(5):iii-iv, 1-124; Li, L. et al. (2010) "*Immunotherapy For Prion Diseases: Opportunities And Obstacles*," Immunotherapy 2(2):269-282; Niebecker, R. et al. (2010) "*Safety Of Therapeutic Monoclonal Antibodies*," Curr. Drug. Saf. 5(4):275-286; Hansel, T. T. et al. (2010) "*The Safety And Side Effects Of Monoclonal Antibodies*," Nat. Rev. Drug Discov. 9(4):325-338; Chan, C. E. et al. (2009) "*The Use Of Antibodies In The Treatment Of Infectious Diseases*," Singapore Med. J. 50(7):663-673; Beigel, J. et al. (2008) "*Current And Future Antiviral Therapy Of Severe Seasonal And Avian Influenza*," Antiviral Res. 78(1):91-102; Huber, M. et al. (2008) "*Antibodies For HIV Treatment And Prevention: Window Of Opportunity?*" Curr. Top. Microbiol.

Immunol. 317:39-66; ter Meulen, J. (2007) *"Monoclonal Antibodies For Prophylaxis And Therapy Of Infectious Diseases,"* Expert Opin. Emerg. Drugs. 12(4):525-540).

An ideal therapeutic and/or diagnostic antibody would be specific for an antigen present on infected cells, but absent or present only at low levels on any normal tissue. The discovery, characterization, and isolation of a novel antibody capable of binding to an antigen present on infected cells that is specifically associated with an infectious disease, and particularly a viral disease, would be useful in many ways. First, the antibody would have biological activity against such cells and be able to recruit the immune system's response to thereby treat the disease. The antibody could be administered as a therapeutic alone or in combination with current treatments or used to prepare immunoconjugates linked to toxic agents. An antibody with the same specificity but with low or no biological activity when administered alone could also be useful in that an antibody could be used to prepare an immunoconjugate with a radioisotope, a toxin, or a chemotherapeutic agent or liposome containing a chemotherapeutic agent, with the conjugated form being biologically active by virtue of the antibody directing the toxin to the antigen-containing cells.

One aspect desirable for an ideal therapeutic and/or diagnostic antibody would be the discovery and characterization of novel antibodies capable of mediating, and particularly of enhancing the activation of the immune system against infected cells (and especially against virally infected cells) that are associated with any of a variety of viral diseases.

Despite all prior advances, a need remains for improved compositions capable of binding to cells infected with a virus and of facilitating or mediating an immune response against the virally-infected cells. In addition, a need remains for improved compositions capable of detecting such virally-infected cells. It is an object of this invention to identify such compositions. It is another object to provide novel compounds for use in the detection of antigens expressed on the surface of virally-infected cells.

As described in detail below, the present invention relates to bispecific molecules that bind to 1) an epitope of an activating receptor of an immune effector cell and 2) an epitope of an antigen expressed by a cell infected with a virus and that such bispecific molecules are capable of mediating, and more preferably enhancing, the activation and targeting of the immune effector cells to the virally-infected cells expressing the epitope such that the activated immune effector cells kill the virally-infected cells.

BRIEF DESCRIPTION OF THE FIGURES

FIG. 1A depicts a two polypeptide chain bispecific diabody having epitope binding domains A-D and additional domains E and F. FIG. 1B depicts a two polypeptide chain bispecific diabody having E coil and K coil domains. FIG. 1C depicts a three polypeptide chain bispecific diabody having an Fc domain that forms through the association of two CH2-CH3 domains.

Figure 1A:
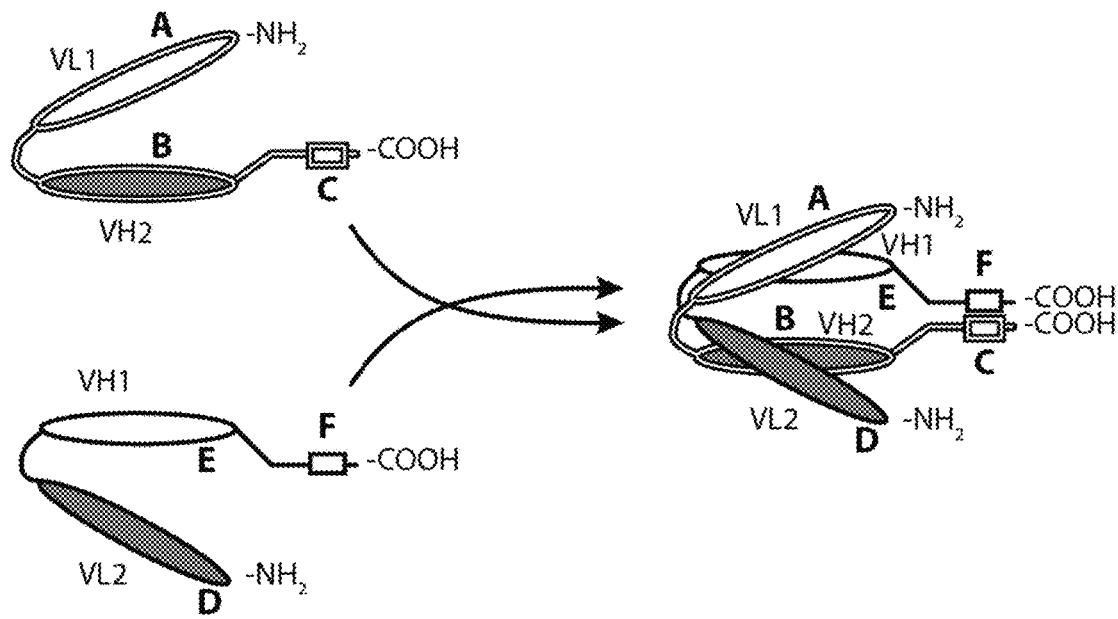
FIGS. 1A-1C illustrate the structures and domains of the bispecific molecules of the present invention.

D371 cells (CM244, subtype AE, R5-tropic) in the presence of pan T cells (D47239). The Effector:Target ratio was 10:1. A bispecific diabody comprising the anti-HIV env epitope binding domains of antibody 7B2 and the anti-fluorescein epitope binding domains of antibody 4-4-20 was used as a control.

SUMMARY OF THE INVENTION

The present invention relates to bispecific molecules that are capable of localizing an immune effector cell that expresses an activating receptor to a virally infected cell, so as to thereby facilitate the killing of the virally infected cell. In a preferred embodiment, such localization is accomplished using bispecific molecules that are immunoreactive both to an activating receptor of an immune effector cell and to an epitope of an antigen expressed by a cell infected with a virus. The present invention additionally concerns the use of such bispecific molecules in the treatment of latent viral infections, persistent viral infections and inactive viral infections, and the use of such bispecific molecules in methods to kill cells containing a viral genome or cell expressing a viral protein. The invention particularly concerns bispecific molecules that bind to (1) an epitope of an activating receptor of an immune effector cell and (2) an epitope of an antigen expressed by a cell infected with a virus wherein the antigen is detectably present on the cell infected by the virus at a level that is greater than the level at which the antigen is detected on the virus by the bispecific molecules and to such bispecific molecules that are capable of mediating, and more preferably enhancing, the activation and targeting of the immune effector cells to the cell infected by the virus such that the activated immune effector cells kill the cell infected by the virus.

In detail, the invention concerns a bispecific molecule comprising:
  (A) a first epitope-binding domain, the first epitope-binding domain being capable of immunospecifically binding to an epitope of a protein expressed on the surface of an immune effector cell, wherein the immune effector cell expresses an activating receptor, and
  (B) a second epitope-binding domain, the second epitope-binding domain being capable of immunospecifically binding to an epitope of an antigen expressed by a cell infected with a virus; wherein the antigen is detectably present on the cell infected by the virus at a level that is greater than the level at which the antigen is detected on the virus by the bispecific molecule.

The invention further concerns the embodiment of such bispecific molecule, wherein the first epitope-binding domain binds an activating receptor of the effector cell.

The invention further concerns any of the above-described bispecific molecules, wherein the effector cell is a T-cell, a CD4+ T-cell, a CD8+ T-cell, a natural killer cell, a macrophage, a granulocyte, or a dendritic cell.

The invention further concerns any of the above-described bispecific molecules, wherein the virus is Epstein-Barr virus, herpes simplex virus type 1, herpes simplex virus type 2, cytomegalovirus, human immunodeficiency virus, hepatitis B virus, hepatitis C virus, human papilloma virus or influenza virus.

The invention further concerns any of the above-described bispecific molecules, wherein the cell is latently infected with the virus.

The invention further concerns any of the above-described bispecific molecules, wherein the antigen expressed by the cell infected with the virus is selected from the group consisting of LMP-1, LMP-2, influenza $M_2$ protein, HIV env protein, HPV E6 and HPV E7.

The invention further concerns any of the above-described bispecific molecules, wherein the antigen expressed by the cell infected with the virus is detectably present on the cell and is not detected on the virus by the bispecific molecule.

The invention further concerns any of the above-described bispecific molecules, wherein the epitope on the effector cell is a CD3 epitope, a CD4 epitope, a CD8 epitope, a CD2 epitope, a CD16 epitope, or an NKG2D epitope.

The invention further concerns any of the above-described bispecific molecules, wherein the first antigen binding domain is an antigen binding domain from a CD3 antibody, a CD4 antibody, a CD8 antibody, a CD2 antibody, a CD16 antibody, or an NKG2D antibody.

The invention further concerns any of the above-described bispecific molecules, wherein the antigen expressed by the cell infected with the virus is detectably present on the cell at a level that is at least 2 times greater than the level, if any, at which the antigen is detected on the virus by the bispecific molecule.

The invention further concerns any of the above-described bispecific molecules, wherein the antigen expressed by the cell infected with the virus is detectably present on the cell at a level that is at least 5 times greater than the level, if any, at which the antigen is detected on the virus by the bispecific molecule.

The invention further concerns any of the above-described bispecific molecules, wherein the antigen expressed by the cell infected with the virus is detectably present on the cell at a level that is at least 10 times greater than the level, if any, at which the antigen is detected on the virus by the bispecific molecule.

The invention further concerns any of the above-described bispecific molecules, wherein the antigen expressed by the cell infected with the virus is detectably present on the cell at a level that is at least 100 times greater than the level, if any, at which the antigen is detected on the virus by the bispecific molecule.

The invention further concerns any of the above-described bispecific molecules, wherein the antigen is detectably present on the cell infected by the virus at a level that is greater than the level at which the antigen is detected by the bispecific molecule on a cell that is not infected by the virus.

The invention further concerns any of the above-described bispecific molecules, wherein the antigen is detectably present on the cell infected by the virus at a level that is at least 2 times greater than the level at which the antigen is detected by the bispecific molecule on a cell that is not infected by the virus.

The invention further concerns any of the above-described bispecific molecules, wherein the antigen is detectably present on the cell infected by the virus at a level that is at least 5 times greater than the level at which the antigen is detected by the bispecific molecule on a cell that is not infected by the virus.

The invention further concerns any of the above-described bispecific molecules, wherein the antigen is detectably present on the cell infected by the virus at a level that is at least 10 times greater than the level at which the antigen is detected by the bispecific molecule on a cell that is not infected by the virus.

The invention further concerns any of the above-described bispecific molecules, wherein the antigen is detectably present on the cell infected by the virus at a level that is at least 100 times greater than the level at which the antigen is detected by the bispecific molecule on a cell that is not infected by the virus.

The invention further concerns any of the above-described bispecific molecules, wherein the antigen expressed by the cell infected with the virus is detectably present on the cell and is not detected on a cell not infected with the bispecific molecule.

The invention further concerns a pharmaceutical composition comprising a bispecific molecule and a pharmaceutically acceptable carrier; the bispecific molecule comprising:
  (A) a first epitope-binding domain, the first epitope-binding domain being capable of immunospecifically binding to an epitope of a protein expressed on the surface of an immune effector cell, wherein the immune effector cell expresses an activating receptor of an effector cell, and
  (B) a second epitope-binding domain, the second epitope-binding domain being capable of immunospecifically binding to an epitope of an antigen expressed by a cell infected with a virus; wherein the antigen is detectably present on the cell infected by the virus at a level that is greater than the level at which the antigen is detected on the virus by the bispecific molecule.

The invention further concerns the embodiment of such pharmaceutical composition, wherein the first epitope-binding domain binds an activating receptor of the effector cell.

The invention further concerns a method of treating a latent virus infection in an individual in need of such treatment, the method comprising the step of administering a therapeutically effective amount of a bispecific molecule to the individual, the bispecific molecule comprising:
  (A) a first epitope-binding domain, the first epitope-binding domain being capable of immunospecifically binding to a protein expressed on the surface of an immune effector cell, wherein said immune effector cell expresses an epitope of an activating receptor of an effector cell, and
  (B) a second epitope-binding domain, the second epitope-binding domain being capable of immunospecifically binding to an epitope of an antigen expressed by a cell infected with a virus; wherein the antigen is detectably present on the cell infected by the virus at a level that is greater than the level at which the antigen is detected on the virus by the bispecific molecule.

The invention further concerns the embodiment of such method, wherein the first epitope-binding domain of the bispecific molecule binds an activating receptor of the effector cell.

The invention further concerns a method of treating a persistent virus infection in an individual in need of such treatment, the method comprising the step of administering a therapeutically effective amount of a bispecific molecule to the individual, the bispecific molecule comprising:
  (A) a first epitope-binding domain, the first epitope-binding domain being capable of immunospecifically binding to a protein expressed on the surface of an immune effector cell, wherein the immune effector cell expresses an epitope of an activating receptor of an effector cell, and
  (B) a second epitope-binding domain, the second epitope-binding domain being capable of immunospecifically binding to an epitope of an antigen expressed by a cell infected with a virus; wherein the antigen is detectably present on the cell infected by the virus at a level that is greater than the level at which the antigen is detected on the virus by the bispecific molecule.

The invention further concerns the embodiment of such method, wherein the first epitope-binding domain of the bispecific molecule binds an activating receptor of the effector cell.

The invention further concerns methods of treating an inactive virus infection in an individual in need of such treatment, the method comprising the step of administering a therapeutically effective amount of a bispecific molecule to the individual, the bispecific molecule comprising:
  (A) a first epitope-binding domain, the first epitope-binding domain being capable of immunospecifically binding to a protein expressed on the surface of an immune effector cell, wherein the immune effector cell expresses an epitope of an activating receptor of an effector cell, and
  (B) a second epitope-binding domain, the second epitope-binding domain being capable of immunospecifically binding to an epitope of an antigen expressed by a cell infected with a virus; wherein the antigen is detectably present on the cell infected by the virus at a level that is greater than the level at which the antigen is detected on the virus by the bispecific molecule.

The invention further concerns the embodiment of such method, wherein the first epitope-binding domain of the bispecific molecule binds an activating receptor of the effector cell.

The invention further concerns methods of killing a cell containing a viral genome, the method comprises the step of contacting the cell with a bispecific molecule, the bispecific molecule comprising:
  (A) a first epitope-binding domain, the first epitope-binding domain being capable of immunospecifically binding to a protein expressed on the surface of an immune effector cell, wherein the immune effector cell expresses an epitope of an activating receptor of an effector cell, and
  (B) a second epitope-binding domain, the second epitope-binding domain being capable of immunospecifically binding to an epitope of an antigen expressed by a cell infected with a virus; wherein the antigen is detectably present on the cell infected by the virus at a level that is greater than the level at which the antigen is detected on the virus by the bispecific molecule.

The invention further concerns the embodiment of such method, wherein the first epitope-binding domain of the bispecific molecule binds an activating receptor of the effector cell.

The invention further concerns methods of killing a cell expressing a viral protein, the method comprises the step of contacting the cell with a bispecific molecule, the bispecific molecule comprising:
  (A) a first epitope-binding domain, the first epitope-binding domain being capable of immunospecifically binding to a protein expressed on the surface of an immune effector cell, wherein the immune effector cell expresses an epitope of an activating receptor of an effector cell, and
  (B) a second epitope-binding domain, the second epitope-binding domain being capable of immunospecifically binding to an epitope of an antigen expressed by a cell infected with a virus; wherein the antigen is detectably present on the cell infected by the virus at a level that is greater than the level at which the antigen is detected on the virus by the bispecific molecule.

The invention further concerns the embodiment of such method, wherein the first epitope-binding domain of the bispecific molecule binds an activating receptor of the effector cell.

DETAILED DESCRIPTION OF THE INVENTION

The present invention relates to bispecific molecules that are capable of localizing an immune effector cell that expresses an activating receptor to a virally infected cell, so as to thereby facilitate the killing of the virally infected cell. In a preferred embodiment, such localization is accomplished using bispecific molecules that are immunoreactive both to an activating receptor of an immune effector cell and to an epitope of an antigen expressed by a cell infected with a virus. The present invention additionally concerns the use of such bispecific molecules in the treatment of latent viral infections, persistent viral infections and inactive viral infections, and the use of such bispecific molecules in methods to kill cells containing a viral genome or cell expressing a viral protein. The invention particularly concerns bispecific molecules that bind to (1) an epitope of an activating receptor of an immune effector cell and (2) an epitope of an antigen expressed by a cell infected with a virus wherein the antigen is detectably present on the cell infected by the virus at a level that is greater than the level at which the antigen is detected on the virus by the bispecific molecules and to such bispecific molecules that are capable of mediating, and more preferably enhancing, the activation and targeting of the immune effector cells to the cell infected by the virus such that the activated immune effector cells kill the cell infected by the virus.

The capacity of such bispecific molecules to bind to both an activating receptor of an immune effector cell an epitope of an antigen expressed by a cell infected with a virus permits such bispecific molecules to be used in the treatment of active viral infections, latent viral infections, persistent viral infections, and inactive viral infections.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, MOLECULAR CLONING: A LABORATORY MANUAL, Third Edition (Sambrook et al. Eds., 2001) Cold Spring Harbor Press, Cold Spring Harbor, N.Y.; OLIGONUCLEOTIDE SYNTHESIS: METHODS AND APPLICATIONS (Methods in Molecular Biology), Herdewijn, P., Ed., Humana Press, Totowa, N.J.; OLIGONUCLEOTIDE SYNTHESIS (Gait, M. J., Ed., 1984); METHODS IN MOLECULAR BIOLOGY, Humana Press, Totowa, N.J.; CELL BIOLOGY: A LABORATORY NOTEBOOK (Cellis, J. E., Ed., 1998) Academic Press, New York, N.Y.; ANIMAL CELL CULTURE (Freshney, Ed., 1987); INTRODUCTION TO CELL AND TISSUE CULTURE (Mather, J. P. and Roberts, P. E., Eds., 1998) Plenum Press, New York, N.Y.; CELL AND TISSUE CULTURE: LABORATORY PROCEDURES (Doyle, A. et al., Eds., 1993-8) John Wiley and Sons, Hoboken, N.J.; METHODS IN ENZYMOLOGY (Academic Press, Inc.) New York, N.Y.; WEIR'S HANDBOOK OF EXPERIMENTAL IMMUNOLOGY (Herzenberg, L. A. et al. Eds. 1997) Wiley-Blackwell Publishers, New York, N.Y.; GENE TRANSFER VECTORS FOR MAMMALIAN CELLS (Miller, J. M. et al. Eds., 1987) Cold Spring Harbor Press, Cold Spring Harbor, N.Y.; CURRENT PROTOCOLS IN MOLECULAR BIOLOGY (Ausubel, F. M. et al., Eds., 1987) Greene Pub. Associates, New York, N.Y.; PCR: THE POLYMERASE CHAIN REACTION, (Mullis, K. et al., Eds., 1994) Birkhauser, Boston Mass.; CURRENT PROTOCOLS IN IMMUNOLOGY (Coligan, J. E. et al., eds., 1991) John Wiley and Sons, Hoboken, N.J.; SHORT PROTOCOLS IN MOLECULAR BIOLOGY (John Wiley and Sons, 1999) Hoboken, N.J.; IMMUNOBIOLOGY 7 (Janeway, C. A. et al. 2007) Garland Science, London, UK; Antibodies (P. Finch, 1997) Stride Publications, Devoran, UK; ANTIBODIES: A PRACTICAL APPROACH (D. Catty., ed., 1989) Oxford University Press, USA, New York N.Y.); MONOCLONAL ANTIBODIES: A PRACTICAL APPROACH (Shepherd, P. et al. Eds., 2000) Oxford University Press, USA, New York N.Y.; USING ANTIBODIES: A LABORATORY MANUAL (Harlow, E. et al. Eds., 1998) Cold Spring Harbor Laboratory Press, Cold Spring Harbor, N.Y.; THE ANTIBODIES (Zanetti, M. et al. Eds. 1995) Harwood Academic Publishers, London, UK); and DEVITA, HELLMAN, AND ROSENBERG'S CANCER: PRINCIPLES & PRACTICE OF ONCOLOGY, EIGHTH EDITION, DeVita, V. et al. Eds. 2008, Lippincott Williams & Wilkins, Philadelphia, Pa.

II. Definitions

As used herein, an "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also mutants thereof, naturally occurring variants, fusion proteins comprising an antibody portion with an antigen recognition site of the required specificity, humanized antibodies, and chimeric antibodies, and any other modified configuration of the immunoglobulin molecule that comprises an antigen recognition site of the required specificity. Throughout this application, the numbering of amino acid residues of the light and heavy chains of antibodies is according to the EU index as in Kabat et al. (1992) SEQUENCES OF PROTEINS OF IMMUNOLOGICAL INTEREST, National Institutes of Health Publication No. 91-3242. As used herein, an "antigen binding fragment of an antibody" is a portion of an antibody that possesses an at least one antigen recognition site. As used herein, the term encompasses fragments (such as Fab, Fab', F(ab')$_2$ Fv), and single chain (scFv).

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$ Fv), single chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody."

The term "chimeric antibody" refers to a chimeric molecule, generally prepared using recombinant techniques, having a variable region derived from an immunoglobulin from a non-human species and the remaining immunoglobulin structure of the molecule based upon the structure and/or sequence of a human immunoglobulin.

The term "humanized antibody" refer to a molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332: 323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which are altered with respect to the original antibody, which are also termed one or more CDRs "derived from" one or more CDRs from the original antibody.

The term "BiTEs" (bi-specific T-cell engagers) refers to a single polypeptide chain molecule having two antigen binding domains, one of which binds to a T-cell antigen and the second of which binds to an antigen present on the surface of a target cell (WO 05/061547; Baeuerle, P et al. (2008) "*BiTE: A New Class Of Antibodies That Recruit T Cells*," Drugs of the Future 33: 137-147; Bargou, et al. 2008) "*Tumor Regression in Cancer Patients by Very Low Doses of a T Cell-Engaging Antibody*," Science 321: 974-977).

The term "diabody" refers to a molecule that comprises at least two polypeptide chains that preferably associate through a covalent interaction to form at least two epitope binding sites, which may recognize the same or different epitopes. Each of the polypeptide chains of a diabody comprises an immunoglobulin light chain variable region and an immunoglobulin heavy chain variable region, but these regions do not interact to form an epitope binding site. Rather, the immunoglobulin heavy chain variable region of one (e.g., the first) of the diabody polypeptide chains interacts with the immunoglobulin light chain variable region of a different (e.g., the second) diabody polypeptide chain to form an epitope binding site. Similarly, the immunoglobulin light chain variable region of one (e.g., the first) of the diabody polypeptide chains interacts with the immunoglobulin heavy chain variable region of a different (e.g., the second) diabody polypeptide chain to form an epitope binding site. Diabodies may be monospecific, bispecific, trispecific, etc., thus being able to simultaneously bind one, two, three or more different epitopes (which may be of the same or of different antigens). Diabodies may additionally be monovalent, bivalent, trivalent, tetravalent, pentavalent, hexavelent, etc., thus being able to simultaneously bind one, two, three, four, five, six or more molecules. These two attributes of diabodies (i.e., degree of specificity and valency may be combined, for example to produce bispecific antibodies (i.e., capable of binding two epitopes) that are tetravalent (i.e., capable of binding four sets of epitopes), etc. Diabody molecules are disclosed in PCT Publications WO 2006/113665, WO 2008/157379 and WO 2010/080538.

As used herein, an antibody or a polypeptide is said to "specifically" bind a region of another molecule (i.e., an epitope) if it reacts or associates more frequently, more rapidly, with greater duration and/or with greater affinity with that epitope relative to alternative epitopes. For example, an antibody that specifically binds to a viral epitope is an antibody that binds this viral epitope with greater affinity, avidity, more readily, and/or with greater duration than it binds to other viral epitopes or non-viral epitopes. It is also understood by reading this definition that, for example, an antibody (or moiety or epitope) that specifically binds to a first target may or may not specifically or preferentially bind to a second target. As such, "specific binding" does not necessarily require (although it can include) exclusive binding. Generally, but not necessarily, reference to binding means "specific" binding.

As used herein, the term "immunologically active" in reference to an epitope being or "remaining immunologically active" refers to the ability of an antibody (e.g., an anti-viral antibody or an antibody that binds an activating receptor of an immune cell or a protein present on the surface of an immune effector cell that expresses such an activating receptor) to bind to the epitope under different conditions, for example, after the epitope has been subjected to reducing and denaturing conditions.

Different biological functions are associated with anti-viral antibodies, antibodies that bind an activating receptor of an immune cell, or antibodies that bind a protein present on the surface of an immune effector cell that expresses such an activating receptor, including, but not limited to one or more of: an ability to specifically bind to such viral epitope or such activating receptor (and in particular such molecules that are expressed on the surfaces of human cells, or the cells of non-human mammal; an ability to competitively inhibits preferential binding of a known anti-viral antibody or of a known antibody capable of binding to an activating receptor of an immune cell, including the ability to preferentially bind to the same epitope to which the original antibody preferentially binds; an ability to bind to a portion of a viral protein containing such epitope, or to a portion of such activating receptor of an immune cell that is exposed on the surface of a living cell in vitro or in vivo; an ability to bind to a portion of a viral protein containing such epitope, or to a portion of such activating receptor of an immune cell that is exposed on the surface of a living cell, such as but not limited to cells expressing a viral protein containing such epitope, or such activating receptor on their surface; and/or an ability to deliver a therapeutic agent or detectable marker into cells expressing such molecules on their surface. As discussed herein, polypeptides (including antibodies) of the invention may have any one or more of these characteristics, provided that they exhibit activity with respect to immune effector cells that express an activating receptor or to a virally infected cell.

As used herein, the term "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

Agents that are employed in the methods of this invention can be randomly selected or rationally selected or designed. As used herein, an agent is said to be randomly selected when the agent is chosen without prior consideration or knowledge of the specific amino acid or other chemical moieties involved in the association of the molecule with its native binding partner(s) or known antibodies. An example of a randomly selected agent is an agent that is identified through the use and screening of a chemical library or a peptide combinatorial library.

As used herein, an agent is said to be rationally selected or designed when the agent is chosen on a non-random basis that takes into account the sequence of the target site and/or its conformation in connection with the agent's action. This invention also encompasses agents that act at the sites of interaction between such activating receptor and its native binding partner, although other ligands and their interactive sites are also encompassed within the scope of this invention, whether currently known or later identified. Agents can be rationally selected or rationally designed by utilizing the peptide sequences that make up the contact sites of the receptor/ligand and/or the receptor-antibody complex. For example, a rationally selected peptide agent can be a peptide whose amino acid sequence is identical to an epitope appearing on a viral protein or an activating receptor of an immune cell as it is exposed on the surface of a living cell in its native environment. Such an agent will reduce or block the association of the viral protein or activating receptor with antibody, or the association of such viral protein or activating receptor with its native ligand, as desired, by binding to the antibody or to the native ligand.

As used herein, the term "labeled," with regard to an antibody, is intended to encompass direct labeling of the antibody by coupling (i.e., physically linking) a detectable substance, such as a radioactive agent or a fluorophore (e.g. phycoerythrin (PE) or fluorescein isothiocyanate (also known as fluoroisothiocyanate or FITC)) to the antibody, as well as indirect labeling of the probe or antibody by reactivity with a detectable substance.

As used herein, the term "association", with regard to an antibody, includes covalent and non-covalent attachment or binding of an agent (e.g., chemotherapeutic agent) to the antibody. The antibody can be associated with an agent (e.g., chemotherapeutic agent) by direct binding or indirect binding via attachment to a common platform, such that the antibody directs the localization of the agent to the infected cell to which the antibody binds and wherein the antibody and agent do not substantially dissociate under physiological conditions such that the agent is not targeted to the same infected cell to which the antibody binds or such that the agent's potency is not decreased.

The term "biological sample" encompasses a variety of sample types obtained from a companion animal that can be used in a diagnostic or monitoring assay. The definition encompasses saliva, blood and other liquid samples of biological origin, solid tissue samples such as a biopsy specimen or tissue cultures or cells derived therefrom, and the progeny thereof, for example, cells obtained from a tissue sample of an individual suspected of having a viral infection. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

The term "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, the term "delaying development of infection" means to defer, hinder, slow, retard, stabilize, and/or postpone development of such infection. This delay can be of varying lengths of time, depending on the history of the infection and/or individual being treated. As is evident to one skilled in the art, a sufficient or significant delay can, in effect, encompass prevention, in that the individual does not develop the infection.

As used herein, an "effective amount" of a pharmaceutical composition, in one embodiment, is an amount sufficient to effect beneficial or desired results including, without limitation, clinical results such as decreasing symptoms resulting from the disease attenuating a symptom of infection (e.g., viral load, fever, pain, sepsis, etc.), increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the viral disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages for antibody administration comprise one or more unit doses between 0.1-to 100 mg/kg/body weight. The preferred dosages comprise 1 to 100 mg/kg/body weight. The most preferred dosages comprise 10 mg/kg body weight to 100 mg/kg body weight. Typical doses for bispecific molecule (e.g., diabodies and BiTEs) administration comprise one or more unit doses of 0.0001 mg/kg body weight to 100 mg/kg body weight. Preferably, the dosage administered is between 0.0001 mg/kg body weight and 20 mg/kg body weight, 0.0001 mg/kg body weight and 10 mg/kg body weight, 0.0001 mg/kg body weight and 5 mg/kg body weight, 0.0001 mg/kg body weight and 2 mg/kg body weight, 0.0001 mg/kg body weight and 1 mg/kg body weight, or 0.0001 mg/kg body weight and 0.75 mg/kg/body weight.

As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. naturally present in its original source.

The term "individual" refers to a vertebrate animal, preferably a mammal. Mammals include, but are not limited to, humans, farm animals, sport animals, pets, primates, mice and rats. In the most preferred embodiment, the term individual denotes a human.

The terms "polypeptide," "oligopeptide," "peptide" and "protein" are used interchangeably herein to refer to polymers of amino acids of any length, but especially lengths greater than 5, 10, 15, 20 or 25 amino acid residues. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or as associated chains.

Also encompassed within the scope of the invention are peptidomimetics of the bispecific molecules described herein. Such peptidomimetics include peptides wherein at least one amino acid residue is substituted with an amino acid residue that is not commonly found in nature, such as the D isomer of the amino acid or an N-alkylated species of the amino acid. In other embodiments, peptidomimetics are constructed by replacing at least one amide bond (—C(=O)—NH—) in a peptide agonist, antagonist or modulators with an amide isostere. Suitable amide isosteres include: —$CH_2$—NH—, —$CH_2$—S—, —$CH_2$—S(O)—, —$CH_2$—$S(O)_2$—, —$CH_2$—$CH_2$—, —CH=CH— (E or Z form), —C(=O)—$CH_2$—, —CH(CN)—NH—, —C(OH)—$CH_2$—, and —O—C(=O)—NH—. The amide bonds in a peptide agonist, antagonist or modulator that are suitable candidates for replacement with amide isosteres include bonds that are hydrolyzable by the endogenous esterases or proteases of the intended subject of peptide agonist, antagonist or modulator treatment.

As used herein, the term "substantially pure" refers to material that is at least 50% pure (i.e., free from contaminants), more preferably at least 90% pure, more preferably at least 95% pure, more preferably at least 98% pure, more preferably at least 99% pure, and most preferably greater than 99% pure.

As used herein, the term "toxin" refers to any substance, which effects an adverse response within a cell. For example, a toxin directed to an infected cell would have an adverse, sometimes deleterious effect, on the infected cell. Examples of toxins include, but are not limited to, radioisotopes, calicheamicin, and maytansinoids.

As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) infected cells or other diseased cells, decreasing symptoms resulting from the disease, increasing the quality of life of those suffering from the disease, decreasing the dose of other medications required to treat the disease, delaying the progression of the disease, and/or prolonging survival of companion animal recipients.

As used herein, the term "virally-infected" refers to a cell that has been infected by a virus, and especially an adenovirus, an adeno-associated virus, a B virus (macacine herpesvirus I), a BK virus, a bunyavirus, a chikungunya virus, a cocksackie virus, a coronavirus, a cytomegalovirus, an eastern equine encephalitis virus, an ebola virus, an enterovirus, an epstein-barr virus, a hantavirus, a hepatitis A virus, a hepatitis B virus, a hepatitis C virus, a hepatitis D virus, a hepatitis E virus, a herpes simplex virus 1, a herpes simplex virus 2, a human foamy virus, a human herpes virus 3, a human herpes virus 5, a human herpes virus 6, a human herpes virus 7, a human immunodeficiency virus, a human papillomavirus, a human β-lymphotropic virus, a human T-cell leukemia virus I, a human T-cell leukemia virus II, an influenza virus, a JC virus, a JEV, a Kaposi's sarcoma-associated herpesvirus, a Lassa virus, a lymphocytic choriomenengitis virus, a Marburg virus, a measles virus, a mumps virus, a Nipah virus, a norovirus, a Norwalk virus, an orthoreovirus, a parainfluenza virus, a parvovirus, a poliovirus, a rabies virus, a reovirus, a respiratory syncytial virus, rhinovirus, a Rift Valley fever virus, a rotavirus, rubella virus, a St Louis encephalitis virus, a variola major virus, a variola minor virus, a vericella-zoster virus, a West Nile virus, a western equine encephalitis virus, or a yellow fever virus.

III. Methods of Making Antibodies and Polypeptides

Methods of making monoclonal antibodies are known in the art. One method which may be employed is the method of Kohler, G. et al. (1975) "*Continuous Cultures Of Fused*

Cells Secreting Antibody Of Predefined Specificity," Nature 256:495-497 or a modification thereof. Typically, monoclonal antibodies are developed in mice, rats or rabbits. The antibodies are produced by immunizing mice, rats or rabbits with an immunogenic amount of cells, cell extracts, or protein preparations that contain the desired viral epitope or desired activating receptor (e.g., FcγRIIA, FcγRIIA, FcγRIIC, CD3, TCR, CD4, CD2, CD16, and NKG2D, etc.) of an immune effector cell or the protein present on the surface of an immune effector cell that expresses such an activating receptor of an immune cell that is of interest. The immunogen can be, but is not limited to, primary cells, cultured cell lines, cancerous cells, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi. In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant).

In one embodiment, monoclonal antibodies that bind to a desired viral epitope or a desired activating receptor of an immune effector cell or a protein present on the surface of an immune effector cell that expresses such an activating receptor are obtained using host cells that over-express such molecules To monitor the antibody response, a small biological sample (e.g., blood) may be obtained from the human patient or, more preferably, a non-human mammal and tested for antibody titer against the immunogen. The spleen and/or several large lymph nodes of such non-human mammal can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen, using, for example, FACS (fluorescence activated cell sorting) or immunohistochemistry (IHC) screening. The selected monoclonal antibody-secreting hybridomas are then cultured either in vitro (e.g., in tissue culture bottles or hollow fiber reactors), or in vivo (e.g., as ascites in mice).

As another alternative to the cell fusion technique, Epstein-Barr Virus (EBV)-immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, existing monoclonal antibodies and any other equivalent antibodies that are immunospecific for a desired viral epitope or a desired activating receptor of an immune effector cell or a protein present on the surface of an immune effector cell that expresses such an activating receptor can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use.

The polynucleotide sequence of such antibodies may be used for genetic manipulation to generate the bispecific molecules of the invention as well as a chimeric antibody, a humanized antibody, or a canonized antibody, to improve the affinity, or other characteristics of the antibody. The general principle in humanizing or caninizing an antibody involves retaining the basic sequence of the antigen-binding portion of the antibody, while swapping the non-human or non-canine remainder of the antibody with human antibody sequences or canine antibody sequences. There are four general steps to humanize or caninize a monoclonal antibody. These are: (1) determining the nucleotide and predicted amino acid sequence of the starting antibody light and heavy variable domains (2) designing the humanized antibody or canonized antibody, i.e., deciding which antibody framework region to use during the humanizing or canonizing process (3) the actual humanizing or canonizing methodologies/techniques and (4) the transfection and expression of the humanized antibody. See, for example, U.S. Pat. Nos. 4,816,567; 5,807,715; 5,866,692; and 6,331,415.

Single chain variable region fragments ("scFv") are made by linking light and/or heavy chain variable regions by using a short linking peptide. Bird et al. (1988) ("Single-Chain Antigen-Binding Proteins," Science 242:423-426) describes example of linking peptides which bridge approximately 3.5 nm between the carboxy terminus of one variable region and the amino terminus of the other variable region. Linkers of other sequences have been designed and used (Bird et al. (1988) "Single-Chain Antigen-Binding Proteins," Science 242:423-426). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The invention includes modifications to the bispecific molecules of the invention that do not significantly affect their properties and variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the polypeptides and antibodies of this invention. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of an antibody produced from a publicly-deposited hybridoma. For purposes of this invention, an antibody fusion protein contains one or more polypeptide domains that specifically bind to a desired viral epitope or a desired activating receptor of an immune effector cell or a protein present on the surface of an immune effector cell that expresses such an activating receptor and another amino acid sequence to which it is not attached in the native molecule, for example, a heterologous sequence or a homologous sequence from another region.

An anti-viral, anti-activating receptor, or anti-protein present on the surface of an immune effector cell that expresses such an activating receptor polypeptide, and other agonists, antagonists and modulators can be created by methods known in the art, for example, synthetically or recombinantly. One method of producing such peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see, e.g., Kelley, R. F. et al. (1990) In: GENETIC ENGINEERING PRINCIPLES AND METHODS, Setlow, J. K. Ed., Plenum Press, N.Y., vol. 12, pp 1-19; Stewart, J. M et al. (1984) SOLID PHASE PEPTIDE SYNTHESIS, Pierce Chemical Co., Rockford, Ill.; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "Solid Phase Synthesis," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids,*" Proc. Natl. Acad. Sci. (U.S.A.) 82(15):5131-5135; Ganesan, A. (2006) "*Solid-Phase Synthesis In The Twenty-First Century,*" Mini Rev. Med. Chem. 6(1):3-10).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "*Production Of Antibodies And Antibody Fragments In Plants,*" Vaccine 19:2756; Lonberg, N. et al. (1995) "*Human Antibodies From Transgenic Mice,*" Int. Rev. Immunol 13:65-93; and Pollock et al. (1999) "*Transgenic Milk As A Method For The Production Of Recombinant Antibodies,*" J. Immunol Methods 231:147-157). Suitable methods for making derivatives of antibodies, e.g., humanized, single chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology,*" Annu. Rev. Immunol. 12.433-455).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified proteins or portions thereof for cells expressing the antibody or protein of interest. The "panning" procedure may be conducted by obtaining a cDNA library from tissues or cells that express or overexpress the desired cDNAs in a second cell type, and screening the transfected cells of the second cell type for a specific binding to the desired protein. Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System,*" Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation,*" Endocrinol. 140:5841-5854).

cDNAs encoding antibodies, and other peptide agonists, antagonists and modulators can be obtained by reverse transcribing the mRNAs from a particular cell type according to standard methods in the art. Specifically, mRNA can be isolated using various lytic enzymes or chemical solutions according to the procedures set forth in Sambrook et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, more preferably 20-fold higher, more preferably 50-fold higher, more preferably 100-fold higher than that of the corresponding endogenous antibody or protein of interest, if present, in the host cells. Screening the host cells for a specific binding to a desired protein is preferably effected by an immunoassay or FACS. A cell over-expressing the antibody or protein of interest can be identified in this way.

Various techniques are also available which may now be employed to produce mutant peptide agonists, antagonists, and modulators which encodes for additions, deletions, or changes in amino acid sequence of the resultant protein relative to the parent peptide agonist, antagonist or modulator molecule.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, such a polypeptide could be produced by an automated polypeptide synthesizer employing the solid phase method.

IV. Methods for Screening Polypeptides and Monoclonal Antibodies

Several methods may be used to screen polypeptides and monoclonal antibodies that bind to a desired viral epitope or a desired activating receptor of an immune effector cell or a protein present on the surface of an immune effector cell that expresses such an activating receptor. It is understood that "binding" refers to biologically or immunologically relevant specific binding, and does not refer to non-specific binding that may occur, for example, when an immunoglobulin is used at a very high concentration against a non-specific target. In one embodiment, monoclonal antibodies are screened for binding to desired proteins or epitopes using standard screening techniques. In this manner, monoclonal antibodies may be obtained. The preferred hybridomas of the present invention that produce antibodies directed against an activating receptor of an immune effector cell are those that produce antibodies against the activating receptors: CD3, TCR, CD4, CD2, CD16, and NKG2D.

Additional monoclonal antibodies that bind to a desired activating receptor of an immune effector cell or a protein present on the surface of an immune effector cell that expresses such an activating receptor may be identified. For this purpose, monoclonal antibodies are screened for their differential ability to bind to such epitopes or proteins but not to other epitopes or proteins. One method that may be employed for screening is immunohistochemistry (IHC). Standard immunohistochemical techniques are known to those of average skill in the art. See, for example, ANIMAL CELL CULTURE METHODS (J. P. Mather and D. Barnes, eds., Academic Press, NY, Vol. 57, Ch. 18 and 19, pp. 314-350, 1998). Biological samples (e.g., tissues) may be obtained from biopsies, autopsies, or necropsies. To ascertain if an epitope is present only on the surface of an immune effector cell, antibodies that bind to potential epitopes may be used to detect immune effector cells. The tissue can be embedded in a solid or semi-solid substance that prevents damage during freezing (e.g., agarose gel or OCT) and then sectioned for staining. Tissues from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas.

Any of several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzedine, DAB). One alternative method that may be used is polyclonal mirror image complementary antibodies or polyMICA™ (polyclonal Mirror Image Complementary Antibodies; The Binding Site Limited, Birmingham, UK; Mangham, D. C. et al. (1999) "*A Novel Immunohistochemical Detection System Using Mirror Image Complementary Antibodies (MICA)*," Histopathology 35(2):129-33). The PolyMICA™ technique can be used to test binding of primary antibodies to normal and infected tissue. Several kinds of polyMICA™ Detection kits are commercially available: Product No. HK004.D is a polyMICA™ Detection kit which uses DAB chromagen; Product No. HK004.A is a polyMICA™ Detection kit which uses AEC chromagen. Alternatively, the primary antibody may be directly labeled with the detectable marker.

The first step in IHC screening to select for an appropriate antibody is the binding of primary antibodies raised in mice (e.g., anti-activating receptor antibodies) to one or more immunogens (e.g., cells or tissue samples). In one embodiment, the tissue sample is sections of frozen tissue from different organs. The cells or tissue samples can comprise either infected cells or non-infected cells.

Frozen tissues can be prepared, sectioned, with or without fixation, and IHC performed by any of a number of methods known to one familiar with the art (see, for example, Stephan et al. (1999) "*Distribution And Function Of The Adhesion Molecule BEN During Rat Development*," Dev. Biol. 212:264-277 and Stephan et al. (1999) "*Selective Cloning Of Cell Surface Proteins Involved In Organ Development: Epithelial Glycoprotein Is Involved In Normal Epithelial Differentiation*," Endocrinology 140:5841-5854).

V. Methods of Characterizing the Antibodies of the Present Invention

Any of several methods can be used to characterize the antibodies of the present invention. One method is to identify the epitope to which it binds. Epitope mapping is commercially available from various sources, for example, Pepscan Systems (Lelystad, The Netherlands). Epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch.

Peptides of varying lengths (e.g., preferably at least 4-6 amino acids long) can be isolated or synthesized (e.g., recombinantly) and used for binding assays with an antibody. The epitope to which the antibody binds can be determined in a systematic screening by using overlapping peptides derived from the extracellular sequence and determining binding by antibody.

Yet another method that can be used to characterize an antibody of the present invention is to use competition assays with other antibodies known to bind to the same antigen, i.e., to determine if the antibodies bind to the same epitope as other antibodies. Examples of commercially available antibodies to a desired viral epitope or a desired activating receptor of an immune effector cell or a protein present on the surface of an immune effector cell that expresses such an activating receptor may be available and may be identified using the binding assays taught herein. Competition assays are well known to those of skill in the art, and such procedures and illustrative data are detailed further in the Examples. Antibodies can be further characterized by the tissues, type of virus or type of immune cell to which they bind.

As discussed above, a central aspect of antibodies of the present invention relates to their ability to bind a desired viral epitope or a desired activating receptor of an immune effector cell or a protein present on the surface of an immune effector cell that expresses such an activating receptor. Such antibodies may be readily identified by screening among human effector cell-reactive antibodies or antibodies that bind to desired viral particles. Non-limiting examples of such antibodies that bind to a desired activating receptor of an immune effector cell include anti-CD3 antibodies OKT3, M291, YTH12.5, anti-CD3 antibody 1 and anti-CD3 antibody 2; anti-TCR antibody BMA031; anti-CD8 antibody TRX2; anti-CD4 antibody TRX1; anti-CD2 antibody Lo-CD2a (ATCC Accession No: 11423); anti-CD16 antibody 3G8 and A9; anti-NKG2D antibody KYK 2.0.

VI. Preferred Compositions of the Present Invention

The present invention encompasses compositions, including pharmaceutical compositions, comprising the bispecific molecules of the invention, polypeptides derived from such bispecific molecules, polynucleotides comprising sequences encoding such bispecific molecules or polypeptides, and other agents as described herein.

With respect to antibodies that bind to a desired viral epitope, preferred antibodies include those that bind to epitopes of an adenovirus, an adeno-associated virus, a B virus (macacine herpesvirus I), a BK virus, a bunyavirus, a chikungunya virus, a cocksackie virus, a coronavirus (e.g., M protein, etc.), a cytomegalovirus, an eastern equine encephalitis virus, an ebola virus, an enterovirus, an Epstein-Barr virus (e.g., LMP-1, LMP-2, etc.), a hantavirus, a hepatitis A virus, a hepatitis B virus, a hepatitis C virus, a hepatitis D virus, a hepatitis E virus, a herpes simplex virus 1, a herpes simplex virus 2, a human foamy virus, a human herpes virus 3, a human herpes virus 5, a human herpes virus 6, a human herpes virus 7, a human immunodeficiency virus (e.g., env, etc.), a human papillomavirus (e.g., E6, E7, etc.), a human β-lymphotropic virus, a human T-cell leukemia virus I, a human T-cell leukemia virus II, an influenza virus (e.g., $M_2$ protein, etc.), a JC virus, a JEV, a Kaposi's sarcoma-associated herpesvirus, a Lassa virus, a lymphocytic choriomenengitis virus, a Marburg virus, a measles virus, a mumps virus, a Nipah virus, a norovirus, a Norwalk virus, an orthoreovirus, a parainfluenza virus, a parvovirus, a poliovirus, a rabies virus, a reovirus, a respiratory syncytial virus (e.g., M protein, etc.), rhinovirus, a Rift Valley fever virus, a rotavirus, rubella virus, a St Louis encephalitis virus, a variola major virus, a variola minor virus, a vericella-zoster virus, a West Nile virus, a western equine encephalitis virus, or a yellow fever virus. Such antibodies are available commercially from a wide number of sources, or can be obtained by immunizing mice or other animals (including for the production of monoclonal antibodies) with such viruses.

With respect to antibodies that bind to a desired activating receptor of an immune effector cell, preferred antibodies include anti-CD3 antibodies OKT3, M291, YTH12.5, anti-CD3 antibody 1 and anti-CD3 antibody 2; anti-TCR Antibody BMA031; anti-CD8 antibody TRX2; anti-CD4 antibody TRX1; anti-CD2 antibody Lo-CD2a (ATCC Accession No: 11423); anti-CD16 antibody 3G8 and A9; anti-NKG2D antibody KYK 2.0. The amino acid sequences of the variable light chain and variable heavy chain of these antibodies are shown below. Those of skill in the art will therefore be able to construct bispecific molecules having such CDRs, as well as antibodies and derivatives thereof, including humanized derivatives thereof, capable of binding to the epitopes recognized by these antibodies.

```
Anti-CD3 Antibodies
OKT3
OKT3 Light Chain Variable Region (CDRs shown underlined):
                                                    (SEQ ID NO: 1)
QIVLTQSPAI MSASPGEKVT MTCSASSSVS YMNWYQQKSG TSPKRWIYDT

SKLASGVPAH FRGSGSGTSY SLTISGMEAE DAATYYCQQW SSNPFTFGSG

TKLEINR

OKT3 Heavy Chain Variable Region (CDRs shown underlined):
                                                    (SEQ ID NO: 2)
QVQLQQSGAE LARPGASVKM SCKASGYTFT RYTMHWVKQR PGQGLEWIGY

INPSRGYTNY NQKFKDKATL TTDKSSSTAY MQLSSLTSED SAVYYCARYY
```

```
DDHYCLDYWG QGTTLTVSSA KTTAPSVYPL APVCGDTTGS SVTLGCLVKG

YFPEPVTLTW NSGSLSSGVH TFPAVLQSDL YTLSSSVTVT SS

M291
M291 Light Chain Variable Region (CDRs shown underlined):
                                            (SEQ ID NO: 3)
DIVLTQSPAI MSASPGEKVT MTCSASSSVS YMNWYQQKSG TSPKRWTYDT

SKLASGVPAR FSGSGSGTSY SLTISSMEAE DADTYYCQQW SSNPPTFGSG

TKLEIK

M291 Heavy Chain Variable Region (CDRs shown underlined):
                                            (SEQ ID NO: 4)
QVQLQQSGAE LARPGASVKM SCKASGYTFI SYTMHWVKQR PGQGLEWIGY

INPRSGYTHY NQKLKDKATL TADKSSSSAY MQLSSLTSED SAVYYCARSA

YYDYDGFAYW GQGTLVTVSA

YTH12.5
YTH12.5 Light Chain Variable Region (CDRs shown underlined):
                                            (SEQ ID NO: 5)
MGWSCIILFL VATATGVHSD IQLTQPNSVS TSLGSTVKLS CTLSSGNIEN

NYVHWYQLYE GRSPTTMIYD DDKRPDGVPD RFSGSIDRSS NSAFLTIHNV

AIEDEAIYFC HSYVSSFNVF GGGTKLTVLR

YTH12.5 Heavy Chain Variable Region (CDRs shown underlined):
                                            (SEQ ID NO: 6)
MGWSCIILFL VATATGVHSE VQLLESGGGL VQPGGSLRLS CAASGFTFSS

FPMAWVRQAP GKGLEWVSTI STSGGRTYYR DSVKGRFTIS RDNSKNTLYL

QMNSLRAEDT AVYYCAKFRQ YSGGFDYWGQ GTLVTVSS

Anti-CD3 Antibody 1
Anti-CD3 Antibody 1 Light Chain Variable Region (CDRs shown
underlined)::
                                            (SEQ ID NO: 7)
QVVLTQSPAI MSAFPGEKVT MTCSASSSVS YMNWYQQKSG TSPKRWIYDS

SKLASGVPAR FSGSGSGTSY SLTISSMETE DAATYYCQQW SRNPPTFGGG

TKLQITR

Anti-CD3 Antibody 1 Heavy Chain Variable Region (CDRs shown
underlined)::
                                            (SEQ ID NO: 8)
QVQLQQSGAE LARPGASVKM SCKASGYTFT RSTMHWVKQR PGQGLEWIGY

INPSSAYTNY NQKFKDKATL TADKSSSTAY MQLSSLTSED SAVYYCASPQ

VHYDYNGFPY WGQGTLVTVS S

Anti-CD3 Antibody 2
Anti-CD3 Antibody 2 Light Chain Variable Region (CDRs shown
underlined):
                                            (SEQ ID NO: 9)
QAVVTQESAL TTSPGETVTL TCRSSTGAVT TSNYANWVQE KPDHLFTGLI

GGTNKRAPGV PARFSGSLIG DKAALTITGA QTEDEAIYFC ALWYSNLWVF

GGGTKLTVLG
Anti-CD3 Antibody 2 Heavy Chain Variable Region (CDRs shown
underlined):
                                            (SEQ ID NO: 10)
EVQLVESGGG LVQPKGSLKL SCAASGFTFN TYAMNWVRQA PGKGLEWVAR

IRSKYNNYAT YYADSVKDRF TISRDDSQSI LYLQMNNLKT EDTAMYYCVR

HGNFGNSYVS WFAYWGQGTL VTVSA
```

-continued

```
Anti-TCR Antibodies
BMA031
BMA031 Light Chain Variable Region (CDRs shown underlined):
                                          (SEQ ID NO: 11)
QIVLTQSPAI MSASPGEKVT MTCSATSSVS YMHWYQQKSG TSPKRWIYDT

SKLASGVPAR FSGSGSGTSY SLTISSMEAE DAATYYCQQW SSNPLTFGAG

TKLELK

BMA031 Heavy Chain Variable Region (CDRs shown underlined):
                                          (SEQ ID NO: 12)
EVQLQQSGPE LVKPGASVKM SCKASGYKFT SYVMHWVKQK PGQGLEWIGY

INPYNDVTKY NEKFKGKATL TSDKSSSTAY MELSSLTSED SAVHYCARGS

YYDYDGFVYW GQGTLVTVSA

Anti-CD8 Antibodies
TRX2
TRX2 Light Chain Variable Region (CDRs shown underlined):
                                          (SEQ ID NO: 13)
DIQMTQSPSS LSASVGDRVT ITCKGSQDIN NYLAWYQQKP GKAPKLLIYN

TDILHTGVPS RFSGSGSGTD FTFTISSLQP EDIATYYCYQ YNNGYTFGQG

TKVEIK

TRX2 Heavy Chain Variable Region (CDRs shown underlined):
                                          (SEQ ID NO: 14)
QVQLVESGGG VVQPGRSLRL SCAASGFTFS DFGMNWVRQA PGKGLEWVAL

IYYDGSNKFY ADSVKGRFTI SRDNSKNTLY LQMNSLRAED TAVYYCAKPH

YDGYYHFFDS WGQGTLVTVSS

Anti-CD4 Antibodies
TRX1
TRX1 Light Chain Variable Region (CDRs shown underlined):
                                          (SEQ ID NO: 15)
DIVMTQSPDS LAVSLGERAT INCKASQSVD YDGDSYMNWY QQKPGQPPKL

LIYVASNLES GVPDRFSGSG SGTDFTLTIS SLQAEDVAVY YCQQSLQDPP

TFGGGTKVEI KR

TRX1 Heavy Chain Variable Region (CDRs shown underlined):
                                          (SEQ ID NO: 16)
QVQLVQSGAE VKKPGASVKV SCKASGYTFT AYVISWVRQA PGQGLEWMGE

IYPGSGSSYY NEKFKGRVTM TRDTSTSTVY MELSSLRSED TAVYYCARSG

DGSRFVYWGQ GTLVTVSS

Anti-CD2 Antibodies
Lo-CD2a (ATCC Accession No: 11423)
Lo-CD2a Light Chain Variable Region (CDRs shown underlined):
                                          (SEQ ID NO: 17)
DVVLTQTPPT LLATIGQSVS ISCRSSQSLL HSSGNTYLNW LLQRTGQSPQ

PLIYLVSKLE SGVPNRFSGS GSGTDFTLKI SGVEAEDLGV YYCMQFTHYP

YTFGAGTKLE LK

Lo-CD2a Heavy Chain Variable Region (CDRs shown underlined):
                                          (SEQ ID NO: 18)
EVQLQQSGPE LQRPGASVKL SCKASGYIFT EYYMYWVKQR PKQGLELVGR

IDPEDGSIDY VEKFKKKATL TADTSSNTAY MQLSSLTSED TATYFCARGK

FNYRFAYWGQ GTLVTVSS
```

-continued

```
Anti-CD16 Antibodies
3G8
3G8 Light Chain Variable Region (CDRs shown underlined):
                                              (SEQ ID NO: 19)
DTVLTQSPAS LAVSLGQRAT ISCKASQSVD FDGDSFMNWY QQKPGQPPKL

LIYTTSNLES GIPARFSASG SGTDFTLNIH PVEEEDTATY YCQQSNEDPY

TFGGGTKLEI K

3G8 Heavy Chain Variable Region (CDRs shown underlined):
                                              (SEQ ID NO: 20)
QVTLKESGPG ILQPSQTLSL TCSFSGFSLR TSGMGVGWIR QPSGKGLEWL

AHIWWDDDKR YNPALKSRLT ISKDTSSNQV FLKIASVDTA DTATYYCAQI

NPAWFAYWGQ GTLVTVSA

A9
A9 Light Chain Variable Region (CDRs shown underlined):
                                              (SEQ ID NO: 21)
DIQAVVTQES ALTTSPGETV TLTCRSNTGT VTTSNYANWV QEKPDHLFTG

LIGHTNNRAP GVPARFSGSL IGDKAALTIT GAQTEDEAIY FCALWYNNHW

VFGGGTKLTVL

A9 Heavy Chain Variable Region (CDRs shown underlined):
                                              (SEQ ID NO: 22)
QVQLQQSGAE LVRPGTSVKI SCKASGYTFT NYWLGWVKQR PGHGLEWIGD

IYPGGGYTNY NEKFKGKATV TADTSSRTAY VQVRSLTSED SAVYFCARSA

SWYFDVWGAR TTVTVSS

Anti-NKG2D Antibodies
KYK 1.0
KYK 1.0 Light Chain Variable Region (CDRs shown underlined):
                                              (SEQ ID NO: 23)
QPVLTQPSSV SVAPGETARI PCGGDDIETK SVHWYQQKPG QAPVLVIYDD

DDRPSGIPER FFGSNSGNTA TLSISRVEAG DEADYYCQVW DDNNDEWVFG

GGTQLTVL

KYK 1.0 Heavy Chain Variable Region (CDRs shown underlined):
                                              (SEQ ID NO: 24)
EVQLVESGGG VVQPGGSLRL SCAASGFTFS SYGMHWVRQA PGKGLEWVAF

IRYDGSNKYY ADSVKGRFTI SRDNSKNTKY LQMNSLRAED TAVYYCAKDR

FGYYLDYWGQ GTLVTVSS

KYK 2.0
KYK 2.0 Light Chain Variable Region (CDRs shown underlined):
                                              (SEQ ID NO: 25)
QSALTQPASV SGSPGQSITI SCSGSSSNIG NNAVNWYQQL PGKAPKLLIY

YDDLLPSGVS DRFSGSKSGT SAFLAISGLQ SEDEADYYCA AWDDSLNGPV

FGGGTKLTVL

KYK 2.0 Heavy Chain Variable Region (CDRs shown underlined):
                                              (SEQ ID NO: 26)
QVQLVESGGG LVKPGGSLRL SCAASGFTFS SYGMHWVRQA PGKGLEWVAF

IRYDGSNKYY ADSVKGRFTI SRDNSKNTLY LQMNSLRAED TAVYYCAKDR

GLGDGTYFDY WGQGTTVTVS S
```

The invention further provides for conjugates of any antibody, agonist or antagonist that binds a desired viral epitope or a desired activating receptor of an immune effector cell or a protein present on the surface of an immune effector cell that expresses such an activating receptor.

These conjugates include agonists, antagonists or modulators covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (Eds) AFFINITY CHROMATOGRAPHY: A PRACTICAL APPROACH, IRL Press (1985); Lowe, "*An Introduc-*

*tion to Affinity Chromatography*", in Work et al. (Eds) LABORATORY TECHNIQUES IN BIOCHEMISTRY AND MOLECULAR BIOLOGY, Vol. 7, Part II, North-Holland (1979); Porath et al., "*Biospecific Affinity Chromatography*", in Neurath, H. et al. (Eds), THE PROTEINS, 3rd ed., Vol. 1, pp. 95-178 (1975); and Schott, H. AFFINITY CHROMATOGRAPHY, Marcel Dekker, Inc. NY (1984).

The antibody, agonist or antagonist that binds a desired viral epitope or a desired activating receptor of an immune effector cell or a protein present on the surface of an immune effector cell that expresses such an activating receptor are further identified and characterized by an ability to specifically bind to molecules that are expressed on the surfaces of human and/or non-human companion animal cells, and optionally any (one or more) of the following criteria:

(a) an ability to competitively inhibit preferential binding of a known antibody to such epitope or protein, including the ability to preferentially bind to the same epitope to which the original antibody preferentially binds;

(b) an ability to bind to a portion of such epitope or protein that is exposed on the surfaces of living human and/or non-human mammalian cells in vitro or in vivo;

(c) an ability to deliver a chemotherapeutic agent to a human and/or non-human mammalian cell expressing such epitope or protein on its surface; and/or (f) an ability to deliver a therapeutic agent or detectable marker into a human and/or non-human mammalian cell expressing such epitope or protein on its surface.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity-determining region (CDR) of the antibody.

VII. Bi-Specific Diabodies (Dual Affinity Retargeting Reagents)

As discussed above, the present invention additionally encompasses "bispecific diabody molecules (dual affinity retargeting reagent) molecules that comprise at least two polypeptide chains which form at least two epitope binding sites, at least one of which specifically binds to an epitope of a protein expressed on the surface of an immune effector cell, wherein the immune effector cell expresses an activating receptor of an effector cell, and at least one of which specifically binds to an epitope of an antigen expressed by a cell infected with a virus; wherein the antigen is detectably present on the cell infected by the virus at a level that is greater than the level at which the antigen is detected on the virus by the bispecific molecule.

In preferred embodiments (FIG. 1A), the first polypeptide chain of the diabody comprises:

(i) a domain (A) comprising a binding region of a light chain variable domain of a first immunoglobulin (VL1) specific for an epitope (1);

(ii) a domain (B) comprising a binding region of a heavy chain variable domain of a second immunoglobulin (VH2) specific for an epitope (2); and (iii) a domain (C).

The second polypeptide chain of such a diabody comprises:

(i) a domain (D) comprising a binding region of a light chain variable domain of the second immunoglobulin (VL2) specific for epitope (2);

(ii) a domain (E) comprising a binding region of a heavy chain variable domain of the first immunoglobulin (VH1) specific for epitope (1); and (iii) a domain (F).

Epitope (1) above can refer to an epitope of a viral protein, and epitope (2) to an epitope of an activating receptor or an epitope of a protein expressed on the surface of an immune effector cell that expresses an activating receptor. Alternatively, Epitope (1) above can refer to an epitope of an activating receptor or an epitope of a protein expressed on the surface of an immune effector cell that expresses an activating receptor, and epitope (2) to an epitope of a viral protein.

The diabody domains (A) and (B) do not associate with one another to form an epitope binding site. Similarly, the diabody domains (D) and (E) do not associate with one another to form an epitope binding site. Rather, diabody domains (A) and (E) associate to form a binding site that binds epitope (1); said diabody domains (B) and (D) associate to form a binding site that binds said epitope (2). Domains (C) and (F) are covalently associated together. Methods for forming diabody molecules and specific orientations of the diabody domains are disclosed in US Patent Publications Nos. 2010/0174053, US 2009/0060910 and US 2007/0004909.

Each polypeptide chain of the diabody molecule comprises a VL domain and a VH domain, which are covalently linked such that the domains are constrained from self-assembly. Interaction of two of the polypeptide chains will produce two VL-VH pairings, forming two epitope binding sites, i.e., a bivalent molecule. Neither the VH or VL domain is constrained to any position within the polypeptide chain, i.e., restricted to the amino (N) or carboxy (C) terminus, nor are the domains restricted in their relative positions to one another, i.e., the VL domain may be N-terminal to the VH domain and vice-versa; however, it is preferred that the VL domain may be N-terminal to the VH domain. The only restriction is that a complimentary polypeptide chain be available in order to form functional diabodies. Where the VL and VH domains are derived from the same antibody, the two complimentary polypeptide chains may be identical. For example, where the binding domains are derived from an antibody specific for epitope A (i.e., the binding domain is formed from a $VL_A$-$VH_A$ interaction), each polypeptide will comprise a $VH_A$ and a $VL_A$. Homodimerization of two polypeptide chains of the antibody will result in the formation two $VL_A$-$VH_A$ binding sites, resulting in a bivalent monospecific antibody (FIG. 1A). Where the VL and VH domains are derived from antibodies specific for different antigens, formation of a functional bispecific diabody requires the interaction of two different polypeptide chains, i.e., formation of a heterodimer. For example, for a bispecific diabody, one polypeptide chain will comprise a $VL_A$ and a $VL_B$; homodimerization of said chain will result in the formation of two $VL_A$-$VH_B$ binding sites, either of no binding or of unpredictable binding. In contrast, where two differing polypeptide chains are free to interact, e.g., in a recombinant expression system, one comprising a $VL_A$ and a $VH_B$ and the other comprising a $VL_B$ and a $VH_A$, two differing binding sites will form: $VL_A$-$VH_A$ and $VL_B$-$VH_B$. For all diabody polypeptide chain pairs, the possibly of misalignment or mis-binding of the two chains is a possibility, i.e., interaction of VL-VL or VH-VH domains; however, purification of functional diabodies is easily managed based on the immunospecificity of the properly dimerized binding site using any affinity based method known in the art or exemplified herein, e.g., affinity chromatography.

One or more of the polypeptide chains of the diabody may optionally comprise an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In preferred embodiments, the Fc domain (or portion thereof) is derived from IgG. In specific embodiments, the IgG isotype is IgG1, IgG2, IgG3 or IgG4 or an allotype thereof. In one embodiment, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from IgG1 and the CH3 domain derived from IgG2, etc.). The Fc domain may be engineered into a polypeptide chain comprising the diabody molecule of the invention in any position relative to other domains or portions of said polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The Fc domains in the polypeptide chains of the diabody molecules preferentially dimerize, resulting in the formation of a diabody molecule that exhibits immunoglobulin-like properties, e.g., Fc-FcγR, interactions. Fc comprising diabodies may be dimers, e.g., comprised of two polypeptide chains, each comprising a VH domain, a VL domain and an Fc domain. Dimerization of said polypeptide chains results in a bivalent diabody comprising an Fc domain, albeit with a structure distinct from that of an unmodified bivalent antibody. Such diabody molecules will exhibit altered phenotypes relative to a wild-type immunoglobulin, e.g., altered serum half-life, binding properties, etc. In other embodiments, diabody molecules comprising Fc domains may be tetramers. Such tetramers comprise two 'heavier' polypeptide chains, i.e., a polypeptide chain comprising a VL, a VH and an Fc domain, and two 'lighter' polypeptide chains, i.e., polypeptide chain comprising a VL and a VH. The lighter and heavier chains interact to form a monomer, and said monomers interact via their unpaired Fc domains to form an Ig-like molecule. Such an Ig-like diabody is tetravalent and may be monospecific, bispecific or tetraspecific.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to increase the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety.

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain modifications identified as altering effector function are disclosed above. A large number of substitutions in the Fc domain of human IgG1 that increase binding to activating receptors (e.g., FcγRIIA (CD16A) and reduce binding to inhibitory receptors (e.g., FcγRIIB (CD32B) are known in the art and are described in Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890. Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

The present invention also encompasses molecules comprising a hinge domain. The hinge domain may be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotype thereof. Said hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of said polypeptide chain. In certain embodiments, a polypeptide chain of the invention comprises a hinge domain, which hinge domain is at the C-terminus of the polypeptide chain, wherein said polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chain.

Each domain of the polypeptide chain of the diabody, i.e., the VL, VH and Fc domain may be separated by a peptide linker. The peptide linker may be 0, 1, 2, 3, 4, 5, 6, 7, 8, or 9. amino acids. In certain embodiments the amino acid linker sequence is GGGSGGGG (SEQ ID NO:27) encoded by the nucleic acid sequence ggaggcggat ccggaggcgg aggc (SEQ ID NO:28). The polypeptide chains of the diabody molecule may be engineered to comprise at least one cysteine residue that will interact with a counterpart cysteine residue on a second polypeptide chain of the diabody to form an inter-chain disulfide bond. Such interchain disulfide bonds serve to stabilize the diabody molecule, thereby improving expression and recovery in recombinant systems, resulting in a stable and consistent formulation and improving the stability of the isolated and/or purified product in vivo. The cysteine residue may be introduced as a single amino acid or as part of larger amino-acid sequence, e.g. a hinge domain, in any portion of the polypeptide chain. In a specific embodiment, the cysteine residue may be engineered to occur at the C-terminus of the polypeptide chain. In some embodiments, the cysteine residue is introduced into the polypeptide chain within the amino acid sequence LGGC (SEQ ID NO:29). In a specific embodiment, the C-terminus of the polypeptide chains comprising the diabody molecule of the invention comprises the amino acid sequence LGGC (SEQ ID NO:29). In another embodiment, the cysteine residue is introduced into the polypeptide within an amino acid sequence comprising a hinge domain, e.g. EPKSCDKTHTCPP (SEQ ID NO:30) or ESKYGPPCPS (SEQ ID NO:31). In a specific embodiment, the C-terminus of a polypeptide chain of the diabody molecule of the invention comprises the amino acid sequence of an IgG hinge domain, e.g. SEQ ID NO:29 or SEQ ID NO:31. In another embodiment, the C-terminus of a polypeptide chain of a diabody molecule of the invention comprises the amino acid sequence VEPKSC (SEQ ID NO:32), which can be encoded by nucleotide sequence gttgagccca aatcttgt (SEQ ID NO:33). In other embodiments, the cysteine residue in introduced into the polypeptide chain within the amino acid sequence LGGCFNRGEC (SEQ ID NO:34), which can be encoded by the nucleotide sequence ctgggaggct gcttcaacag gggagagtgt (SEQ ID NO:35). In a specific embodiment, the C-terminus of a polypeptide chain comprising the diabody of the invention comprises the amino acid sequence LGGCFNRGEC (SEQ ID NO:34). In yet other embodiments, the cysteine residue in introduced into the polypeptide chain within the amino acid sequence FNRGEC (SEQ ID NO:36), which can be encoded by the nucleotide sequence ttcaacaggg gagagtgt (SEQ ID NO:37). In a specific embodiment, the C-terminus of a polypeptide chain comprising the diabody of the invention comprises the amino acid sequence FNRGEC (SEQ ID NO:36).

In certain embodiments, the diabody molecule comprises at least two polypeptide chains, each of which comprise the amino acid sequence LGGC (SEQ ID NO:29) and are covalently linked by a disulfide bond between the cysteine residues in the LGGC (SEQ ID NO:29) sequences. In certain embodiments, the diabody molecule comprises at least two polypeptide chains, each of which comprise the amino acid sequence GGCGGG (SEQ ID NO:38) and are covalently linked by a disulfide bond between the cysteine residues in the GGCGGG (SEQ ID NO:38) sequences. In another specific embodiment, the diabody molecule comprises at least two polypeptide chains, one of which comprises the sequence FNRGEC (SEQ ID NO:36) while the other comprises a hinge domain (containing at least one cysteine residue), wherein said at least two polypeptide chains are covalently linked by a disulfide bond between the cysteine residue in FNRGEC (SEQ ID NO:36) and a cysteine residue in the hinge domain. In particular aspects, the cysteine residue responsible for the disulfide bond located in the hinge domain is Cys-128 (as numbered according to Kabat EU; located in the hinge domain of an unmodified, intact IgG heavy chain) and the counterpart cysteine residue is Cys-214 (as numbered according to Kabat EU; located at the C-terminus of an unmodified, intact IgG light chain) (Elkabetz et al. (2005) "*Cysteines In CH*1 *Underlie Retention Of Unassembled Ig Heavy Chains,*" J. Biol. Chem. 280:14402-14412). In yet other embodiments, the at least one cysteine residue is engineered to occur at the N-terminus of the amino acid chain. In still other embodiments, the at least one cysteine residue is engineered to occur in the linker portion of the polypeptide chain of the diabody molecule. In further embodiments, the VH or VL domain is engineered to comprise at least one amino acid modification relative to the parental VH or VL domain such that said amino acid modification comprises a substitution of a parental amino acid with cysteine.

In still another aspect of this embodiment, the Domain (C) of the first polypeptide chain comprises the amino acid sequence VEPKSC (SEQ ID NO:32), derived from the hinge domain of a human IgG, and which can be encoded by the nucleotide sequence gttgagccca aatcttgt (SEQ ID NO:33). In another aspect of this embodiment, the Domain (F) of the second polypeptide chain comprises the amino acid sequence VEPKSC (SEQ ID NO:32). In certain aspects of this embodiment, Domain (C) of the first polypeptide chain comprises the C-terminal 6 amino acids of the human kappa light chain, FNRGEC (SEQ ID NO:36); and Domain (F) of the second polypeptide chain comprises the amino acid sequence VEPKSC (SEQ ID NO:32) or a hinge domain. In other aspects of this embodiment, Domain (F) of the second polypeptide chain comprises the C-terminal 6 amino acids of the human kappa light chain, FNRGEC (SEQ ID NO:36); and Domain (C) of the first polypeptide chain comprises the amino acid sequence VEPKSC (SEQ ID NO:32) or a hinge domain.

As will be appreciated in view of the foregoing, the individual polypeptides of a bispecific diabody can form two species of homodimers and one species of heterodimer. In one embodiment of the present invention, a charged polypeptide can be added to the C-terminus of one, or more preferably, both diabody polypeptides. By selecting charged polypeptides of opposite charge for the individual polypeptides of the bispecific diabody, the inclusion of such charged polypeptides favors formation of heterodimers and lessens formation of homodimers. Preferably, a positively charged polypeptide will contain a substantial content of arginine, glutamine, histidine and/or lysine (or mixtures of such amino acids) and a negatively charged polypeptide will contain a substantial content of aspartate or glutamate (or a mixture of such amino acids). Positively charged polypeptides containing a substantial content of lysine and negatively charged polypeptides containing a substantial content of glutamate are particularly preferred. In order to maximize the electrostatic attraction between such opposingly charged polypeptides, it is preferred to employ polypeptides capable of spontaneously assuming a helical conformation.

Figure 1B:
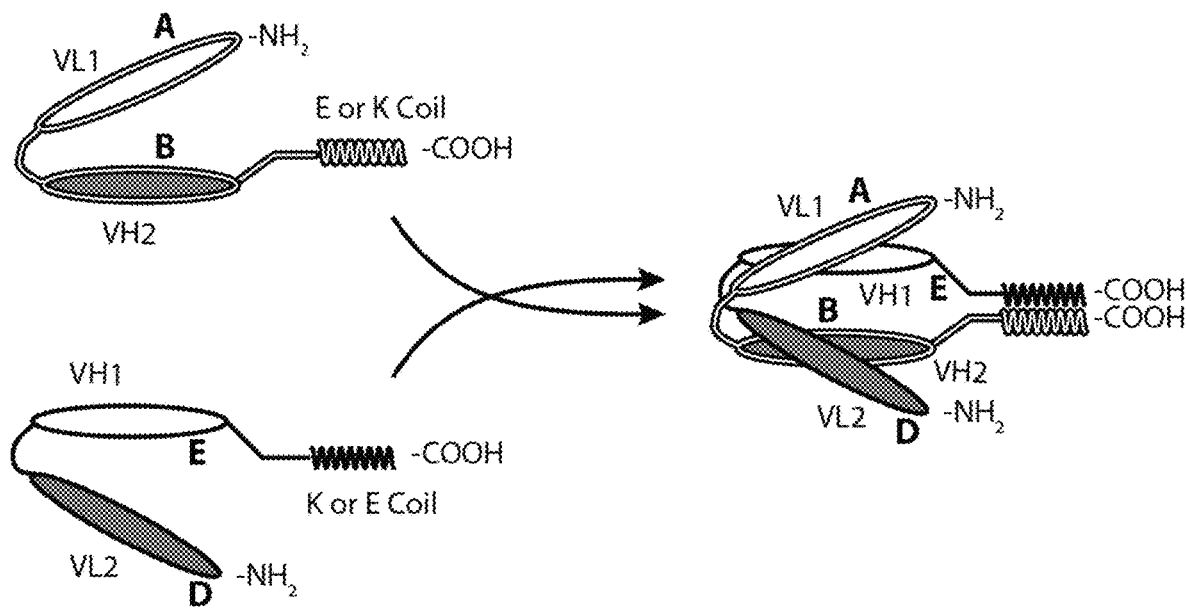

Thus, in a preferred embodiment, a negatively charged, "E-coil" will be appended to one of the polypeptides being used to form a bispecific diabody and a positively charged "K-coil" will be appended to the second of the diabody's polypeptides (FIG. 1B). A particularly preferred E-coil will have the sequence: $(EVAALEK)_4$ [i.e. (SEQ ID NO:39) EVAALEKEVAALEKEVAALEKEVAALEK]. A particularly preferred K-coil will have the sequence: $(KVAALKE)_4$ [i.e. (SEQ ID NO:40) KVAALKEKVAALKEKVAALKEKVAALKE].

A preferred diabody polypeptide possessing such an E-coil will have the general sequence: [VL Domain]-[GGGSGGGG]-[VH Domain]-[$(EVAALEK)_4$]-GGGNS, where VL is the diabody's variable light Ig domain, GGGSGGGG is SEQ ID NO:27, VH is the diabody's variable heavy Ig domain, $(EVAALEK)_4$ is SEQ ID NO:39, and GGGNS is SEQ ID NO:41. A preferred diabody polypeptide possessing such a K-coil will have the general sequence: [VL Domain]-[GGGSGGGG]-[VH Domain]-[$(KVAALKE)_4$]-GGGNS, where VL is the diabody's variable light Ig domain, GGGSGGGG is SEQ ID NO:25, VH is the diabody's variable heavy Ig domain, $(KVAALKE)_4$ is SEQ ID NO:40, and GGGNS is SEQ ID NO:41.

In a further embodiment, Fc-regions can be linked to the E and/or K coils of E-coil or K-coil diabodies. Furthering the separation between the Fc regions and the diabody VH domain of an Fc-containing diabody is desirable in cases in which a less separated arrangement of such domains results in diminished interaction between such domains and their binding ligands or otherwise interferes with diabody assembly. Although separators of any amino acid sequence may be employed, it is preferable to employ separators that form an a helix coils, so as to maximally extend and project the Fc domain away from the variable domains. Because the above-described coiled polypeptides of opposing charge additionally function to promote heterodimer formation, such molecules are particularly preferred separators. Such coil-containing Fc-diabody molecules provide benefits similar to those of Fc-diabodies, including improved serum half-life and effector function recruitment. The above-described E-coil and K-coil polypeptides are particularly preferred for this purpose. Thus, in a preferred embodiment, the E-coil Fc-containing diabody will have the general sequence: [VL Domain]-[GGGSGGGG]-[VH Domain]-[$(EVAALEK)_4$]-GGG-Fc domain starting with D234 (Kabat numbering), where VL is the diabody's variable light Ig domain, GGGSGGGG is SEQ ID NO:27, VH is the diabody's variable heavy Ig domain and $(EVAALEK)_4$ is SEQ ID NO:39. Similarly, in a preferred embodiment, the K-coil Fc-containing diabody will have the general sequence: [VL Domain]-[GGGSGGGG]-[VH Domain]-[$(KVAALKE)_4$]-GGG-Fc domain starting with D234 (Kabat numbering), where VL is the diabody's variable light Ig domain, GGGSGGGG is SEQ ID NO:27, VH is the diabody's variable heavy Ig domain and $(KVAALKE)_4$ is SEQ ID NO:40.

As indicated above, a coil-containing diabody molecule or a coil-containing Fc-containing diabody molecule may contain only a single such coil separator, or it may contain more than one such separators (e.g., two separators, preferably of opposite charge, of which one is linked to each of the VH domain of the diabody's polypeptides). By linking the Fc region to such separator molecule(s), the ability to make bivalent, tetravalent, etc. versions of the Fc-diabody molecules by chain swapping is enhanced. Fc-diabody molecules can thus be produced that form monomers or dimers depending upon whether the Fc domain is linked to one or both of the diabody VH domains.

Figure 1C:
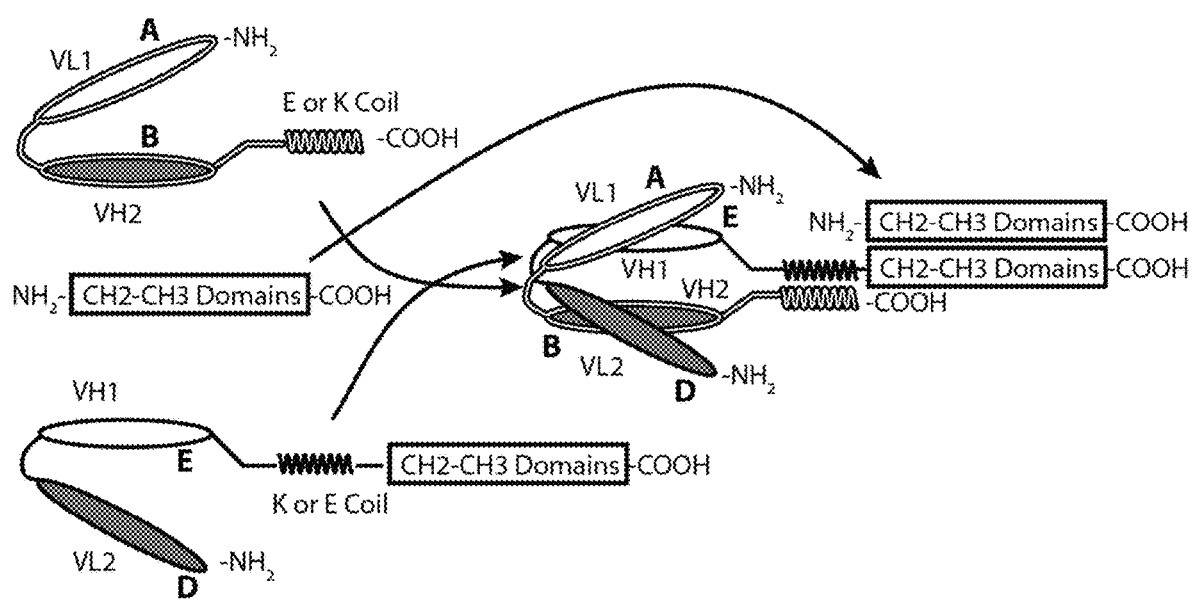

Thus, the invention includes a diabody composed of three polypeptide chains, illustrated in FIG. 1C. The first polypeptide chain comprises (from N-Terminus to C-terminus):
  (i) a domain (A) comprising a binding region of a light chain variable domain of a first immunoglobulin (VL1) specific for an epitope (1);
  (ii) a domain (B) comprising a binding region of a heavy chain variable domain of a second immunoglobulin (VH2) specific for an epitope (2); and
  (iii) an E coil or a K coil.

The second polypeptide chain comprises (from N-Terminus to C-terminus):
  (i) a domain (D) comprising a binding region of a light chain variable domain of the second immunoglobulin (VL2) specific for epitope (2);
  (ii) a domain (E) comprising a binding region of a heavy chain variable domain of the first immunoglobulin (VH1) specific for epitope (1); and
  (iii) a K coil (if the first polypeptide has an E coil) or an E coil (if the first polypeptide has a K coil).

The second polypeptide chain additionally contains a CH2-CH3 region of an Fc region, which may be N-terminal to Domain D, or C-terminal to Domain E.

The third polypeptide chain comprises a CH2-CH3 region of an Fc region

Epitope (1) above refers to an epitope of a viral protein, and epitope (2) to an epitope of an activating receptor or an epitope of a protein expressed on the surface of an immune effector cell that expresses an activating receptor. Alternatively, Epitope (1) above refers to an epitope of an activating receptor or an epitope of a protein expressed on the surface of an immune effector cell that expresses an activating receptor, and epitope (2) to an epitope of a viral protein.

In a preferred embodiment, the second polypeptide chain will contain a knob mutation (T366W) and alanine substitutions at positions 234 and 235. In such preferred embodiment, the third polypeptide chain will contain a hole mutation (T366S, L368A, and Y407V) and an H435R substitution to remove protein A binding ability. The presence of such knob and hole mutations fosters heterodimerization between the respective CH2-CH3 regions of the second and third polypeptide chains.

The bispecific molecules of the present invention can simultaneously bind two separate and distinct epitopes. In preferred embodiments, at least one epitope binding site is specific for a determinant expressed on an immune effector cell (e.g. CD3, CD16, CD32, CD64, T-cell receptor, NKG2D, etc.) which are expressed on T lymphocytes, natural killer (NK) cells or other mononuclear cells. In one embodiment, the diabody molecule binds to the effector cell determinant and also activates said effector cell. In this regard, the bispecific molecules of the invention may exhibit Ig-like functionality independent of whether they further comprise an Fc domain (e.g., as assayed in any effector function assay known in the art or exemplified herein (e.g., ADCC assay). In certain embodiments the bispecific diabody of the invention binds both a viral epitope and an effector cell determinant while activating said cell.

The invention further encompasses incorporation of unnatural amino acids to generate the diabodies of the invention. Such methods are known to those skilled in the art such as those using the natural biosynthetic machinery to allow incorporation of unnatural amino acids into proteins, see, e.g., Wang et al. (2002) "*Expanding The Genetic Code,*" Chem. Comm. 1: 1-11; Wang et al. (2001) "*Expanding The Genetic Code Of Escherichia coli,*" Science, 292: 498-500; van Hest et al. (2001) "*Protein-Based Materials, Toward A New Level Of Structural Control,*" Chem. Comm. 19: 1897-1904, each of which is incorporated herein by reference in its entirety. Alternative strategies focus on the enzymes responsible for the biosynthesis of amino acyl-tRNA, see, e.g., Tang et al. (2001) "*Biosynthesis Of A Highly Stable Coiled-Coil Protein Containing Hexafluoroleucine In An Engineered Bacterial Host,*" J. Am. Chem. Soc. 123(44): 11089-11090; Kiick et al. (2001) "*Identification Of An Expanded Set Of Translationally Active Methionine Analogues In Escherichia coli,*" FEBS Lett. 502(1-2):25-30; each of which is incorporated herein by reference in its entirety. In some embodiments, the invention encompasses methods of modifying a VL, VH or Fc domain of a molecule of the invention by adding or deleting a glycosylation site. Methods for modifying the carbohydrate of proteins are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety.

VIII. Methods of Using the Bispecific Molecules of the Present Invention for Therapeutic Purposes The bispecific molecules of the present invention may be used for therapeutic purposes in humans and/or non-human mammalian animals experiencing, or at risk of, a viral disease. Therapy with such bispecific molecules can involve formation of complexes both in vitro and in vivo as described above. In one embodiment, such bispecific molecules can bind to and reduce the proliferation of viruses associated with such disease. It is understood that the bispecific molecule is administered at a concentration that promotes binding at physiological (e.g., in vivo) conditions. In another embodiment, such bispecific molecules can be used for immunotherapy directed at virally-infected cells (or cells at risk of such infection) of different tissues such as colon, lung, breast, prostate, ovary, pancreas, kidney etc. In another embodiment, such bispecific molecules alone can bind to and reduce cell division of virally infected cells. In another embodiment, such bispecific molecules can bind to virally infected cells and delay their growth. In yet another embodiment, an individual with cancer, or an infectious disease is given palliative treatment with such bispecific molecules. Palliative treatment of such individuals involves treating or lessening the adverse symptoms of the cancer or infectious disease, or iatrogenic symptoms resulting from other treatments given for the disease without directly affecting the disease progression. This includes treatments for easing of pain, nutritional support, sexual problems, psychological distress, depression, fatigue, psychiatric disorders, nausea, vomiting, etc. In one embodiment, the molecules of the present invention are administered therapeutically or prophylactically to patients (e.g., HIV+ patients or cancer patients) to address secondary viral infections (as opposed to HIV or cancer) that occur or may occur in such individuals.

Various formulations of the bispecific molecules of the invention may be used for administration. In some embodiments, bispecific molecules or fragments thereof may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and non-parenteral drug delivery are set forth in REMINGTON: THE SCIENCE AND PRACTICE OF PHARMACY, 21st Edition, Lippincott Williams & Wilkins Publishing (2005). Suitable formulations for oral administration include hard or soft gelatin capsules, pills, tablets, including coated tablets, elixirs, suspensions, syrups or inhalations and controlled release forms thereof. Generally, these agents are formulated for administration by injection (e.g., intraperitoneally, intravenously, subcutaneously, intramuscularly, etc.), although other forms of administration (e.g., oral, mucosal, etc.) can be also used. Accordingly, the bispecific molecules are preferably combined with pharmaceutically acceptable vehicles such as saline, Ringer's solution, dextrose solution, and the like.

Empirical considerations, such as the biological half-life, generally will contribute to the determination of the dosage. Frequency of administration may be determined and adjusted over the course of therapy, and is based on reducing the number of virally infected cells, maintaining the reduction of infected cells, reducing the proliferation of infected cells, or delaying the development of infection. Alternatively, sustained continuous release formulations of the bispecific molecules may be appropriate. Various formulations and devices for achieving sustained release are known in the art.

In one embodiment, dosages for the bispecific molecules may be determined empirically in individuals who have been given one or more administration(s). Individuals are given incremental dosages of the bispecific molecule. To assess efficacy of the bispecific molecules, a marker of the specific viral disease state can be followed. These include direct measurements of viral load, indirect measurement of viral load by immunoassay, other imaging techniques; an improvement in health as assessed by such measurements, the measurement of an indirect viral marker, e.g., a decrease in pain or paralysis; improved speech, vision, breathing or other disability associated with the infection; increased appetite; or an increase in quality of life as measured by accepted tests or prolongation of survival. It will be apparent to one of skill in the art that the dosage will vary depending on the individual, the type of virus, the stage of the disease, and the past and concurrent treatments being used.

Other formulations include suitable delivery forms known in the art including, but not limited to, carriers such as liposomes. See, for example, Mahato et al. (1997) "*Cationic Lipid-Based Gene Delivery Systems: Pharmaceutical Perspectives,*" Pharm. Res. 14:853-859. Liposomal preparations include, but are not limited to, cytofectins, multilamellar vesicles and unilamellar vesicles.

Having now generally described the invention, the same will be more readily understood through reference to the following Examples which relate to bispecific molecules that bind epitopes of the Epstein Barr virus or human papillomavirus. Such Examples are provided by way of illustration and are not intended to be limiting of the present invention unless specified.

Example 1

Construction of Bispecific Molecules for Latent EBV

Bispecific molecules specific for human T-cells and Epstein-Barr virus (CD3×LMP-1 and TCR×LMP-2) can be prepared as a dual affinity retargeting (diabody molecule. Such bispecific molecules have the ability to localize a T-cell (by binding such T-cell to the CD3 portion of a CD3-binding bispecific molecule or to the TCR portion of a TCR-binding bispecific molecule) to the location of a cell latently infected with EBV and expressing LMP-1 or LMP-2 (respectively) (by binding such cell to the LMP-1 or LMP-2 binding portion of the bispecific molecules). The localized T-cell can then mediate the killing of the cell latently infected with EBV in a process termed "redirected" killing. Antibodies that bind to LMP-1 or LMP-2 are known in the art (Fang, C. Y. et al. (2004) "*Construction And Characterization Of Monoclonal Antibodies Specific To Epstein-Barr Virus Latent Membrane Protein 1,*" J. Immunol. Methods 287(1-2):21-30; Fruehling, S. et al. (1996) "*Identification Of Latent Membrane Protein 2A (LMP2A) Domains Essential For The LMP2A Dominant-Negative Effect On B-Lymphocyte Surface Immunoglobulin Signal Transduction,*" J Virol. 70:6216-6226; Fruehling, S. et al. (1998) "*Tyrosine 112 Of Latent Membrane Protein 2A Is Essential For Protein Tyrosine Kinase Loading And Regulation Of Epstein-Barr Virus Latency,*" J. Virol. 72:7796-7806) and can be obtained from Acris Antibodies (San Diego, Calif.), GenWay (San Diego, Calif.), and other sources.

The CD3×LMP-1 bispecific molecule can be constructed having the anti-CD3 variable domain of anti-CD3 Antibody 2 and the anti-LMP-1 variable domains of antibody HHV-4 (Acris Antibodies). The TCR×LMP-2 bispecific molecule can be constructed having the anti-TCR variable domain of BMA031 and the anti-LMP-2 variable domains of antibody 14B7 (mybiosource(dot)com).

Binding of the bispecific molecule to LMP-1-expressing cells and to CD3-positive T-cells can be measured by ELISA. In order to demonstrate the ability of the bispecific molecule to mediate redirected killing of EBV infected cells, the above described CD3×LMP-1 bispecific molecule or the CD2×LMP-2 bispecific molecule can be incubated at various concentrations with target cells and effector cells (human PBMCs), for example at an effector to target ratio of 20:1. Cytotoxicity can be determined using, for example an LDH assay. The results will demonstrate the ability of the CD3×LMP-1 bispecific molecule and the CD3×LMP-2 bispecific molecule to mediate redirected killing of EBV infected cells with human PBMCs.

Example 2

Treating EBV Latent Infection

Resting memory B cells represent the site of persistence of EBV within the body. (Babcock, G. J. et al. "*Epstein-Barr Virus-Infected Resting Memory B Cells, Not Proliferating Lymphoblasts, Accumulate In The Peripheral Blood Of Immunosuppressed Patients,*" J. Exp. Med. 190(4):567-576) In normal EBV-infected adults, from 1 to 50 B cells per million in the circulation are infected with EBV, and the number of latently infected cells within a person remains stable over years.

Of the nearly 100 viral genes that are expressed during replication, only 10 are expressed in latently infected B cells in vitro, including LMP-1 and LMP-2.

By markedly limiting viral gene expression during latency, EBV reduces the number of viral proteins expressed, thereby limiting the "exposure" of infected cells to the host's cytotoxic T cells.

A patient with latent EBV infection is administers a CD3×LMP-1 bispecific molecule. The bispecific molecule binds to LMP-1 found on the surface of infected cells, recruits T-cells to the infected cells and activates the T-cells. The activated T-cells kill the EBV-infected cells thereby eliminating EBV infection in the patient.

Example 3

Construction of Bispecific Molecules for HPV

A bispecific molecule specific for human T-cells and human papillomavirus E6 (CD3×HPV E6/MHC) can be prepared as a dual affinity retargeting (diabody) molecule. Antibodies that bind to human papillomavirus E6 are known in the art (Phaeton, R. et al. (2010) "*Radioimmunotherapy With An Antibody To The HPV16 E6 Oncoprotein Is Effective In An Experimental Cervical Tumor Expressing Low Levels Of E6,*" Cancer Biol. Ther. 10(10):1041-1047; Lagrange, M. et al. (2005) "*Binding Of Human Papillomavirus 16 E6 To P53 And E6AP Is Impaired By Monoclonal Antibodies Directed Against The Second Zinc-Binding Domain Of E6,*" J. Gen. Virol. 86(Pt 4):1001-1007; Wlazlo, A. P. et al. (2001) "*Generation And Characterization Of Monoclonal Antibodies Against The E6 And E7 Oncoproteins Of HPV,*" Hybridoma 20(4):257-263) and can be obtained from Acris Antibodies (San Diego, Calif.), GenWay (San Diego, Calif.), mybiosource(dot)com and other sources.

Such a bispecific molecule has the ability to localize a T-cell (by binding such T-cell to the CD3 portion of a CD3-binding bispecific molecule) to the location of a cell infected with HPV, expressing E6 and displaying a fragment of the E6 protein in the context of the cell's MHC class I system (by binding such cell to the HPV E6/MHC binding portion of the bispecific molecules). The localized T-cell can then mediate the killing of the cell latently infected with EBV in a process termed "redirected" killing.

The CD3×HPV E6/MHC bispecific molecule can be constructed having, for example, the anti-CD3 variable domain of OKT3 and the anti-HPV E6/MHC variable domains of antibody 29-10267 (mybiosource(dot)com).

Binding of the bispecific molecule to HPV E6/MHC and to CD3-positive T-cells can be measured by ELISA. In order to demonstrate the ability of the bispecific molecule to mediate redirected killing of HPV infected cells, the above described CD3×HPV E6/MHC bispecific molecule can be incubated at various concentrations with target cells and effector cells (human PBMCs) for example at an effector to target ratio of 20:1. Cytotoxicity can be determined by LDH assay. The results will demonstrate the ability of the CD3× HPV E6/MHC bispecific molecule to mediate redirected killing of HPV infected cells with human PBMCs.

Example 4

Bispecific Molecules Comprising an Fc Region Mediate Potent Redirected T-Cell Killing A bispecific molecule can be constructed having an anti-CD3 variable domain and a domain that binds to a viral antigen and that further comprises an Fc region. Such molecule can be constructed by expressing three polypeptide chains in the same cell. The first polypeptide chain will comprise, for example, the light chain variable domain of an anti-CD3 antibody, a short linker, the variable heavy chain domain for an antibody that binds a viral antigen (e.g., HPV E6/MHC), and an E coil domain. The second polypeptide chain will comprise, for example, the light chain variable domain of the anti-HPV E6/MHC antibody, a short linker, the variable heavy chain domain for the anti-CD3 antibody, a K coil domain and last a CH2 and CH3 domain of an IgG Fc. The third polypeptide chain will comprise, for example, a CH2 and CH3 domain of the IgG Fc.

The E and K coils ensure that chain 1 heterodimerizes with chain 2. To ensure that chain 2 does not homodimerize at the CH2 and CH3 domains, the sequence is modified to include a knob at position 366 (T366W modification) (see U.S. Pat. Nos. 5,731,168; 5,807,706; 5,821,333; 7,429,652; 7,642,228; 7,695,936; and 8,216,80). To disable the Fc region, alanine residues are incorporated at positions 234 and 235 (see U.S. Pat. No. 5,624,821). To accept the knob created in the Fc region of chain 2, three substitutions are made in chain 3 to create a hole (T366S, L368A and Y407V). A modification at position 435 (H435R) is used to prevent homodimers of chain 3 from binding to Protein A, thus aiding in purification of the bispecific molecule. Any chain 3 homodimers can be purified away from the products by size exclusion chromatography.

Vectors encoding the three chains are transfected into CHO cells. Following appropriate selection, the cells are cultured in medium for 7 days. Culture medium and cells are harvested. The bispecific molecule is purified using chromatography methods well known in the art, and is shown to be capable of simultaneously binding to both CD3 expressed on the surface of immune effector cells and to HPV E6/MHC expressed on the surface of an HPV-infected cell, and thereby facilitating the death of such HPV-infected cell.

Example 5

Construction of an Anti-CD16×Anti-HIV env Bispecific Molecule

Construction of an Anti-Fluorescein×Anti-HIV env Bispecific Molecule

As a further example of the bispecific molecules of the present invention, a bispecific diabody molecule was produced that was composed of two polypeptide chains, covalently bonded to one another, so as to form a first epitope binding site specific for CD16 and a second epitope binding site specific for the HIV env protein.

The first polypeptide chain of the bispecific diabody preferably has:
(I) the light chain variable domain of anti-HIV env antibody 7B2 (GenBank Accession No. AFQ31503; Buchacher, A. et al. (1994) "*Generation Of Human Monoclonal Antibodies Against HIV-1 Proteins; Electrofusion And Epstein-Barr Virus Transformation For Peripheral Blood Lymphocyte Immortalization*," AIDS Res. Hum. Retroviruses 10(4):359-369; Shen, R. (2010) "*GP41-Specific Antibody Blocks Cell-Free HIV Type 1 Transcytosis Through Human Rectal Mucosa And Model Colonic Epithelium*," J. Immunol. 184(7):3648-3655) or an antibody that competes with antibody 7B2 for binding, or an antibody that binds to the env protein of HIV;
(II) the heavy chain variable domain of antibody h3G8 (WO 2012/162068; U.S. Pat. No. 7,351,803) or an antibody that competes with antibody 3G8 for binding, or an antibody that binds to CD16 (FcγRIIIA); and
(III) an E coil domain (i.e., (EVAALEK)$_4$; EVAALEKEV-AALEKEVAALEKEVAALEK; SEQ ID NO:39) or a K coil domain (i.e., (KVAALKE)$_4$; KVAALKEK-VAALKEKVAALKEKVAALKE; SEQ ID NO:40).

The second polypeptide chain of such bispecific diabody preferably has:
(I) the light chain variable domain of antibody h3G8 (WO 2012/162068; U.S. Pat. No. 7,351,803) or such antibody that competes with antibody 3G8 for binding, or such antibody that binds to CD16 (FcγRIIIA);
(II) the heavy chain variable domain of such antibody 7B2 or such antibody that competes with antibody 7B2 for binding, or such antibody that binds to the env protein of HIV; and
(III) a K coil domain (i.e., (KVAALKE)$_4$; KVAALKEK-VAALKEKVAALKEKVAALKE; SEQ ID NO:40) or an E coil domain (i.e., (EVAALEK)$_4$; EVAALEKEV-AALEKEVAALEKEVAALEK; SEQ ID NO:39).

In a preferred embodiment, a negatively charged, "E-coil" will be appended to one of the polypeptides being used to form the bispecific diabody and a positively charged "K-coil" will be appended to the second of the diabody's polypeptides.

Preferably, the first polypeptide chain of such a diabody has the amino acid sequence (SEQ ID NO:42) (CDRs are underlined):

```
DIVMTQSPDS LAVSPGERAT IHCKSSQTLL YSSNNRHSIA

WYQQRPGQPP KLLLYWASMR LSGVPDRFSG SGSGTDFTLT
```

```
INNLQAEDVA IYYCHQYSSH PPTFGHGTRV EIKGGGSGGG

GQVTLRESGP ALVKPTQTLT LTCTFSGFSL STSGMGVGWI

RQPPGKALEW LAHIWWDDDK RYNPALKSRL TISKDTSKNQ

VVLTMTNMDP VDTATYYCAQ INPAWFAYWG QGTLVTVSSG

GCGGGEVAAL EKEVAALEKE VAALEKEVAAL EK
``` wherein residues 1-113 are the light chain variable domain of antibody 7B2 (GenBank Accession No. AFQ31503) (CDR residues are shown in underline), residues 114-121 are the linker GGGSGGGG (SEQ ID NO:27), residues 122-239 are the heavy chain variable domain of antibody h3G8 (CDR residues are shown in underline), residues 240-245 are the linker GGCGGG (SEQ ID NO:38) and residues 246-277 are the E coil (EVAALEK)₄ [i.e. (SEQ ID NO:39) EVAALEKEVAALEKEVAALEKEVAALEK].

Preferably, the second polypeptide chain of such a diabody has the amino acid sequence (SEQ ID NO:43) (CDRs are underlined):

```
DIVMTQSPDS LAVSLGERAT INCKASQSVD FDGDSFMNWY

QQKPGQPPKL LIYTTSNLES GVPDRFSGSG SGTDFTLTIS

SLQAEDVAVY YCQQSNEDPY TFGQGTKLEI KGGGSGGGGQ

VQLVQSGGGV FKPGGSLRLS CEASGFTFTE YYMTWVRQAP

GKGLEWLAYI SKNGEYSKYS PSSNGRFTIS RDNAKNSVFL

QLDRLSADDT AVYYCARADG LTYFSELLQY IFDLWGQGAR

VTVSSGGCGG GKVAALKEKV AALKEKVAAL KEKVAALKE
``` wherein residues 1-111 are the light chain variable domain of antibody h3G8 (CDR residues are shown in underline), residues 112-119 are the linker GGGSGGGG (SEQ ID NO:27), residues 120-245 are the heavy chain variable domain of antibody 7B2 (GenBank Accession No. AFQ31502) (CDR residues are shown in underline), residues 246-251 are the linker GGCGGG (SEQ ID NO:38) and residues 252-279 are the K coil (KVAALKE)₄ [i.e., SEQ ID NO:40) KVAALKEKVAALKEKVAALKEKVAALKE].

A bispecific diabody was also produced that contained the variable light and heavy domains of the above-described anti-CD16 (FcγRIIIA) antibody h3G8 and the variable light and heavy domains of anti-fluorescein antibody 4-4-20 (Gruber, M. et al. (1994) "*Efficient Tumor Cell Lysis Mediated By A Bispecific Single Chain Antibody Expressed In Escherichia coli*," J. Immunol. 152(11):5368-5374; Bedzyk, W. D. et al. (1989) "*Comparison Of Variable Region Primary Structures Within An Anti-Fluorescein Idiotype Family*," J. Biol. Chem. 264(3): 1565-1569). The amino acid sequences of the two polypeptide chains of the control antibody are:

SEQ ID NO:44 (first polypeptide chain of control diabody; VL h3G8 VH 4-4-20) (CDRs are underlined):

```
DIVMTQSPDS LAVSLGERAT INCKASQSVD FDGDSFMNWY

QQKPGQPPKL LIYTTSNLES GVPDRFSGSG SGTDFTLTIS

SLQAEDVAVY YCQQSNEDPY TFGQGTKLEI KGGGSGGGGE

VKLDETGGGL VQPGRPMKLS CVASGFTFSD YWMNWVRQSP
```

```
EKGLEWVAQI RNKPYNYETY YSDSVKGRFT ISRDDSKSSV

YLQMNNLRVE DMGIYYCTGS YYGMDYWGQG TSVTVSSGGC

GGGEVAALEK EVAALEKEVA ALEKEVAALE KGGGNS
``` wherein residues 1-111 are the light chain variable domain of antibody h3G8, residues 112-119 are the linker GGGSGGGG (SEQ ID NO:27), residues 120-237 are the heavy chain variable domain of antibody 4-4-20, residues 238-243 are the linker GGCGGG (SEQ ID NO:38), residues 244-271 are the E coil (EVAALEK)₄ [i.e. (SEQ ID NO:39) EVAALEKEVAALEKEVAALEKEVAALEK], and residues 272-276 are the linker GGGNS (SEQ ID NO:41); and SEQ ID NO:45 (second polypeptide chain of control diabody; VL 4-4-20 VH h3G8) (CDRs are underlined):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IKGGGSGGGG

QVTLRESGPA LVKPTQTLTL TCTFSGFSLS TSGMGVGWIR

QPPGKALEWL AHIWWDDDKR YNPALKSRLT ISKDTSKNQV

VLTMTNMDPV DTATYYCAQI NPAWFAYWGQ GTLVTVSSGG

CGGGKVAALK EKVAALKEKV AALKEKVAAL KEGGGNSGGG

DYKDDDDKGG GSNS
``` wherein residues 1-112 are the light chain variable domain of antibody 4-4-20, residues 113-120 are the linker GGGSGGGG (SEQ ID NO:27), residues 121-238 are the heavy chain variable domain of antibody h3G8, residues 239-244 are the linker GGCGGG (SEQ ID NO:38), residues 245-272 are the K coil (KVAALKE)₄ [i.e., SEQ ID NO:40) KVAALKEKVAALKEKVAALKEKVAALKE], residues 273-277 are the linker GGGNS (SEQ ID NO:41) and residues 278-294 are a FLAG-tag (Munro, S. et al. (1984) "*Use Of Peptide Tagging To Detect Proteins Expressed From Cloned Genes: Deletion Mapping Functional Domains Of Drosophila hsp 70*," EMBO J. 3(13):3087-3093).

Example 6

Cytotoxic Lymphocyte Activity Assessment of CD16×HIV env Bispecific Molecules

The initial step in HIV-1 infection occurs with the binding of cell surface CD4 to trimeric HIV-1 envelope glycoproteins (Env), a heterodimer of a transmembrane glycoprotein (gp41) and a surface glycoprotein (gp120). The conformational changes triggered in trimeric Env upon CD4 binding lead ultimately to fusion of the viral and cell membranes and to delivery of the viral core into infected cells (Harris, A. et al. (2011) "*Trimeric HIV-1 Glycoprotein Gp140 Immunogens And Native HIV-1 Envelope Glycoproteins Display The Same Closed And Open Quaternary Molecular Architectures*," Proc. Natl. Acad. Sci. (U.S.A.) 108(28):11440-11445). The gp120 and gp41 glycoproteins are initially synthesized as a single gp160 polypeptide that is subsequently cleaved to generate the non-covalently associated gp120/gp41 complex. The ectodomain of Env is a heterodimer with mass of approximately 140 kDa, composed of the entire gp120 component, and approximately 20 kDa of gp41

(Harris, A. et al. (2011) "*Trimeric HIV-*1 *Glycoprotein Gp*140 *Immunogens And Native HIV-*1 *Envelope Glycoproteins Display The Same Closed And Open Quaternary Molecular Architectures*," Proc. Natl. Acad. Sci. (U.S.A.) 108(28): 11440-11445).

Human embryonic kidney HEK 293 D375 cells (92Th023, subtype AE, R5-tropic) express the HIV gp140 protein. As a further example of the utility of the bispecific molecules of the present invention, the above-described anti-CD16×anti-HIV env bispecific diabody was evaluated for its ability to mediate cytotoxic lymphocyte activity of HEK 293 D375 cells in the presence of natural killer cells. The above-described anti-fluorescein×anti-HIV env bispecific diabody was used as a control.

Figure 2:
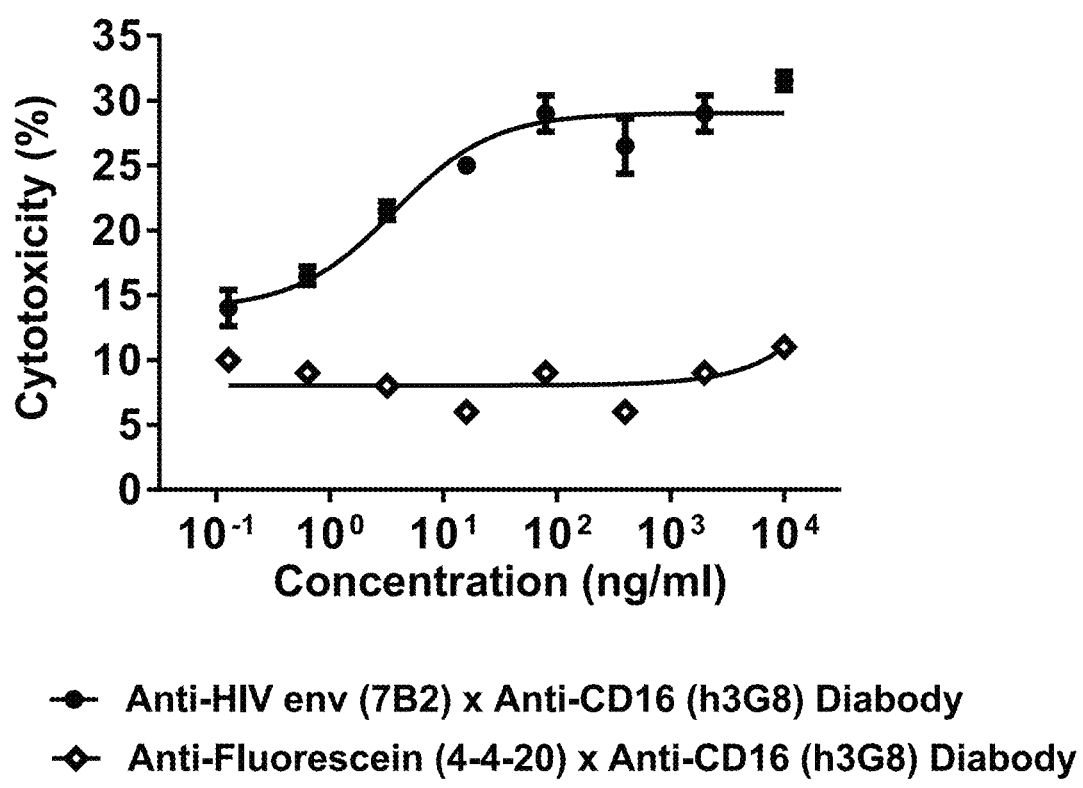
FIG. 2 shows cytotoxic lymphocyte activity mediated by a bispecific diabody comprising the anti-CD16 epitope binding domains of antibody h3G8 and the anti-HIV env epitope binding domains of antibody 7B2 on gp140-expressing HEK 293 D375 cells (92Th023, subtype AE, R5-tropic) after 24 hours of incubation in the presence of natural killer (NK) at an Effector:Target ratio of 5:1. The natural killer (NK) cells were purified by positive selection (D56678 (LDH)). A bispecific diabody comprising the anti-fluorescein epitope binding domains of antibody 4-4-20 and the anti-HIV env epitope binding domains of antibody 7B2 was used as a control.

The results of this investigation are shown in FIG. 2. FIG. 2 shows cytotoxic lymphocyte activity mediated by a bispecific diabody comprising the anti-CD16 epitope binding domains of antibody h3G8 and the anti-HIV env epitope binding domains of antibody 7B2 on gp140-expressing HEK 293 D375 cells (92Th023, subtype AE, R5-tropic) after 24 hours of incubation in the presence of natural killer (NK) at an Effector:Target ratio of 5:1. The natural killer (NK) cells were purified by positive selection (D56678 (LDH)). A bispecific diabody comprising the anti-fluorescein epitope binding domains of antibody 4-4-20 and the anti-HIV env epitope binding domains of antibody 7B2 was used as a control. The results show that the anti-CD16×anti-HIV env bispecific diabody mediated cytotoxic lymphocyte activity, whereas the control diabody did not.

Figure 3:
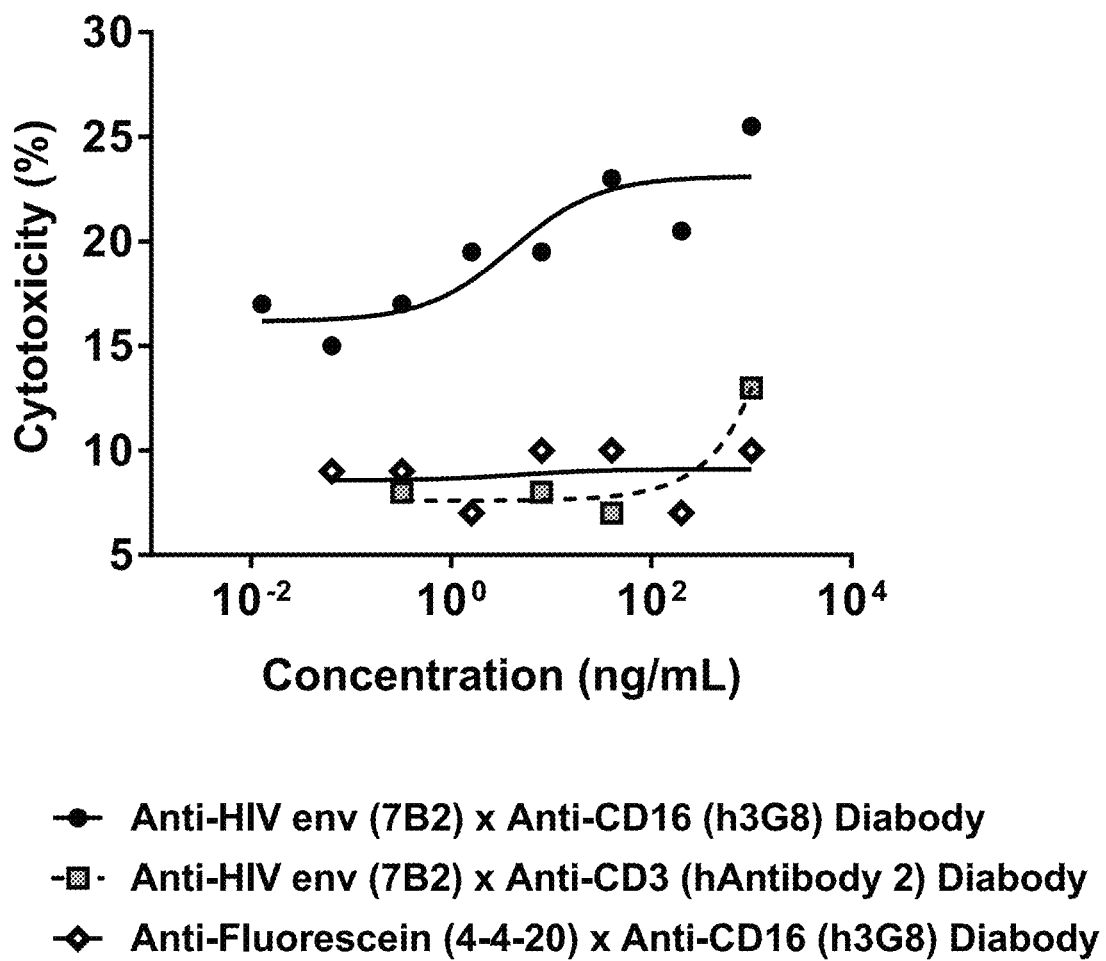
FIG. 3 shows cytotoxic lymphocyte activity mediated by a bispecific diabody comprising the anti-CD16 epitope binding domains of antibody h3G8 and the anti-HIV env epitope binding domains of antibody 7B2 on gp140-expressing HEK 293 D375 cells (92Th023, subtype AE, R5-tropic) after 24 hours of incubation in the presence of natural killer (NK) at an Effector:Target ratio of 5:1. The natural killer (NK) cells were purified by negative selection (D55386 (LDH)). As expected (since NK cells lack CD3), a bispecific diabody comprising the anti-CD3 epitope binding domains of antibody hAntibody 2 and the anti-HIV env epitope binding domains of antibody 7B2 fail to show cytotoxic lymphocyte activity. A bispecific diabody comprising the anti-fluorescein epitope binding domains of antibody 4-4-20 and the anti-CD16 epitope binding domains of antibody h3G8 was used as a control.

FIG. 3 shows cytotoxic lymphocyte activity mediated by a bispecific diabody comprising the anti-CD16 epitope binding domains of antibody h3G8 and the anti-HIV env epitope binding domains of antibody 7B2 on gp140-expressing HEK 293 D375 cells (92Th023, subtype AE, R5-tropic) after 24 hours of incubation in the presence of natural killer (NK) at an Effector:Target ratio of 5:1. The natural killer (NK) cells were purified by negative selection (D55386 (LDH)). As expected (since NK cells lack CD3), a bispecific diabody comprising the anti-CD3 epitope binding domains of antibody hAntibody 2 and the anti-HIV env epitope binding domains of antibody 7B2 fail to show cytotoxic lymphocyte activity. A bispecific diabody comprising the anti-fluorescein epitope binding domains of antibody 4-4-20 and the anti-CD16 epitope binding domains of antibody h3G8 was used as a control. The results again show that the anti-CD16×anti-HIV env bispecific diabody mediated cytotoxic lymphocyte activity, whereas the above-described control diabody, and the CD16×CD3 bispecific diabody did not.

Figure 4:
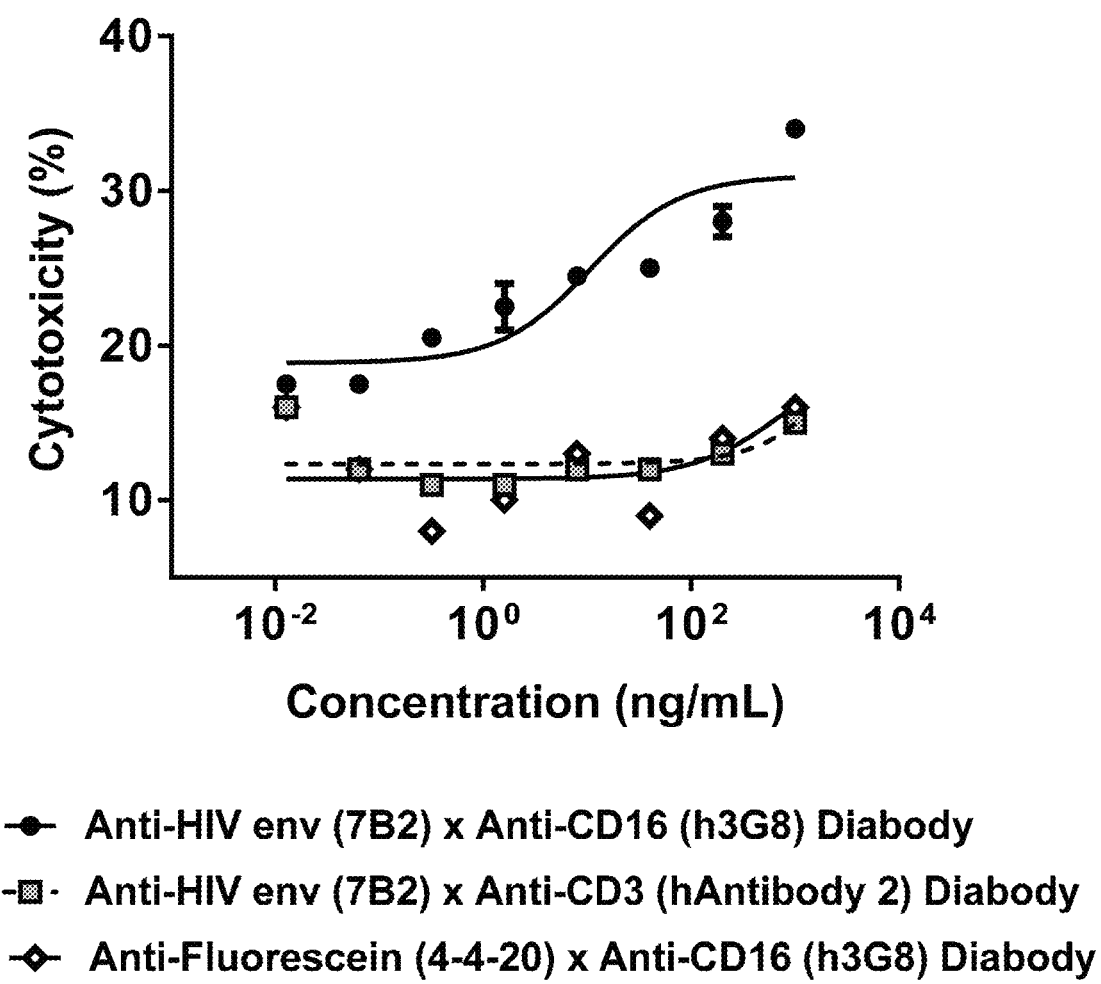
FIG. 4 shows cytotoxic lymphocyte activity mediated by a bispecific diabody comprising the anti-CD16 epitope binding domains of antibody h3G8 and the anti-HIV env epitope binding domains of antibody 7B2 on HIV gp140-expressing HEK 293 D371 cells (CM244, subtype AE, R5-tropic) after 24 hours of incubation in the presence of natural killer (NK) at an Effector:Target ratio of 5:1. The natural killer (NK) cells were purified by negative selection (D55386 (LDH)). As expected (since NK cells lack CD3), a bispecific diabody comprising the anti-CD3 epitope binding domains of antibody hAntibody 2 and the anti-HIV env epitope binding domains of antibody 7B2 fail to show cytotoxic lymphocyte activity. A bispecific diabody comprising the anti-fluorescein epitope binding domains of antibody 4-4-20 and the anti-CD16 epitope binding domains of antibody h3G8 was used as a control.

FIG. 4 shows the results of a similar experiment conducted using HEK 293 D371 (CM244, subtype AE, R5-tropic) cells, which express HIV gp140. FIG. 4 shows cytotoxic lymphocyte activity mediated by a bispecific diabody comprising the anti-CD16 epitope binding domains of antibody h3G8 and the anti-HIV env epitope binding domains of antibody 7B2 on HIV gp140-expressing HEK 293 D371 cells (CM244, subtype AE, R5-tropic) after 24 hours of incubation in the presence of natural killer (NK) at an Effector:Target ratio of 5:1. The natural killer (NK) cells were purified by negative selection (D55386 (LDH)). As expected (since NK cells lack CD3), a bispecific diabody comprising the anti-CD3 epitope binding domains of antibody hAntibody 2 and the anti-HIV env epitope binding domains of antibody 7B2 fail to show cytotoxic lymphocyte activity. A bispecific diabody comprising the anti-fluorescein epitope binding domains of antibody 4-4-20 and the anti-CD16 epitope binding domains of antibody h3G8 was used as a control. The results again show that the anti-CD16× anti-HIV env bispecific diabody mediated cytotoxic lymphocyte activity, whereas the above-described control diabodies did not.

Example 7

Construction of an Anti-CD3×Anti-HIV gp120 Bispecific Molecule

Construction of an Anti-CD3×Anti-HIV env Bispecific Molecule

Construction of an Anti-CD3×Anti-RSV F Protein Bispecific Molecule

Construction of an Anti-Fluorescein×Anti-HIV env Bispecific Molecule

As further examples of the bispecific molecules of the present invention, bispecific diabody molecules were produced that were composed of two polypeptide chains, covalently bonded to one another, so as to form a first epitope binding site specific for CD3 and a second epitope binding site specific for either the HIV gp120 protein, the HIV env protein, or the A antigenic site of the RSV F protein.

Anti-CD3×Anti-HIV gp120 Bispecific Molecule

The first polypeptide chain of the bispecific diabody preferably has:

(I) the light chain variable domain of anti-HIV gp120 antibody A32 (Ferrari, G. et al. (2011) "*An HIV-*1 *gp*120 *Envelope Human Monoclonal Antibody That Recognizes a C*1 *Conformational Epitope Mediates Potent Antibody-Dependent Cellular Cytotoxicity* (*ADCC*) *Activity and Defines a Common ADCC Epitope in Human HIV-*1 *Serum*," J. Virol. 85(14):7029-7036) or an antibody that competes with antibody A32 for binding, or an antibody that binds to the gp120 protein of HIV;

(II) the heavy chain variable domain of humanized anti-CD3 Antibody 2 ("hAntibody 2") or an antibody that competes with anti-CD3 antibody 2 for binding, or an antibody that binds to CD3; and (III) an E coil domain (i.e., (EVAALEK)$_4$; EVAALEKEV-AALEKEVAALEKEVAALEK; SEQ ID NO:39) or a K coil domain (i.e., (KVAALKE)$_4$; KVAALKEK-VAALKEKVAALKEKVAALKE; SEQ ID NO:40).

The second polypeptide chain of such bispecific diabody preferably has:

(I) the light chain variable domain of humanized anti-CD3 Antibody 2 ("hAntibody 2") or such antibody that competes with anti-CD3 antibody 2 for binding, or such antibody that binds to CD3;

(II) the heavy chain variable domain of such antibody A32 or such antibody that competes with antibody A32 for binding, or such antibody that binds to the gp120 protein of HIV; and (III) a K coil domain (i.e., (KVAALKE)$_4$; KVAALKEK-VAALKEKVAALKEKVAALKE; SEQ ID NO:40) or an E coil domain (i.e., (EVAALEK)$_4$; EVAALEKEV-AALEKEVAALEKEVAALEK; SEQ ID NO:39).

In a preferred embodiment, a negatively charged, "E-coil" will be appended to one of the polypeptides being used to form the bispecific diabody and a positively charged "K-coil" will be appended to the second of the diabody's polypeptides.

Preferably, the first polypeptide chain of such a diabody has the amino acid sequence (SEQ ID NO:46) (CDRs are underlined):

```
QSALTQPPSA SGSPGQSVTI SCTGTSSDVG GYNYVSWYQH

HPGKAPKLII SEVNNRPSGV PDRFSGSKSG NTASLTVSGL

QAEDEAEYYC SSYTDIHNFV FGGGTKLTVL GGGSGGGGEV

QLVESGGGLV QPGGSLRLSC AASGFTFSTY AMNWVRQAPG

KGLEWVGRIR SKYNNYATYY ADSVKGRFTI SRDDSKNSLY

LQMNSLKTED TAVYYCVRHG NFGNSYVSWF AYWGQGTLVT

VSSGGCGGGE VAALEKEVAA LEKEVAALEK EVAALEK
``` wherein residues 1-110 are the light chain variable domain of antibody A32 (CDR residues are shown in underline), residues 111-118 are the linker GGGSGGGG (SEQ ID NO:27), residues 119-243 are the heavy chain variable domain of humanized anti-CD3 Antibody 2 ("hAntibody 2; CDRs are shown underlined), residues 247-252 are the linker GGCGGG (SEQ ID NO:38) and residues 253-280 are the E coil (EVAALEK)$_4$ [i.e. (SEQ ID NO:39) EVAALEKEVAALEKEVAALEKEVAALEK].

Preferably, the second polypeptide chain of such a diabody has the amino acid sequence (SEQ ID NO:47) (CDRs are underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLQESGPGLV KPSQTLSLSC TVSGGSSSSG AHYWSWIRQY

PGKGLEWIGY IHYSGNTYYN PSLKSRITIS QHTSENQFSL

KLNSVTVADT AVYYCARGTR LRTLRNAFDI WGQGTLVTVS

SGGCGGGKVA ALKEKVAALK EKVAALKEKV AALKE
``` wherein residues 1-110 are the light chain variable domain of anti-CD3 Antibody 2 (CDR residues are shown in underline), residues 111-118 are the linker GGGSGGGG (SEQ ID NO:27), residues 119-241 are the heavy chain variable domain of antibody A32 (CDR residues are shown in underline), residues 242-247 are the linker GGCGGG (SEQ ID NO:38) and residues 248-275 are the K coil (KVAALKE)$_4$ [i.e., SEQ ID NO:40) KVAALKEKVAALKEKVAALKEKVAALKE].

Anti-CD3×Anti-HIV env Bispecific Molecule

The first polypeptide chain of the bispecific diabody preferably has:
(I) the light chain variable domain of antibody 7B2 (GenBank Accession No. AFQ31503; Buchacher, A. et al. (1994) "*Generation Of Human Monoclonal Antibodies Against HIV-1 Proteins; Electrofusion And Epstein-Barr Virus Transformation For Peripheral Blood Lymphocyte Immortalization*," AIDS Res. Hum. Retroviruses 10(4): 359-369; Shen, R. (2010) "*GP41-Specific Antibody Blocks Cell-Free HIV Type 1 Transcytosis Through Human Rectal Mucosa And Model Colonic Epithelium*," J. Immunol. 184(7):3648-3655) or an antibody that competes with antibody 7B2 for binding, or an antibody that binds to the env protein of HIV; and
(II) the heavy chain variable domain of humanized anti-CD3 Antibody 2 ("hAntibody 2") or an antibody that competes with anti-CD3 antibody 2 for binding, or an antibody that binds to CD3; and
(III) an E coil domain (i.e., (EVAALEK)$_4$; EVAALEKEVAALEKEVAALEKEVAALEK; SEQ ID NO:39) or a K coil domain (i.e., (KVAALKE)$_4$; KVAALKEKVAALKEKVAALKEKVAALKE; SEQ ID NO:40).

The second polypeptide chain of such bispecific diabody preferably has:
(I) the light chain variable domain of humanized anti-CD3 Antibody 2 ("hAntibody 2") or such antibody that competes with anti-CD3 antibody 2 for binding, or such antibody that binds to CD3;
(II) the heavy chain variable domain of such antibody 7B2 or such antibody that competes with antibody 7B2 for binding, or such antibody that binds to the env protein of HIV; and
(III) a K coil domain (i.e., (KVAALKE)$_4$; KVAALKEKVAALKEKVAALKEKVAALKE; SEQ ID NO:40) or an E coil domain (i.e., (EVAALEK)$_4$; EVAALEKEVAALEKEVAALEKEVAALEK; SEQ ID NO:39).

In a preferred embodiment, a negatively charged, "E-coil" will be appended to one of the polypeptides being used to form the bispecific diabody and a positively charged "K-coil" will be appended to the second of the diabody's polypeptides.

Preferably, the first polypeptide chain of such a diabody has the amino acid sequence (SEQ ID NO:48) (CDRs are underlined):

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIKGGGSGGG

GEVQLVESGG GLVQPGGSLR LSCAASGFTF STYAMNWVRQ

APGKGLEWVG RIRSKYNNYA TYYADSVKGR FTISRDDSKN

SLYLQMNSLK TEDTAVYYCV RHGNFGNSYV SWFAYWGQGT

LVTVSSGGCG GGEVAALEKE VAALEKEVAA LEKEVAALEK
``` wherein residues 1-113 are the light chain variable domain of antibody 7B2 (GenBank Accession No. AFQ31503) (CDR residues are shown in underline), residues 114-121 are the linker GGGSGGGG (SEQ ID NO:27), residues 122-246 are the heavy chain variable domain of humanized anti-CD3 Antibody 2 ("hAntibody 2;" CDRs are shown underlined), residues 247-252 are the linker GGCGGG (SEQ ID NO:38) and residues 253-280 are the E coil (EVAALEK)$_4$ [i.e. (SEQ ID NO:39) EVAALEKEVAALEKEVAALEKEVAALEK].

Preferably, the second polypeptide chain of such a diabody has the amino acid sequence (SEQ ID NO:49) (CDRs are underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLVQSGGGVF KPGGSLRLSC EASGFTFTEY YMTWVRQAPG

KGLEWLAYIS KNGEYSKYSP SSNGRFTISR DNAKNSVFLQ

LDRLSADDTA VYYCARADGL TYFSELLQYI FDLWGQGARV

TVSSGGCGGG KVAALKEKVA ALKEKVAALK EKVAALKE
``` wherein residues 1-110 are the light chain variable domain of antibody Anti-CD3 Antibody 2 (CDR residues are shown in underline), residues 111-118 are the linker GGGSGGGG (SEQ ID NO:27), residues 119-244 are the heavy chain variable domain of antibody 7B2 (GenBank Accession No. AFQ31502) (CDR residues are shown in underline), residues 245-250 are the linker GGCGGG (SEQ ID NO:38) and residues 251-278 are the K coil (KVAALKE)₄ [i.e., SEQ ID NO:40) KVAALKEKVAALKEKVAALKEKVAALKE].

Anti-CD3×Anti-RSV F Protein Bispecific Molecule

The first polypeptide chain of the bispecific diabody preferably has:
(I) the light chain variable domain of humanized anti-CD3 Antibody 2 ("hAntibody 2") or an antibody that competes with anti-CD3 antibody 2 for binding, or an antibody that binds to CD3; and
(II) the heavy chain variable domain of the anti-RSV F Protein antibody, Palivizumab (Beeler, J. A. et al. (1989) "*Neutralization Epitopes Of The F Glycoprotein Of Respiratory Syncytial Virus: Effect Of Mutation Upon Fusion Function,*" J. Virol. 63(7):2941-2950; Arbiza, J. et al. (1992) "*Characterization Of Two Antigenic Sites Recognized By Neutralizing Monoclonal Antibodies Directed Against The Fusion Glycoprotein Of Human Respiratory Syncytial Virus,*" J. Gen. Virol. 73(9):2225-2234; Shadman, K. A. et al. (2011) "*A Review Of Palivizumab And Emerging Therapies For Respiratory Syncytial Virus,*" Expert Opin. Biol. Ther. 11(11):1455-1467; Wang, D. et al. (2011) "*Palivizumab For Immunoprophylaxis Of Respiratory Syncytial Virus (RSV) Bronchiolitis In High-Risk Infants And Young Children: A Systematic Review And Additional Economic Modelling Of Subgroup Analyses,*" Health Technol. Assess. 15(5):iii-iv, 1-124. doi: 10.3310/hta15050) or an antibody that competes with Palivizumab for binding, or an antibody that binds to the A antigenic site of the RSV F protein;
(III) an E coil domain (i.e., (EVAALEK)₄; EVAALEKEV-AALEKEVAALEKEVAALEK; SEQ ID NO:39) or a K coil domain (i.e., (KVAALKE)₄; KVAALKEK-VAALKEKVAALKEKVAALKE; SEQ ID NO:40).

The second polypeptide chain of such bispecific diabody preferably has:
(I) the light chain variable domain of the anti-RSV F Protein antibody, Palivizumab, or such antibody that competes with Palivizumab for binding, or such antibody that binds to the A antigenic site of the RSV F protein; and
(II) the heavy chain variable domain of humanized anti-CD3 Antibody 2 ("hAntibody 2") or such antibody that competes with anti-CD3 antibody 2 for binding, or such antibody that binds to CD3;
(III) a K coil domain (e.g., (KVAALKE)₄; KVAALKEK-VAALKEKVAALKEKVAALKE; SEQ ID NO:40) or an E coil domain (i.e., (EVAALEK)₄; EVAALEKEV-AALEKEVAALEKEVAALEK; SEQ ID NO:39).

In a preferred embodiment, a negatively charged, "E-coil" will be appended to one of the polypeptides being used to form the bispecific diabody and a positively charged "K-coil" will be appended to the second of the diabody's polypeptides.

Preferably, the first polypeptide chain of such a diabody has the amino acid sequence (SEQ ID NO:50) (CDRs are underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV
```

-continued
```
TLRESGPALV KPTQTLTLTC TFSGFSLSTS GMSVGWIRQP

PGKALEWLAD IWNDDKEDYN PSLKSRLTIS KDTSKNQVVL

KVTNMDPADT ATYYCARSMI TNWYFDVWGA GTTVTVSSGG

CGGGEVAALE KEVAALEKEV AALEKEVAAL EK
``` wherein residues 1-110 are the light chain variable domain of anti-CD3 Antibody 2 (CDR residues are shown in underline), residues 111-118 are the linker GGGSGGGG (SEQ ID NO:27), residues 119-238 are the heavy chain variable domain of the anti-RSV F Protein antibody, Palivizumab (CDR residues are shown in underline), residues 239-244 are the linker GGCGGG (SEQ ID NO:38) and residues 245-272 are the E coil (EVAALEK)₄ [i.e. (SEQ ID NO:39) EVAALEKEVAALEKEVAALEKEVAALEK].

Preferably, the second polypeptide chain of such a diabody has the amino acid sequence (SEQ ID NO:51) (CDRs are underlined):

```
DIQMTQSPST LSASVGDRVT ITCRASQSVG YMHWYQQKPG

KAPKLLIYDT SKLASGVPSR FSGSGSGTEF TLTISSLQPD

DFATYYCFQG SGYPFTFGGG TKLEIKGGGS GGGGEVQLVE

SGGGLVQPGG SLRLSCAASG FTFSTYAMNW VRQAPGKGLE

WVGRIRSKYN NYATYYADSV KGRFTISRDD SKNSLYLQMN

SLKTEDTAVY YCVRHGNFGN SYVSWFAYWG QGTLVTVSSG

GCGGGKVAAL KEKVAALKEK VAALKEKVAA LKE
``` wherein residues 1-106 are the light chain variable domain of the anti-RSV F Protein antibody, Palivizumab (CDRs are shown underlined), residues 107-114 are the linker GGGSGGGG (SEQ ID NO:27), residues 115-239 are the heavy chain variable domain of humanized anti-CD3 Antibody 2 ("hAntibody 2;" CDRs are shown underlined), residues 240-245 are the linker GGCGGG (SEQ ID NO:38) and residues 246-273 are the K coil (KVAALKE)₄ [i.e., SEQ ID NO:40) KVAALKEKVAALKEKVAALKEKVAALKE].

Anti-Fluorescein×Anti-HIV env Bispecific Molecule

The first polypeptide chain of the bispecific diabody preferably has:
(I) the variable light domain of antibody 7B2 or an antibody that competes with antibody 7B2 for binding, or an antibody that binds to the env protein of HIV;
(II) the heavy chain variable domain of anti-fluorescein antibody 4-4-20 or an antibody that competes with anti-fluorescein antibody 4-4-20 for binding, or an antibody that binds to fluorescein; and
(III) an E coil domain (i.e., (EVAALEK)₄; EVAALEKEV-AALEKEVAALEKEVAALEK; SEQ ID NO:39) or a K coil domain (i.e., (KVAALKE)₄; KVAALKEK-VAALKEKVAALKEKVAALKE; SEQ ID NO:40).

The second polypeptide chain of such bispecific diabody preferably has:
(I) the light chain variable domain of anti-fluorescein antibody 4-4-20 or such antibody that competes with antibody 4-4-20 for binding, or such antibody that binds to fluorescein;
(II) the variable heavy domain of such antibody 7B2 or such antibody that competes with antibody 7B2 for binding, or such antibody that binds to the env protein of HIV; and (III) a K coil domain (i.e., (KVAALKE)₄; KVAALKEK-VAALKEKVAALKEKVAALKE; SEQ ID NO:40) or an E coil domain (i.e., (EVAALEK)₄; EVAALEKEV-AALEKEVAALEKEVAALEK; SEQ ID NO:39).

In a preferred embodiment, a negatively charged, "E-coil" will be appended to one of the polypeptides being used to form the bispecific diabody and a positively charged "K-coil" will be appended to the second of the diabody's polypeptides.

Preferably, the first polypeptide chain of such a diabody has the amino acid sequence (SEQ ID NO:52) (CDRs are underlined):

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIKGGGSGGG

GEVKLDETGG GLVQPGRPMK LSCVASGFTF SDYWMNWVRQ

SPEKGLEWVA QIRNKPYNYE TYYSDSVKGR FTISRDDSKS

SVYLQMNNLR VEDMGIYYCT GSYYGMDYWG QGTSVTVSSG

GCGGGEVAAL EKEVAALEKE VAALEKEVAA LEK
``` wherein residues 1-113 are the light chain variable domain of antibody 7B2 (GenBank Accession No. AFQ31503) (CDR residues are shown in underline), residues 114-121 are the linker GGGSGGGG (SEQ ID NO:27), residues 122-239 are the heavy chain variable domain of antibody 4-4-20, residues 240-245 are the linker GGCGGG (SEQ ID NO:38) and residues 246-277 are the E coil (EVAALEK)₄ [i.e. (SEQ ID NO:39) EVAALEKEVAALEKEV-AALEKEVAALEK].

Preferably, the second polypeptide chain of such a diabody has the amino acid sequence (SEQ ID NO:53) (CDRs are underlined):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IKGGGSGGGG

QVQLVQSGGG VFKPGGSLRL SCEASGFTFT EYYMTWVRQA

PGKGLEWLAY ISKNGEYSKY SPSSNGRFTI SRDNAKNSVF

LQLDRLSADD TAVYYCARAD GLTYFSELLQ YIFDLWGQGA

RVTVSSGGCG GGKVAALKEK VAALKEKVAA LKEKVAALKE
``` wherein residues 1-112 are the light chain variable domain of antibody 4-4-20, residues 113-120 are the linker GGGSGGGG (SEQ ID NO:27), residues 121-246 are the heavy chain variable domain of antibody 7B2 (CDR residues are shown in underline), residues 247-252 are the linker GGCGGG (SEQ ID NO:38) and residues 253-280 are the K coil (KVAALKE)₄ [i.e., SEQ ID NO:40) KVAALKEK-VAALKEKVAALKEKVAALKE].

Example 8

Redirected CD8-Mediated Killing of HIV env-Expressing Cells

As a further example of the utility of the bispecific molecules of the present invention, the above-described anti-CD3×anti-HIV gp120 and anti-CD3×anti-HIV env bispecific molecules were evaluated for their ability to facilitate redirected CD8-mediated killing of HIV env-expressing cells in the presence of T cells.

The above-described anti-fluorescein×anti-HIV env and anti-CD3×anti-RSV F protein bispecific molecules were used as controls.

Figure 5:
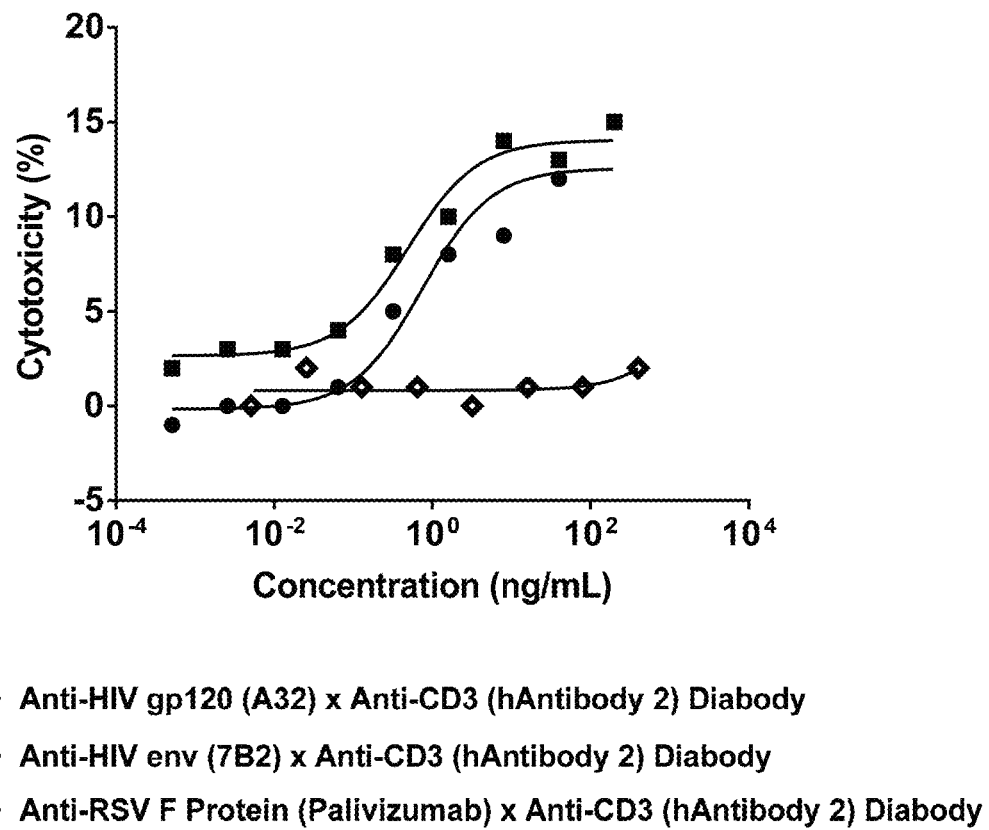
FIG. 5 shows the ability of bispecific diabodies comprising the anti-CD3 epitope binding domains of antibody hAntibody 2 and either the anti-HIV gp120 epitope binding domains of antibody A32 or the anti-HIV env epitope binding domains of antibody 7B2 to facilitate redirected CD8-mediated killing of HIV env-expressing Jurkat 522 FY cells in the presence of pan T cells (D54670). Cells were incubated for 24 hours. The Effector:Target ratio was 5:1. A bispecific diabody comprising the anti-RSV F Protein epitope binding domains of Palivizumab and the anti-CD3 epitope binding domains of antibody hAntibody 2 was used as a control.

In one such investigation, Jurkat 522 FY (HxB2 gp160) cells were incubated in the presence of tetracycline in order to induce their expression of HIV gp160. The cells were incubated for 24 hours in the presence of pan T cells (D54670) (at an Effector:Target ratio of 10:1) and one of the above-described bispecific molecules. The cytotoxicity of the bispecific molecule was assessed. The results show that the anti-CD3×anti-HIV gp120 and the anti-CD3×anti-HIV env bispecific molecules were both able to cause CD8-mediated cytotoxicity, whereas the anti-CD3×anti-RSV F protein control diabody did not (FIG. 5).

Figure 6:
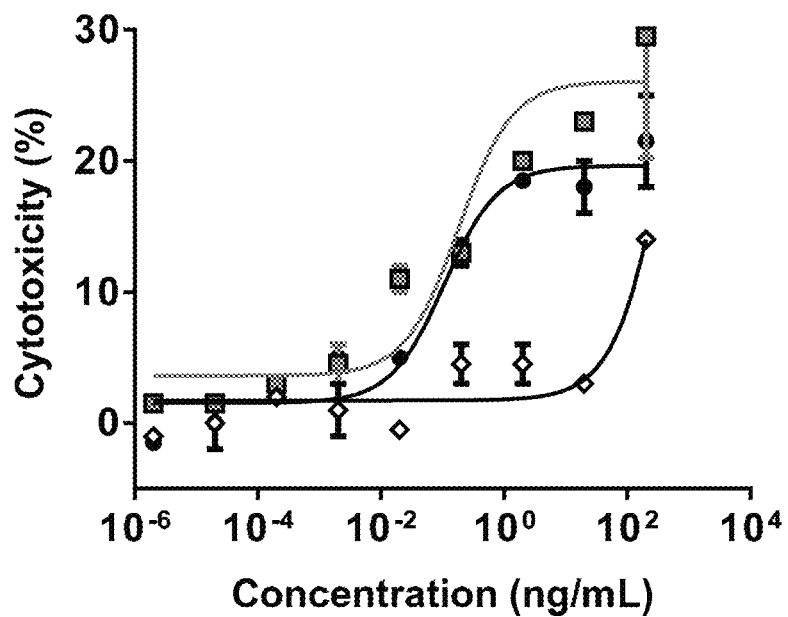
FIG. 6 shows the ability of bispecific diabodies comprising the anti-CD3 epitope binding domains of antibody hAntibody 2 and either the anti-HIV gp120 epitope binding domains of antibody A32 or the anti-HIV env epitope binding domains of antibody 7B2 to facilitate redirected CD8-mediated killing of HIV gp140-expressing HEK 293 D375 cells (92Th023 gp140) after 24 hours of incubation in the presence of pan T cells (D47239) at an Effector:Target ratio of 10:1. A bispecific diabody comprising the anti-HIV env epitope binding domains of antibody 7B2 and the anti-fluorescein epitope binding domains of antibody 4-4-20 was used as a control.

In a second investigation, HEK 293 D375 cells (92Th023, subtype AE, R5-tropic) were incubated in the presence of doxycycline in order to induce their expression of HIV gp140. The cells were incubated for 24 hours in the presence of pan T cells (D47239) (at an Effector:Target ratio of 10:1) and one of the above-described bispecific molecules. The cytotoxicity of the bispecific molecule was assessed. The results show that the anti-CD3×anti-HIV gp120 and the anti-CD3×anti-HIV env bispecific molecules were both able to cause CD8-mediated cytotoxicity, whereas the anti-HIV env×anti-fluorescein control diabody did not, except under antibody-saturating conditions (FIG. 6).

Figure 7:
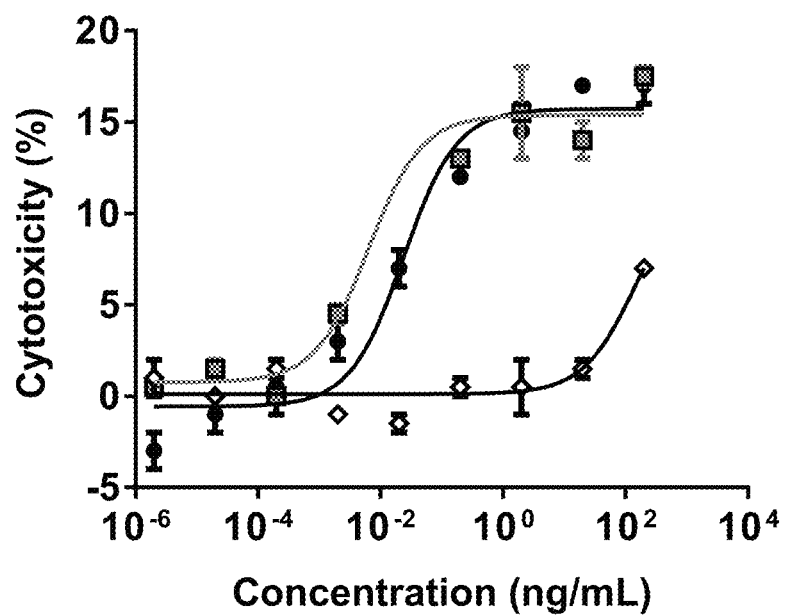
FIG. 7 shows the ability of bispecific diabodies comprising the anti-CD3 epitope binding domains of antibody hAntibody 2 and either the anti-HIV gp120 epitope binding domains of antibody A32 or the anti-HIV env epitope binding domains of antibody 7B2 to facilitate redirected CD8-mediated killing of HIV gp140-expressing HEK 293

In a third investigation, HEK 293 D371 cells (CM244, subtype AE, R5-tropic) were incubated in the presence of doxycycline in order to induce their expression of HIV gp140. The cells were incubated for 24 hours in the presence of pan T cells (D47239) (at an Effector:Target ratio of 10:1) and one of the above-described bispecific molecules. The cytotoxicity of the bispecific molecule was assessed. The results again showed that the anti-CD3×anti-HIV gp120 and the anti-CD3×anti-HIV env bispecific molecules were both able to cause CD8-mediated cytotoxicity, whereas the anti-HIV env×anti-fluorescein control diabody did not, except under antibody-saturating conditions (FIG. 7).

Table 1 summarizes the observed CD8-mediated cytotoxicity obtained using the anti-CD3×anti-HIV gp120 bispecific molecule or anti-CD3×anti-HIV env bispecific molecule.

TABLE 1

| | $EC_{50}$ (ng/mL) | |
| --- | --- | --- |
| Cell Line | 7B2 × CD3 | A32 × CD3 |
| Jurkat 522Fy | 0.49 | 0.75 |
| HEK 293 D371 | 0.006 | 0.024 |
| HEK 293 D375 | 0.18 | 0.11 |

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A bispecific diabody comprising first and second polypeptide chains, wherein:
   (A) the first polypeptide chain comprises, in the N-terminal to C-terminal direction:
   (i) a domain (A) comprising a binding region of a light chain variable domain of a first immunoglobulin (VL1) specific for an HIV epitope;
   (ii) a domain (B) comprising a binding region of a heavy chain variable domain of a second immunoglobulin (VH2) specific for a CD3 epitope; and
   (iii) a domain (C);
   (B) the second polypeptide chain comprises, in the N-terminal to C-terminal direction:
   (i) a domain (D) comprising a binding region of a light chain variable domain of the second immunoglobulin (VL2) specific for the CD3 epitope;
   (ii) a domain (E) comprising a binding region of a heavy chain variable domain of the first immunoglobulin (VH1) specific for the HIV epitope;
   (iii) a domain (F);
   (C) (i) domains (A) and (B) do not associate with one another to form an epitope-binding domain;
   (ii) domains (D) and (E) do not associate with one another to form an epitope-binding domain;
   (iii) domains (A) and (E) associate to form an epitope-binding domain that binds the HIV epitope, and domains (B) and (D) associate to form an epitope-binding domain that binds the CD3 epitope,
   (iv) domains (C) and (F) are covalently associated together; and
   (D) (i) said VL1 comprises CDR1, CDR2 and CDR3 of the VL of anti-HIV antibody A32, said A32 VL CDRs comprising residues 23-36, residues 52-58, and residues 91-100 of SEQ ID NO: 46;
   (ii) said VH1 comprises CDR1, CDR2 and CDR3 of the VH of said anti-HIV antibody A32, said A32 VH CDRs comprising residues 149-155, residues 170-185, and residues 218-230 of SEQ ID NO: 47;
   (iii) said VL2 comprises CDR1, CDR2 and CDR3 of the VL of humanized anti-CD3 Antibody 2, said humanized anti-CD3 Antibody 2 VL CDRs comprising residues 23-36, residues 52-58, and residues 91-99 of SEQ ID NO: 47; and
   (iv) said VH2 comprises CDR1, CDR2 and CDR3 of the VH of said humanized anti-CD3 Antibody 2, said humanized anti-CD3 Antibody 2 VH CDRs comprising residues 149-153, residues 168-186, and residues 219-232 of SEQ ID NO:46.

2. The bispecific diabody of claim 1, wherein:
   (i) said domain (C) comprises a cysteine residue and an E coil or a K coil; and
   (ii) said domain (F) comprises a cysteine residue and a K coil if said domain (C) comprises an E coil; or an E coil if said domain (C) comprises a K coil.

3. A bispecific diabody comprising first and second polypeptide chains, wherein:
   (A) the first polypeptide chain comprises, in the N-terminal to C-terminal direction:
   (i) a domain (A) comprising a binding region of a light chain variable domain of a first immunoglobulin (VL1) specific for an HIV epitope;
   (ii) a domain (B) comprising a binding region of a heavy chain variable domain of a second immunoglobulin (VH2) specific for a CD3 epitope; and
   (iii) a domain (C);
   (B) the second polypeptide chain comprises, in the N-terminal to C-terminal direction:
   (i) a domain (D) comprising a binding region of a light chain variable domain of the second immunoglobulin (VL2) specific for the CD3 epitope;
   (ii) a domain (E) comprising a binding region of a heavy chain variable domain of the first immunoglobulin (VH1) specific for the HIV epitope;
   (iii) a domain (F);
   (C) (i) domains (A) and (B) do not associate with one another to form an epitope-binding domain;
   (ii) domains (D) and (E) do not associate with one another to form an epitope-binding domain;
   (iii) domains (A) and (E) associate to form an epitope-binding domain that binds the HIV epitope, and domains (B) and (D) associate to form a epitope-binding domain that binds the CD3 epitope,
   (iv) domains (C) and (F) are covalently associated together; and
   (D) (i) said VL1 comprises CDR1, CDR2 and CDR3 of the VL of anti-HIV antibody 7B2, said 7B2 VL CDRs comprising residues 24-40, residues 56-62, and acid residues 95-103 of SEQ ID NO: 48;

(ii) said VH1 comprises CDR1, CDR2 and CDR3 of the VH of said anti-HIV antibody 7B2, said 7B2 VH CDRs comprising residues 149-153, residues 168-184, and residues 217-233 of SEQ ID NO: 49;

(iii) said VL2 comprises CDR1, CDR2 and CDR3 of the VL of humanized anti-CD3 Antibody 2, said humanized anti-CD3 Antibody 2 VL CDRs comprising residues 23-36, residues 52-58, and residues 91-99 of SEQ ID NO:49; and (iv) said VH2 comprises CDR1, CDR2 and CDR3 of the VH of said humanized anti-CD3 Antibody 2, said humanized anti-CD3 Antibody 2 VH CDRs comprising residues 152-156, residues 171-189, and residues 222-235 of SEQ ID NO:48.

4. The bispecific diabody of claim 3, wherein:

(i) said domain (C) comprises a cysteine residue and an E coil or a K coil; and (ii) said domain (F) comprises a cysteine residue and a K coil if said domain (C) comprises an E coil; or an E coil if said domain (C) comprises a K coil.

5. A bispecific diabody comprising first, second and third polypeptide chains, wherein:

(A) the first polypeptide chain comprises, in the N-terminal to C-terminal direction:

(i) a domain (A) comprising a binding region of a light chain variable domain of a first immunoglobulin (VL1), said VL1 comprises CDR1, CDR2 and CDR3 of the VL of anti-HIV antibody A32, said A32 VL CDRs comprising residues 23-36, residues 52-58, and residues 91-100 of SEQ ID NO: 46;

(ii) a domain (B) comprising a binding region of a heavy chain variable domain of a second immunoglobulin (VH2), said VH2 comprises CDR1, CDR2, and CDR3 of the VH of a humanized anti-CD3 Antibody 2, said humanized anti-CD3 Antibody 2 VH CDRs comprising residues 149-153, residues 168-186, and residues 219-232 of SEQ ID NO: 46; and (iii) a domain (C) comprising a cysteine residue and an E coil or a K coil;

(B) the second polypeptide chain comprises, in the N-terminal to C-terminal direction:

(i) a domain (D) comprising a binding region of a light chain variable domain of the second immunoglobulin (VL2), said VL2 comprises CDR1, CDR2 and CDR3 of the VL of said humanized anti-CD3 Antibody 2, said humanized anti-CD3 Antibody 2 VL CDRs comprising residues 23-36, residues 52-58, and residues 91-99 of SEQ ID NO:47;

(ii) a domain (E) comprising a binding region of a heavy chain variable domain of the first immunoglobulin (VH1), said VH1 comprises CDR1, CDR2 and CDR3 of the VH of said anti-HIV antibody A32, said A32 VH CDRs comprising residues 149-155, residues 170-185, and said residues 218-230 of SEQ ID NO:47;

(iii) a domain (F) comprising:

(1) a cysteine residue and a K coil if the first polypeptide comprises an E coil; or (2) a cysteine residue and an E coil if the first polypeptide comprises a K coil;

(C) the third polypeptide chain comprises a CH2-CH3 region of an Fc region; and wherein (1) (i) the first polypeptide chain further comprises a CH2-CH3 region of an Fc region C-terminal to domain (C); or (ii) the second polypeptide chain further comprises a CH2-CH3 region of an Fc region C-terminal to domain (F);

(2) domains (A) and (B) do not associate with one another to form an epitope-binding domain;

(3) domains (D) and (E) do not associate with one another to form an epitope-binding domain;

(4) domains (A) and (E) associate to form an epitope-binding domain that binds the epitope bound by anti-HIV antibody A32, and domains (B) and (D) associate to form an epitope-binding domain that binds the epitope bound by humanized anti-CD3 Antibody 2;

(5) domains (C) and (F) are covalently associated together by a disulfide bond.

6. A bispecific diabody comprising first, second and third polypeptide chains, wherein:

(A) the first polypeptide chain comprises, in the N-terminal to C-terminal direction:

(i) a domain (A) comprising a binding region of a light chain variable domain of a first immunoglobulin (VL1), said VL1 comprises CDR1, CDR2 and CDR3 of the VL of anti-HIV antibody 7B2, said 7B2 VL CDRs comprising residues 24-40, residues 56-62, and residues 95-103 of SEQ ID NO: 48;

(ii) a domain (B) comprising a binding region of a heavy chain variable domain of a second immunoglobulin (VH2), said VH2 comprises CDR1, CDR2 and CDR3 of the VH of humanized anti-CD3 Antibody 2, said humanized anti-CD3 Antibody 2 VH CDRs comprising residues 152-156, residues 171-189, and residues 222-235 of SEQ ID NO:48; and (iii) a domain (C) comprising a cysteine residue and an E coil or a K coil;

(B) the second polypeptide chain comprises, in the N-terminal to C-terminal direction:

(i) a domain (D) comprising a binding region of a light chain variable domain of the second immunoglobulin (VL2), said VL2 comprises CDR1, CDR2 and CDR3 of the VL of said humanized anti-CD3 Antibody 2, said humanized anti-CD3 Antibody 2 VL CDRs comprising residues 23-36, residues 52-58, and residues 91-99 of SEQ ID NO:49;

(ii) a domain (E) comprising a binding region of a heavy chain variable domain of the first immunoglobulin (VH1), said VH1 comprises CDR1, CDR2 and CDR3 of the VH of said anti-HIV antibody 7B2, said 7B2 VH CDRs comprising residues 149-153, residues 168-184, and residues 217-233 of SEQ ID NO: 49;

(iii) a domain (F) comprising:

(1) a cysteine residue and a K coil if the first polypeptide has an E coil; or (2) a cysteine residue and an E coil if the first polypeptide has a K coil;

(D) the third polypeptide chain comprises a CH2-CH3 region of an Fc region; and wherein (1) (i) the first polypeptide chain further comprises a CH2-CH3 region of an Fc region C-terminal to domain (C); or (ii) the second polypeptide chain further comprises a CH2-CH3 region of an Fc region C-terminal to domain (F);

(2) domains (A) and (B) do not associate with one another to form an epitope-binding domain;

(3) domains (D) and (E) do not associate with one another to form an epitope-binding domain;

(4) domains (A) and (E) associate to form an epitope-binding domain that binds the epitope bound by anti-HIV antibody 7B2, and domains (B) and (D) associate to form an epitope-binding domain that binds the epitope bound by humanized anti-CD3 Antibody 2;

(5) domains (C) and (F) are covalently associated together by a disulfide bond.

7. A pharmaceutical composition comprising the bispecific diabody of claim 1, and a pharmaceutically acceptable carrier.

8. A pharmaceutical composition comprising the bispecific diabody of claim 3, and a pharmaceutically acceptable carrier.

9. A pharmaceutical composition comprising the bispecific diabody of claim 5, and a pharmaceutically acceptable carrier.

10. A pharmaceutical composition comprising the bispecific diabody of claim 6, and a pharmaceutically acceptable carrier.

11. A method of treating a latent HIV infection, or a persistent HIV infection, or an inactive HIV infection in an individual in need of such treatment, comprising the step of administering a therapeutically effective amount of the bispecific diabody of claim 1 to said individual.

12. A method of killing a cell containing an HIV genome, or a cell expressing an HIV protein, comprising the step of contacting said cell with the bispecific diabody of claim 1, whereby said cell containing said HIV genome, or expressing said HIV protein is killed.

13. The method of claim 12, wherein said cell containing said HIV genome, or expressing said HIV protein, is latently infected with HIV.

14. A method of treating a latent HIV infection, or a persistent HIV infection, or an inactive HIV infection in an individual in need of such treatment, comprising the step of administering a therapeutically effective amount of the bispecific diabody of claim 13 to said individual.

15. A method of killing a cell containing an HIV genome, or a cell expressing an HIV protein, comprising the step of contacting said cell with the bispecific diabody of claim 13, whereby said cell containing said HIV genome, or expressing said HIV protein is killed.

16. The method of claim 15, wherein said cell containing said HIV genome, or expressing said HIV protein, is latently infected with HIV.

17. A method of treating a latent HIV infection, or a persistent HIV infection, or an inactive HIV infection in an individual in need of such treatment, comprising the step of administering a therapeutically effective amount of the bispecific diabody of claim 15 to said individual.

18. A method of killing a cell containing an HIV genome, or a cell expressing an HIV protein, comprising the step of contacting said cell with the bispecific diabody of claim 15, whereby said cell containing said HIV genome, or expressing said HIV protein is killed.

19. The method of claim 18, wherein said cell containing said HIV genome, or expressing said HIV protein, is latently infected with HIV.

20. A method of treating a latent HIV infection, or a persistent HIV infection, or an inactive HIV infection in an individual in need of such treatment, comprising the step of administering a therapeutically effective amount of the bispecific diabody of claim 6 to said individual.

21. A method of killing a cell containing an HIV genome, or a cell expressing an HIV protein, comprising the step of contacting said cell with the bispecific diabody of claim 6, whereby said cell containing said HIV genome, or expressing said HIV protein is killed.

22. The method of claim 21, wherein said cell containing said HIV genome, or expressing said HIV protein, is latently infected with HIV.

* * * * *